United States Patent
von Andrian et al.

(10) Patent No.: US 10,307,487 B2
(45) Date of Patent: Jun. 4, 2019

(54) MICROVESSEL ENDOTHELIAL CELL SURFACE MARKERS AND USES THEREOF

(71) Applicants: PRESIDENT AND FELLOWS OF HARVARD COLLEGE, Cambridge, MA (US); THE BRIGHAM AND WOMEN'S HOSPITAL INC., Boston, MA (US)

(72) Inventors: Ulrich H. von Andrian, Brookline, MA (US); Aude Thiriot, Brookline, MA (US); Omid Farokhzad, Waban, MA (US); Jinjun Shi, Boston, MA (US)

(73) Assignees: President and Fellows of Harvard College, Cambridge, MA (US); The Brigham and Women's Hospital, Boston, MA (US)

( * ) Notice: Subject to any disclaimer, the term of this patent is extended or adjusted under 35 U.S.C. 154(b) by 0 days.

(21) Appl. No.: 14/903,964

(22) PCT Filed: Jul. 9, 2014

(86) PCT No.: PCT/US2014/046039
§ 371 (c)(1),
(2) Date: Jan. 8, 2016

(87) PCT Pub. No.: WO2015/006501
PCT Pub. Date: Jan. 15, 2015

(65) Prior Publication Data
US 2016/0339113 A1     Nov. 24, 2016

Related U.S. Application Data

(60) Provisional application No. 61/844,383, filed on Jul. 9, 2013.

(51) Int. Cl.
| | |
|---|---|
| *A61K 49/00* | (2006.01) |
| *A61K 47/48* | (2006.01) |
| *A61K 31/00* | (2006.01) |
| *G01N 33/50* | (2006.01) |
| *A61K 47/68* | (2017.01) |

(52) U.S. Cl.
CPC ........ *A61K 47/48561* (2013.01); *A61K 31/00* (2013.01); *A61K 47/6849* (2017.08); *A61K 49/00* (2013.01); *A61K 49/0058* (2013.01); *G01N 33/5064* (2013.01); *G01N 2333/705* (2013.01); *Y02A 50/385* (2018.01); *Y02A 50/406* (2018.01); *Y02A 50/409* (2018.01); *Y02A 50/411* (2018.01)

(58) Field of Classification Search
CPC ............................... A61K 31/00; A61K 39/00
See application file for complete search history.

(56) References Cited

U.S. PATENT DOCUMENTS

| | | | |
|---|---|---|---|
| 5,605,821 | A | 2/1997 | McEver et al. |
| 5,660,827 | A | 8/1997 | Thorpe et al. |
| 5,747,470 | A | 5/1998 | Becherer et al. |
| 5,767,241 | A | 6/1998 | McEver |
| 6,020,196 | A | 2/2000 | Hu et al. |
| 6,096,722 | A | 8/2000 | Bennett et al. |
| 6,528,487 | B1 | 3/2003 | Heavner et al. |
| 7,449,186 | B1 | 11/2008 | Masinovsky et al. |
| 8,003,101 | B2 * | 8/2011 | Life .................. A61K 31/00 |
| | | | 424/139.1 |
| 8,231,895 | B2 | 7/2012 | De Almeida Moreira et al. |
| 8,377,440 | B2 | 2/2013 | McEver et al. |
| 2004/0220129 | A1 | 11/2004 | Reich et al. |
| 2005/0048529 | A1 | 3/2005 | McSwiggen |
| 2005/0118164 | A1 * | 6/2005 | Herman ............... C07K 16/468 |
| | | | 424/133.1 |
| 2006/0024231 | A1 | 2/2006 | Schnitzer et al. |
| 2007/0160531 | A1 | 7/2007 | Schnitzer |
| 2008/0107621 | A1 | 5/2008 | Dreano et al. |
| 2009/0017030 | A1 | 1/2009 | St Croix et al. |
| 2009/0092663 | A1 | 4/2009 | Ponzoni et al. |
| 2013/0102546 | A1 | 4/2013 | Feinberg et al. |
| 2013/0109737 | A1 | 5/2013 | Young et al. |
| 2015/0232837 | A1 | 8/2015 | Thibonnier |
| 2016/0354403 | A1 | 12/2016 | von Andrian |

FOREIGN PATENT DOCUMENTS

| | | |
|---|---|---|
| WO | WO 2000/053236 A2 | 9/2000 |
| WO | WO 2006/086639 | 8/2006 |
| WO | WO 2010/103118 A1 | 9/2010 |
| WO | WO-2011/127175 A1 | 10/2011 |
| WO | WO 2015/006500 | 1/2015 |
| WO | WO 2015/006501 | 1/2015 |

OTHER PUBLICATIONS

Wang et al., CD44 antibody-targeted liposomal nanoparticles for molecular imaging and therapy of hepatocellular carcinoma. Biomaterials 33 (2012) 5107-5114.*
Taga et al., GP130 and the Interleukin-6 Family of Cytokines. Annu. Rev. Immunol. 1997. 15:797-819.*
Yao et al., Bone marrow dysfunction in mice lacking the cytokine receptor gp130 in endothelial cells. Blood, Dec. 15, 2005 vol. 106, No. 13, pp. 4093-4101 (Year: 2005).*
Modur et al., Retrograde Inflammatory Signaling from Neutrophils to Endothelial Cells by Soluble Interleukin-6 Receptor Alpha. J. Clin. Invest. vol. 100, No. 11, Dec. 1997, 2752-2756 (Year: 1997).*
Dahlman et al., "In vivo endothelial siRNA delivery using polymeric nanoparticles with low molecular weight," *Nature Nanotechnology*, Published Online: May 11, 2014:1-6.
Gp130/CD130 Phycoerythrin-Labeled Mouse Monoclonal Antibody. Neuromics catalog No. FC15014.
Hadley et al., "Postcapillary venule endothelial cells in kidney express a multispecific chemokine receptor that is structurally and functionally Identical to the erythroid isoform, which is the Duffy blood group antigen," *J Clion Invest.*, 94:985-991, (1994).

(Continued)

*Primary Examiner* — Scott Long
*Assistant Examiner* — Arthur S Leonard
(74) *Attorney, Agent, or Firm* — Clark & Elbing LLP

(57) ABSTRACT

Disclosed herein are microvessel endothelial cell surface markers and methods, compositions, agents, and kits relating to those surface markers.

12 Claims, 1 Drawing Sheet

(56) References Cited

OTHER PUBLICATIONS

Halin et al., "In vivo imaging of lymphocyte trafficking," *Annu Rev Cell Dev Biol.*, 21:581-603, (2005).
Jo et al., "VEGF-binding aptides and the inhibition of choroidal and retinal Neovascularization," *Biomaterials*, 35(9):3052-3059, Abstract, (2014).
Jon et al., "Aptide-based Nanomedicine for Cancer Imaging and Therapy," *Cell Dynamics Research Center, School of Life Sciences, Gwangju Institute of Science and Technology (GIST)*, Gwangju pp. 500-712, Korea.
Kang et al., "Regulation of Early Adipose Commitment by Zfp521," *PLOS Biology*, 10(11):1-9, (2012).
Ley et al., "Endothelial, not hemodynamic, differences are responsible for preferential leukocyte rolling in rat mesenteric venules," *Circulation Research*, 69:1034-1041, (1991).
Luster et al., "Immune cell migration in inflammation: present and future therapeutic targets," *Nature Immunology* 6(12):1182-1190, (2005).
Nielsen et al, "Sequence-selective recognition of DNA by strand displacement with a thlmine-substituted polyamide," *Science*, 254(5037):1497-1500, Abstract, (1991).
Park et al., "Fibronectin extra domain B-specific aptide conjugated nanoparticles for targeted cancer imaging," *J. Control Release*, 163(2):111-118, Abstract, (2012).
Park et al., "HER2-specific aptide conjugated magneto-nanoclusters for potential breast cancer imaging and therapy," *J. Mater. Chem. B.*, 1:4576-4583, Abstract, (2013).
Peiper et al., "The Duffy antigen/receptor for chemokines (DARC) is expressed in endothelial cells of Duffy negative individuals who lack the erythrocyte receptor," *J. Exp Med.*, 181:1311-1317, (1995).
Von Andrian et al., "T-cell function and migration. Two sides of the same coin," *New Engl Jour Med.*, 343(14):1020-1034, (2000).
Von Andrian, "Segmental specialization of endothelial cells: A new approach to drug discovery and anti-inflammatory therapy," *UCB Meeting*, HMS, Boston, Feb. 13, 2013.
Yao et al, "Elevated CXCL1 expression in gp130-deficient endothelial cells impairs neutrophil migration in mice," *Blood*, 122(23):3832-3842, (2013).

International Search Report for International Application PCT/US2014/46037, dated Dec. 24, 2014.
International Search Report for International Application PCT/US2014/46039, dated Dec. 30, 2014.
Malik, "Targeting Endothelial Cell Surface Receptors: Novel Mechanisms of Microvascular Endothelial Barrier Transport," *Journal of Medical Sciences*, 2(2):13-17, (2009).
Massey, et al., "Targeting and Imaging Signature Caveolar Molecules in Lungs," *Proceedings of the American Thoracic Society*, 6:419-430, (2009).
Simone, et al., "Targeted Delivery of Therapeutics to Endothelium," *Cell and Tissue Research*, 335(1):283-300, (Sep. 25, 2008).
Muzykantov, et al., "Dynamic Factors Controlling Targeting Nanocarriers to Vascular Endothelium," *Curr. Drug Metab.*, 13(1):70-81, (Jan. 1, 2012).
Extended European Search Report from EP 14823750.6, dated Feb. 14, 2017.
Non-Final Office Action from U.S. Appl. No. 14/903,899, dated Feb. 9, 2017.
Von Andrian, Ulrich H. Abstract "T Cell Activation in Lymph Nodes." National Institutes of Health Grant No. 1R01AI069259-01 (Funding Start Date Mar. 1, 2006).
Von Andrian, Ulrich H. Abstract "Anti-Viral Immune Responses in Lymph Node." National Institutes of Health Grant No. 1P01AI078897-01 (Funding Start Date Aug. 15, 2008).
Lacorre, et al., "Plasticity of Endothelial Cells: Rapid Dedifferentiation of Freshly Isolated High Endothelial Venule Endothelial Cells Outside the Lymphoid Tissue Microenvironment," *Blood*, 103(11):4164-4172, (Jun. 2004).
Supplementary Partial European Search Report from EP 14 82 2681, dated Dec. 8, 2016.
Extended European Search Report from EP 14822681.4, dated Mar. 24, 2017.
Palombella, et al., Role of the Proteasome and NF-KappaB in Streptococcal Cell Wall-Induced Polyarthritis, *PNAS*, 95:15671-15676, (1998).
Final Office Action from U.S. Appl. No. 14/903,899, dated Jun. 7, 2017.
Xu et al., "Discovery of a Novel Orally Active Small-Molecule gp130 Inhibitor for the Treatment of Ovarian Cancer," Mol Cancer Ther 12(6):937-950 (2013).

\* cited by examiner

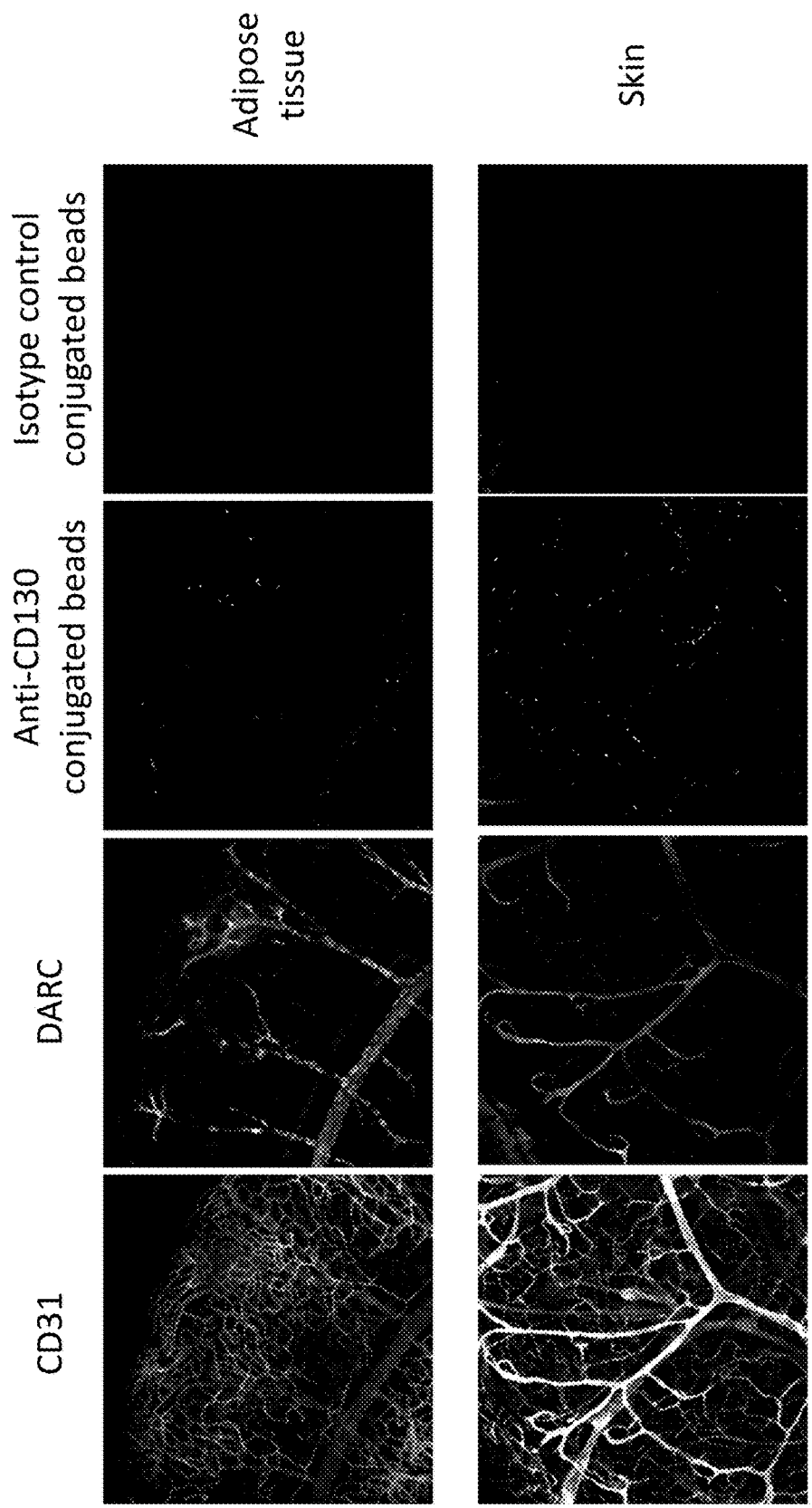

MICROVESSEL ENDOTHELIAL CELL SURFACE MARKERS AND USES THEREOF

RELATED APPLICATIONS

This application is a national stage filing under 35 U.S.C. 371 of International Application No. PCT/US2014/46039, filed Jul. 9, 2014, which claims the benefit of U.S. Provisional Application Ser. No. 61/844,383, filed Jul. 9, 2013, the teachings of which are incorporated herein by reference in their entirety. International Application PCT/US2014/46039 was published under PCT Article 21(2) in English

GOVERNMENT SUPPORT

This invention was made with government support under RO1 AI069259 and PO1 AI078897 awarded by the National Institute of Allergy and Infectious Diseases of the National Institutes of Health. The government has certain rights in the invention.

BACKGROUND OF THE INVENTION

Current anti-inflammatory drugs, such as corticoids, non-steroidal drugs and biologics, typically act systemically and thus affect both healthy and damaged tissues. Adverse side effects include gastrointestinal and renal effects as well as, in some cases, an increased susceptibility to infection linked to impaired leukocyte trafficking in healthy tissue. There are currently no FDA-approved anti-inflammatory agents that selectively target the endothelium, much less tissue-specific vascular beds that promote inflammation. Accordingly, there is a need for agents (e.g., anti-inflammatory agents) that specifically target venular endothelium, either globally or in a tissue-specific manner.

SUMMARY OF THE INVENTION

In some aspects, disclosed herein is a method of delivering an agent to a microvessel endothelial cell in a subject, comprising administering to the subject a microvessel endothelial cell targeting agent which binds to a protein expressed on the surface of a microvessel endothelial cell.

In some embodiments, the microvessel endothelial cell targeting agent causes an effect in the microvessel endothelial cell, or a microvessel, tissue or organ adjacent to the microvessel endothelial cell.

In some embodiments, the microvessel endothelial cell targeting agent is coupled to an agent which causes an effect in the microvessel endothelial cell, or a microvessel, tissue or organ adjacent to the microvessel endothelial cell.

In some embodiments, the protein expressed on the surface of the microvessel endothelial cell is encoded by a gene that is preferentially expressed in microvessels. In some embodiments, the gene is selected from the group consisting of Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some embodiments, the microvessel endothelial cell targeting agent is internalized into or transported across the endothelial cells lining the microvessel. In some embodiments, internalization of the microvessel endothelial cell targeting agent into the endothelial cells lining the microvessel causes the microvessel endothelial cell targeting agent to accumulate in a microvessel, tissue or organ adjacent to the microvessel endothelial cell. In some embodiments, the microvessel endothelial cell targeting agent does not accumulate in non-target tissues. In some embodiments, internalization of the microvessel endothelial cell targeting agent into the endothelial cells lining the microvessel causes the agent to accumulate in a microvessel, tissue or organ adjacent to the microvessel endothelial cell. In some embodiments, the agent does not accumulate in non-target tissue. In some embodiments, the agent is internalized into or transported across the endothelial cells lining the microvessel. In some embodiments, internalization of the agent into the endothelial cells lining or transport across the endothelial lining of the microvessel causes the agent to accumulate in a microvessel, tissue, or organ adjacent to the microvessel endothelial cell. In some embodiments, the agent does not accumulate in non-target tissues.

In some embodiments, the microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the microvessel endothelial cell targeting agent is coupled to the agent via a linker. In some embodiments, the microvessel endothelial cell targeting agent or the agent is coupled to a detectable reporter. In some embodiments, the microvessel endothelial cell targeting agent and/or the agent is encapsulated in a nanoparticle or microparticle. In some embodiments, the nanoparticle or microparticle comprises a lipid nanoparticle or microparticle.

In some embodiments, delivering an agent to microvessel endothelial cells of the subject treats, prevents, or ameliorates a symptom of, a disease in the subject. In some embodiments, the disease is an inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some embodiments, the disease is disease of the microvasculature. In some embodiments, the disease is selected from the group consisting of a venular disorder and a non-venular disorder.

In some aspects, disclosed herein is a method of delivering an agent to a venule endothelial cell in a subject, comprising administering to the subject a venule endothelial cell targeting agent which binds to a protein expressed on the surface of a venule endothelial cell.

In some embodiments, the venule endothelial cell targeting agent causes an effect in the venule endothelial cell, or venule, tissue, or organ adjacent to the venule endothelial cell.

In some embodiments, the venule endothelial cell targeting agent is coupled to an agent which causes an effect in the venule endothelial cell, or a venule, tissue or organ adjacent to the venule endothelial cell.

In some embodiments, the protein expressed on the surface of the venule endothelial cell is encoded by a gene exhibiting higher expression levels in venule endothelial cells compared to non-venule endothelial cells. In some embodiments, the gene is selected from the group consisting of Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In some embodiments, the venule endothelial cell targeting agent is internalized into or transported across the endothelial cells lining the venule. In some embodiments, internalization of the venule endothelial cell targeting agent into the endothelial cells lining the venule causes the venule endothelial cell targeting agent to accumulate in a venule, tissue or organ adjacent to the venule endothelial cell. In some embodiments, the venule endothelial cell targeting agent does not accumulate in non-target vessels, tissues, or organs.

In some embodiments, internalization of the venule endothelial cell targeting agent into the endothelial cells lining the venule causes the agent to accumulate in a venule, tissue or organ adjacent to the venule endothelial cell. In some embodiments, the agent does not accumulate in non-target venules, tissues, or organs. In some embodiments, the agent is internalized into or transported across the endothelial cells lining the venule. In some embodiments, internalization of the agent into the endothelial cells lining or transport across the endothelial lining of the venule causes the agent to accumulate in a venule, tissue, or organ adjacent to the venule endothelial cell. In some embodiments, the agent does not accumulate in non-target vessels, tissues, or organs.

In some embodiments, the venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the venule endothelial cell targeting agent is coupled to the agent via a linker. In some embodiments, the venule endothelial cell targeting agent or the agent is coupled to a detectable reporter. In some embodiments, the venule endothelial cell targeting agent and/or the agent is encapsulated in a nanoparticle or microparticle. In some embodiments, the nanoparticle comprises a lipid nanoparticle or microparticle.

In some embodiments, delivering an agent to venule endothelial cells of the subject treats, prevents, or ameliorates a symptom of, a disease in the subject. In some embodiments, the disease is an inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some aspects, disclosed herein is a method of delivering an agent to a non-venule endothelial cell in a subject, comprising administering to the subject a non-venule endothelial cell targeting agent which binds to a protein expressed on the surface of a non-venule endothelial cell.

In some embodiments, the non-venule endothelial cell targeting agent causes an effect in the non-venule endothelial cell, or non-venule, tissue, or organ adjacent to the non-venule endothelial cell.

In some embodiments, the non-venule endothelial cell targeting agent is coupled to an agent which causes an effect in the non-venule endothelial cell, or a non-venule, tissue or organ adjacent to the non-venule endothelial cell.

In some embodiments, the protein expressed on the surface of the non-venule endothelial cell is encoded by a gene exhibiting higher expression levels in non-venule endothelial cells compared to venule endothelial cells. In some embodiments, the gene is selected from the group consisting of Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. In some embodiments, the gene is selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some embodiments, the non-venule endothelial cell targeting agent is internalized into or transported across the endothelial cells lining the non-venule. In some embodiments, internalization of the non-venule endothelial cell targeting agent into the endothelial cells lining the non-venule causes the non-venule endothelial cell targeting agent to accumulate in a non-venule, tissue or organ adjacent to the non-venule endothelial cell. In some aspects, the non-venule endothelial cell targeting agent does not accumulate in non-target vessels, tissues, or organs. In some embodiments, internalization of the non-venule endothelial cell targeting agent into the endothelial cells lining the non-venule causes the agent to accumulate in a non-venule, tissue or organ adjacent to the non-venule endothelial cell. In some embodiments, the agent does not accumulate in non-target vessels, tissues, or organs. In some embodiments, the agent is internalized into or transported across the endothelial cells lining the non-venule. In some embodiments, internalization of the agent into the endothelial cells lining or transport across the endothelial lining of the non-venule causes the agent to accumulate in a non-venule, tissue, or organ adjacent to the non-venule endothelial cell. In some embodiments, the agent does not accumulate in non-target vessels, tissues, or organs.

In some embodiments, the non-venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the non-venule endothelial cell targeting agent is coupled to the agent via a linker. In some embodiments, the non-venule endothelial cell targeting agent or the agent is coupled to a detectable reporter. In some embodiments, the non-venule endothelial cell targeting agent and/or the agent is encapsulated in a nanoparticle or microparticle. In some embodiments, the nanoparticle comprises a lipid nanoparticle or microparticle.

In some embodiments, delivering an agent to non-venule endothelial cells of the subject treats, prevents, or ameliorates a symptom of, a disease in the subject.

In some embodiments, the disease is non-venular disease. In some embodiments, the non-venular disease is selected from the group consisting of small vessel coronary disease (e.g., cardiac syndrome X, microvascular dysfunction, non-obstructive coronary disease, and microvascular angina), thrombotic microangiopathy, microangiopathic haemolytic anaemia, microvascular occlusion, cutaneous diabetic microagniopathy, Susac's syndrome, cerebral microangiopathy, early diabetic microangiopathy, diabetic microangiopathy, glomerular microangiopathy, non-neoplastic nevus, pulmonary microangiopathy, pulmonary capillaritis (e.g., isolated pauci-immune pulmonary capillaritis), coronary microvascular disease, chronic microvascular diseases, small vessel ischemia, thrombotic thrombocytopenic purpura, arteriolosclerosis, and arterioloephosclerosis, teleangiectasia (e.g., hereditary hemorrhagic telangiectasia), and scleroderma.

In some aspects, disclosed herein is a method of delivering an agent to a microvessel endothelial cell in skin, comprising administering to a subject a skin microvessel endothelial cell targeting agent which binds to a protein expressed on the surface of a microvessel endothelial cell in skin.

In some embodiments, the skin microvessel endothelial cell targeting agent causes an effect in the skin microvessel endothelial cell, or microvessel, tissue, or organ adjacent to the skin microvessel endothelial cell.

In some embodiments, the skin microvessel endothelial cell targeting agent is coupled to an agent which causes an effect in the skin microvessel endothelial cell, or microvessel, tissue, or organ adjacent to the skin microvessel endothelial cell.

In some embodiments, the protein expressed on the surface of the skin microvessel endothelial cell is encoded by a gene exhibiting higher expression levels in skin venule endothelial cells compared to skin non-venule endothelial cells. In some embodiments, the gene is selected from the group consisting of Nrp2, Gpr1, C630004H02Rik, Fndc1, 2310046K01Rik, Insr, and Slco2a1. In some embodiments, the gene is selected from the group consisting of Nrp2, Htr2b, Mr1, Lifr, Anxa1, Lphn2, Vamp5, Olr1, Eps8, Slco2b1, and Slco2a1.

In some embodiments, the protein expressed on the surface of the skin microvessel endothelial cell is encoded by a gene exhibiting higher expression levels in skin non-venule endothelial cells compared to skin venule endothelial cells. In some embodiments, the gene is selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the gene is selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap11, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

In some embodiments, the skin microvessel endothelial cell targeting agent is internalized into or transported across the endothelial cells lining a microvessel in the subject's skin. In some embodiments, internalization of the skin microvessel endothelial cell targeting agent into the endothelial cells lining the microvessel in the subject's skin causes the skin microvessel endothelial cell targeting agent to accumulate in subject's skin. In some embodiments, the skin microvessel endothelial cell targeting agent does not accumulate in tissues other than skin. In some embodiments, internalization of the skin microvessel endothelial cell targeting agent into the endothelial cells lining the microvessel in the subject's skin causes the agent to be internalized into or transported across the endothelial cells lining the microvessel in the subject's skin. In some embodiments, internalization or transport of the agent causes the agent to accumulate in the subject's skin. In some embodiments, the agent does not accumulate in tissues other than skin. In some embodiments, the agent is internalized into or transported across the endothelial cells lining a microvessel in the subject's skin. In some embodiments, internalization or transport of the agent causes the agent to accumulate in the subject's skin. In some embodiments, the agent does not accumulate in tissues other than skin.

In some embodiments, the skin microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the skin microvessel endothelial cell targeting agent is coupled to the agent via a linker. In some embodiments, the skin microvessel endothelial cell targeting agent or agent is coupled to a detectable reporter.

In some embodiments, delivering an agent to skin microvessel endothelial cells of the subject treats, prevents, or ameliorates a symptom of, a skin disease. In some embodiments, the skin disease is selected from the group consisting of acne, alopecia (e.g., alopecia areata, alopecia totalis, alopecia universalis, traction alopecia), angioma, athlete's foot, basal cell carcinoma, bed sore, Behcet's Disease, blepharitis, boil, calluses and corns, canker sore, carbuncles, candidiasis (e.g., oral (oral thrush), vaginal (candidal vulvovaginitis), penile (candidal balanitis), in the diaper area (diaper rash), in the skin folds (candidal intertrigo), cellulitis, cold sores, creeping eruption, dandruff, dermatitis (eczema) (e.g., atopic dermatitis, contact dermatitis, seborrhoeic dermatitis, cradle cap, nummular dermatitis, stasis dermatitis, perioral dermatitis (muzzle rash), dermatitis herpetiformis), dermatofibroma, Bowen's Disease, bullous pemphigoid, echtima, eczema, epidermolysis bullosa (e.g., simplex, junctional, dystrophic, hemidesmosomal), erythrasma, erysipelas, folliculitis, friction blisters, herpes (e.g., HHV1 i.e., cold sores, HHV2 i.e., genital herpes, HHV3, e.g., chickenpox, shingles, HHV6, HHV7, e.g., roseola infantum, sixth disease, HHV8, i.e., Kaposi's sarcoma herpesvirus), hidradenitis suppurativa, hives, hyperhidrosis, ichthyosis, impetigo, jock itch, Kaposi's sarcoma, keloid, keratoacanthoma, keratosis (e.g., actinic (solar) keratosis, keratosis pilaris, keratosis follicularis (Daffier's disease), seborrheic, and hyperkeratosis), lice infection, lichen planus, lichen simplex chronicus, lipoma, lymphadenitis, malignant melanoma, melisma, miliaria, molluscum contagiosum, Paget's disease of the nipple, pediculosis, pemphigus, photoallergy, photosensitivity, *pityriasis rosea, pityriasis rubra* pilaris, psoriasis, Raynaud's disease, ring worm, Raynaud's disease, rosacea, Saint Anthony's fire, scabies, scleroderma, sebaceous cyst, shingles, skin cancer, skin tags, spider veins (telangiectasia), squamous cell carcinoma, tick bite, tinea: (barbae, capitis, corporis, cruris (Jock Itch), pedis unguium, *versicolor*), trichomycosis, varicose veins, vitiligo, warts (e.g., common, planar, genital).

In some embodiments, the skin disease is a skin inflammatory disease. In some embodiments, the skin inflammatory disease is selected from the group consisting of acne, dermatitis, eczema, oily skin, rosacea, cutaneous lymphoma and urticaria. In some embodiments, the dermatitis is selected from the group consisting of atopic dermatitis, psoriasis and contact dermatitis.

In some aspects, disclosed herein is a microvessel endothelial cell in adipose tissue, comprising administering to a subject an adipose tissue microvessel endothelial cell targeting agent which binds to a protein expressed on the surface of a microvessel endothelial cell in adipose tissue.

In some embodiments, the adipose tissue microvessel endothelial cell targeting agent causes an effect in the adipose tissue microvessel endothelial cell, or microvessel, tissue, or organ adjacent to the adipose tissue microvessel endothelial cell.

In some embodiments, the adipose tissue microvessel endothelial cell targeting agent is coupled to an agent which causes an effect in the adipose tissue microvessel endothelial cell, or microvessel, tissue, or organ adjacent to the adipose tissue microvessel endothelial cell.

In some embodiments, the protein expressed on the surface of the adipose tissue microvessel endothelial cell is encoded by a gene exhibiting higher expression levels in adipose tissue venule endothelial cells compared to adipose tissue non-venule endothelial cells. In some embodiments, the gene is selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the gene is selected from the group consisting of Il1rl1, Tnfrsf1la, Mpz, Dnm3os, Icosl, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the protein expressed on the surface of the adipose tissue microvessel endothelial cell is encoded by a gene exhibiting higher expression levels in adipose tissue non-venule endothelial cells compared to adipose tissue venule endothelial cells. In some embodiments, the gene is selected from the group consisting of Adora2a, H2-Ab1, Hspg2, Gpr81, Kcna5, Jam3, and Gpc4. In some embodiments, the gene is selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some embodiments, the adipose tissue microvessel endothelial cell targeting agent is internalized into or transported across the endothelial cells lining a microvessel in the subject's adipose tissue. In some embodiments, internalization of the adipose tissue microvessel endothelial cell targeting agent into the endothelial cells lining the microvessel in the subject's adipose tissue causes the adipose tissue microvessel endothelial cell targeting agent to accumulate in subject's adipose tissue. In some embodiments, the adipose tissue microvessel endothelial cell targeting agent does not accumulate in tissues other than adipose tissue. In some embodiments, internalization of the adipose tissue microvessel endothelial cell targeting agent into the endothelial cells lining the microvessel in the subject's adipose tissue causes the agent to be internalized into or transported across the endothelial cells lining the microvessel in the subject's adipose tissue. In some embodiments, internalization or transport of the agent causes the agent to accumulate in the subject's adipose tissue. In some embodiments, the agent does not accumulate in tissues other than adipose tissue. In some embodiments, the agent is internalized into or transported across the endothelial cells lining a microvessel in the subject's adipose tissue. In some embodiments, internalization or transport of the agent causes the agent to accumulate in the subject's adipose tissue. In some embodiments, the agent does not accumulate in tissues other than adipose tissue.

In some embodiments, the adipose tissue microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the adipose tissue microvessel endothelial cell targeting agent is coupled to the agent via a linker. In some embodiments, the adipose tissue microvessel endothelial cell targeting agent or agent is coupled to a detectable reporter.

In some embodiments, targeting an agent to the subject's adipose tissue microvessel endothelial cells treats, prevents, or ameliorates a symptom of, an adipose tissue disease. In some embodiments, the adipose tissue disease is selected from the group consisting of obesity and related disorders selected from the group consisting of cancer, cellulitis, chronic renal failure, depression, diabetes, erectile dysfunction, fatty liver disease, gallbladder disease (e.g., gallstones), gastro-esophageal reflux disease, gout, heart disease (e.g., congestive heart failure, enlarged heart), hernia, high blood pressure, hypercholesterolemia, infection, infertility, lymph edema, osteoarthritis, pain, Pickwickian syndrome, pulmonary embolism, polycystic ovarian syndrome, ulcers, stroke, and urinary incontinence.

In some embodiments, targeting an agent to the subject's adipose tissue microvessel endothelial cells treats, prevents, or ameliorates a symptom of, a disease characterized by inflammation in the subject's visceral fat. In some embodiments, the disease is selected from the group consisting of cancer, CVHD, fibrosis, hypertension, lypodystrophy, obesity, metabolic syndrome, and type II diabetes.

In some aspects, disclosed herein is a method of delivering an agent to a microvessel endothelial cell in lymph nodes, comprising administering to a subject a lymph node microvessel endothelial cell targeting agent which binds to a protein expressed on the surface of a microvessel endothelial cell in the lymph nodes.

In some embodiments, the lymph node microvessel endothelial cell targeting agent causes an effect in the lymph node microvessel endothelial cell, or microvessel, tissue, or organ adjacent to the lymph node microvessel endothelial cell.

In some embodiments, the lymph node microvessel endothelial cell targeting agent is coupled to an agent which causes an effect in the lymph node microvessel endothelial cell, or microvessel, tissue, or organ adjacent to the lymph node microvessel endothelial cell.

In some embodiments, the protein expressed on the surface of the lymph node microvessel endothelial cell is encoded by a gene exhibiting higher expression levels in lymph node venule endothelial cells compared to lymph node non-venule endothelial cells. In some embodiments, the gene is selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg.

In some embodiments, the protein expressed on the surface of the lymph node microvessel endothelial cell is encoded by a gene exhibiting higher expression levels in lymph node non-venule endothelial cells compared to lymph node venule endothelial cells. In some embodiments, the gene is selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the gene is selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

In some embodiments, the lymph node microvessel endothelial cell targeting agent is internalized into or transported across the endothelial cells lining a microvessel in the subject's lymph nodes. In some embodiments, internalization of the lymph node microvessel endothelial cell targeting agent into the endothelial cells lining the microvessel in the subject's lymph nodes causes the lymph node microvessel endothelial cell targeting agent to accumulate in subject's lymph nodes. In some embodiments, the lymph node microvessel endothelial cell targeting agent does not accumulate in tissues other than lymph nodes. In some embodiments, internalization of the lymph node microvessel endothelial cell targeting agent into the endothelial cells lining the microvessel in the subject's lymph nodes causes the agent to be internalized into or transported across the endothelial cells lining the microvessel in the subject's lymph nodes. In some embodiments, internalization or transport of the agent causes the agent to accumulate in the subject's lymph nodes. In some embodiments, the agent does not accumulate in tissues other than lymph nodes. In some embodiments, the agent is internalized into or transported across the endothelial cells lining a microvessel in the subject's lymph nodes. In some embodiments, internalization or transport of the agent causes the agent to accumulate in the subject's lymph nodes. In some embodiments, the agent does not accumulate in tissues other than lymph nodes.

In some embodiments, the lymph node microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises a cytotoxic agent. In some embodiments, the cytotoxic agent is selected from the group consisting of taxol; a nitrogen mustard selected from the group consisting of mechlorethamine, cyclophosphamide, melphalan, uracil mustard and chlorambucil; thiotepa; busulfan; a nitrosourea selected from the group consisting of carmustine, lomustine, semustine and streptozocin; dacarbazine; methotrexate; fluorouracil, cytarabine, azaribine; a purine analogs selected from the group consisting of mercaptopurine and thioguanine; a vinca alkaloids selected from the group consisting of vinblastine and vincristine; an antibiotic selected from the group consisting of dactinomycin, daunorubicin, doxorubicin, bleomycin, mithramycin and mitomycin; L-asparaginase; cisplatin; hydroxyurea; procarbazine; anti-virals; vaccines; and photodynamic dyes. In some embodiments, the agent comprises a chemotherapeutic agent. In some embodiments, the chemotherapeutic agent is selected from the group consisting of vinblastine, doxorubicin, bleomycin, methotrexate, 5-fluorouracil, 6-thioguanine, cytarabine, cyclophosphamide and cisplatinum. In some embodiments, the agent comprises a diagnostic agent. In some embodiments, the agent comprises an imaging agent. In some embodiments, the lymph node microvessel endothelial cell targeting agent is coupled to the agent via a linker. In some embodiments, the microvessel endothelial cell targeting agent is coupled to a detectable reporter.

In some embodiments, delivering an agent to lymph node microvessel endothelial cells of the subject treats, prevents, or ameliorates a symptom of, a lymph node disease. In some embodiments, the lymph node disease is selected from the group consisting of lymphoma, Hodgkins disease, tuberculosis, kikuchi disease, metastatic lymph node disease, lymphatic filiaris, mesenteric lymphadenitis, Castleman disease, lymphadenopathy, infiltration of the lymph nodes by metabolite-laden macrophages (e.g., lipid storage disorders such as Gaucher disease or Niemann-Pick disease, histiocytosis, cancer, lymphoid leukemia, splenomegaly, e.g., caused by sickle cell anemia, sarcoidosis, malaria, bacterial endocarditis, leukemia, pernicious anemia, Gaucher's disease, leishmaniasis, Hodgkin's disease, Banti's disease, hereditary spherocytosis, cysts, glandular fever), asplenia, hemangiomas, and hemangiosarcomas.

In some embodiments, targeting an agent to lymph node microvessel endothelial cells of the subject treats, prevents, or ameliorates a symptom of, a disease characterized by lymphadenopathy or lymphadenitis. In some embodiments, the disease is selected from the group consisting of cancer, a connective tissue disorder, and infection. In some embodiments, the cancer is selected from the group consisting of leukemias, lymphomas, and metastatic cancer. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome.

In some aspects, disclosed herein is a method of treating a microvessel endothelial cell-associated disorder in a subject in need thereof, comprising administering to the subject an effective amount of a therapeutic agent for treating the microvessel endothelial cell-associated disorder coupled to a microvessel endothelial cell targeting agent which binds to a protein expressed on the surface of a microvessel endothelial cell.

In some embodiments, the protein expressed on the surface of the microvessel endothelial cell is encoded by a gene that is preferentially expressed in microvessels.

In some embodiments, the gene is selected from the group consisting of Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1rl1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Ill1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some embodiments, the microvessel endothelial cell targeting agent delivers the coupled therapeutic agent to microvessel endothelial cells.

In some embodiments, delivery of the therapeutic agent to the microvessel endothelial cell induces a local therapeutic effect in the microvessel endothelial cell, or a microvessel, tissue or organ surrounding the microvessel endothelial cell. In some embodiments, delivery of the therapeutic agent to the microvessel endothelial cell minimizes or eliminates an effect in the subject selected from the group consisting of a systemic effect, a toxic effect, an adverse effect, a side effect, and an undesired effect. In some embodiments, the method further comprises modifying a dose of the therapeutic agent for local delivery to the microvessel endothelial cell. In some embodiments, the method further comprises selecting a subject who would likely benefit from delivery of therapeutic agent to the subject's venules. In some embodiments, the microvessel endothelial cell-associated disorder is selected from the group consisting of a venular disorder and a non-venular disorder. In some embodiments, the microvessel endothelial cell-associated disorder is selected from the group consisting of: (1) a venular disorder selected from the group consisting of high endothelial venules, rheumatoid arthritis, chronic inflammation associated with high endothelial venules, inflammatory bowel diseases, venule occlusion, small vessel disease, cardiovascular disease associated with small vessel disease, age-related small vessel diseases, hypertension-related small vessel diseases, and cerebral amyloid angiopathy, and (2) a non-venular disorder selected from the group consisting of small vessel coronary disease, thrombotic microangiopathy, microangiopathic haemolytic anaemia, microvascular occlusion, cutaneous diabetic microagniopathy, Susac's syndrome, cerebral microangiopathy, early diabetic microangiopathy, diabetic microangiopathy, glomerular microangiopathy, non-neoplastic nevus, pulmonary microangiopathy, pulmonary capillaritis, chronic microvascular diseases, small vessel ischemia, thrombotic thrombocytopenic purpura, arteriolosclerosis, and arterioloephosclerosis, teleangiectasia, and scleroderma.

In some aspects, disclosed herein is a method of treating a venule endothelial cell-associated disorder in a subject in need thereof, comprising administering to the subject an effective amount of a therapeutic agent for treating the venule endothelial cell-associated disorder coupled to a venule endothelial cell targeting agent which binds to a protein expressed on the surface of a venule endothelial cell.

In some embodiments, the protein expressed on the surface of the venule endothelial cell is encoded by a gene that is preferentially expressed in venule endothelial cells. In some embodiments, the gene is selected from the group consisting of Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1. In some embodiments, the venule endothelial cell targeting agent delivers the coupled therapeutic agent to venule endothelial cells. In some embodiments, delivery of the therapeutic agent to the venule endothelial cell induces a local therapeutic effect in the venule endothelial cell, or a venule, tissue or organ surrounding the venule endothelial cell. In some embodiments, delivery of the therapeutic agent to the venule endothelial cell minimizes or eliminates an effect in the subject selected from the group consisting of a systemic effect, a toxic effect, an adverse effect, a side effect, and an undesired effect. In some embodiments, the method further comprises modifying a dose of the therapeutic agent for local delivery to the venule endothelial cell. In some embodiments, the method further comprises selecting a subject who would likely benefit from delivery of the therapeutic agent to the subject's venule endothelial cells.

In some embodiments, the venule endothelial cell-associated disorder is an inflammatory disease selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease. In some embodiments, the venule endothelial cell-associated disorder is a venular disorder selected from the group consisting of high endothelial venules, rheumatoid arthritis, chronic inflammation associated with high endothelial venules, inflammatory bowel diseases, venule occlusion, small vessel disease, cardiovascular disease associated with small vessel disease, age-related small vessel diseases, hypertension-related small vessel diseases, and cerebral amyloid angiopathy.

In some aspects, disclosed herein is a method of treating a non-venule endothelial cell-associated disorder in a subject in need thereof, comprising administering to the subject an effective amount of a therapeutic agent for treating the non-venule endothelial cell-associated disorder coupled to a non-venule endothelial cell targeting agent which binds to a protein expressed on the surface of a non-venule endothelial cell.

In some embodiments, the protein expressed on the surface of the non-venule endothelial cell is encoded by a gene that is preferentially expressed in non-venule endothelial cells. In some embodiments, the gene is selected from the group consisting of Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. In some embodiments, the gene is selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some embodiments, the non-venule endothelial cell targeting agent delivers the coupled therapeutic agent to non-venule endothelial cells.

In some embodiments, delivery of the therapeutic agent to the non-venule endothelial cell induces a local therapeutic effect in the non-venule endothelial cell, or a non-venule, tissue or organ surrounding the non-venule endothelial cell. In some embodiments, delivery of the therapeutic agent to the non-venule endothelial cell minimizes or eliminates an effect in the subject selected from the group consisting of a systemic effect, a toxic effect, an adverse effect, a side effect, and an undesired effect. In some embodiments, the method further comprises modifying a dose of the therapeutic agent for local delivery to the non-venule endothelial cell. In some embodiments, the method further comprises selecting a subject who would likely benefit from delivery of the therapeutic agent to the subject's non-venule endothelial cells.

In some embodiments, the non-venule endothelial cell-associated disorder is selected from the group consisting of a non-venule microvessel disease selected from the group consisting of small vessel coronary disease (e.g., cardiac syndrome X, microvascular dysfunction, non-obstructive coronary disease, and microvascular angina), thrombotic microangiopathy, microangiopathic haemolytic anaemia, microvascular occlusion, cutaneous diabetic microagniopathy, Susac's syndrome, cerebral microangiopathy, early diabetic microangiopathy, diabetic microangiopathy, glomerular microangiopathy, non-neoplastic nevus, pulmonary microangiopathy, pulmonary capillaritis (e.g., isolated pauci-immune pulmonary capillaritis), coronary microvascular disease, chronic microvascular diseases, small vessel ischemia, thrombotic thrombocytopenic purpura, arteriolosclerosis, and arterioloephosclerosis, teleangiectasia (e.g., hereditary hemorrhagic telangiectasia), and scleroderma. In some embodiments, the non-venule endothelial cell-associated disorder is an inflammatory disease, a cardiovascular disease, or a respiratory disease.

In some aspects, disclosed herein is a method of treating a skin disorder in a subject in need thereof, comprising administering to the subject an effective amount of a therapeutic agent for treating the skin disorder coupled to a skin microvessel endothelial cell targeting agent which binds to a protein expressed on the surface of a skin microvessel endothelial cell.

In some embodiments, the protein expressed on the surface of the skin microvessel endothelial cell is encoded by a gene exhibiting higher expression levels in skin venule endothelial cells compared to skin non-venule endothelial cells. In some embodiments, the gene is selected from the group consisting of Nrp2, Gpr1, C630004H02Rik, Fndc1, 2310046K01Rik, Insr, and Slco2a1. In some embodiments, the gene is selected from the group consisting of Nrp2, Htr2b, Mr1, Lifr, Anxa1, Lphn2, Vamp5, Olr1, Eps8, Slco2b1, and Slco2a1.

In some embodiments, the protein expressed on the surface of the skin microvessel endothelial cell is encoded by a gene exhibiting higher expression levels in skin non-venule endothelial cells compared to skin venule endothelial cells. In some embodiments, the gene is selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the gene is selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

In some embodiments, the skin microvessel endothelial cell targeting agent delivers the coupled therapeutic agent to skin microvessel endothelial cells. In some embodiments, delivery of the therapeutic agent to the skin microvessel endothelial cell induces a local therapeutic effect in the skin microvessel endothelial cell, or a microvessel, tissue or organ surrounding the skin microvessel endothelial cell. In some embodiments, delivery of the therapeutic agent to the skin microvessel endothelial cell minimizes or eliminates an effect in the subject selected from the group consisting of a systemic effect, a toxic effect, an adverse effect, a side effect, and an undesired effect.

In some embodiments, the method further comprises modifying a dose of the therapeutic agent for local delivery to the skin microvessel endothelial cell. In some embodiments, the method further comprises selecting a subject who would likely benefit from delivery of the therapeutic agent to the subject's skin microvessel endothelial cells. In some embodiments, the skin disorder is a skin inflammatory disease selected from the group consisting of acne, dermatitis, eczema, oily skin, rosacea, cutaneous lymphoma and urticaria. In some embodiments, the skin disorder is selected from the group consisting of acne, alopecia (e.g., alopecia areata, alopecia totalis, alopecia universalis, traction alopecia), angioma, athlete's foot, basal cell carcinoma, bed sore, Behcet's Disease, blepharitis, boil, calluses and corns, canker sore, carbuncles, candidiasis (e.g., oral (oral thrush), vaginal (candidal vulvovaginitis), penile (candidal balanitis), in the diaper area (diaper rash), in the skin folds (candidal intertrigo), cellulitis, cold sores, creeping eruption, dandruff, dermatitis (eczema) (e.g., atopic dermatitis, contact dermatitis, seborrhoeic dermatitis, cradle cap, nummular dermatitis, stasis dermatitis, perioral dermatitis (muzzle rash), dermatitis herpetiformis), dermatofibroma, Bowen's Disease, bullous pemphigoid, echtima, eczema, epidermolysis bullosa (e.g., simplex, junctional, dystrophic, hemidesmosomal), erythrasma, erysipelas, folliculitis, friction blisters, herpes (e.g., HHV1 i.e., cold sores, HHV2 i.e., genital herpes, HHV3, e.g., chickenpox, shingles, HHV6, HHV7, e.g., roseola infantum, sixth disease, HHV8, i.e., Kaposi's sarcoma herpesvirus), hidradenitis suppurativa, hives, hyperhidrosis, ichthyosis, impetigo, jock itch, Kaposi's sarcoma, keloid, keratoacanthoma, keratosis (e.g., actinic (solar) keratosis, keratosis pilaris, keratosis follicularis (Darrier's disease), seborrheic, and hyperkeratosis), lice infection, lichen planus, lichen simplex chronicus, lipoma, lymphadenitis, malignant melanoma, melisma, miliaria, molluscum contagiosum, Paget's disease of the nipple, pediculosis, pemphigus, photoallergy, photosensitivity, *pityriasis rosea*, *pityriasis rubra* pilaris, psoriasis, Raynaud's disease, ring worm, Raynaud's disease, rosacea, Saint Anthony's fire, scabies, scleroderma, sebaceous cyst, shingles, skin cancer, skin tags, spider veins (telangiectasia), squamous cell carcinoma, tick bite, tinea: (barbae, capitis, corporis, cruris (Jock Itch), pedis unguium, *versicolor*), trichomycosis, varicose veins, vitiligo, and warts (e.g., common, planar, genital).

In some aspects, disclosed herein is a method of treating an adipose tissue disorder in a subject in need thereof, comprising administering to the subject an effective amount of a therapeutic agent for treating the adipose tissue disorder coupled to an adipose tissue microvessel endothelial cell targeting agent which binds to a protein expressed on the surface of an adipose tissue microvessel endothelial cell.

In some embodiments, the protein expressed on the surface of the adipose tissue microvessel endothelial cell is encoded by a gene exhibiting higher expression levels in adipose tissue venule endothelial cells compared to adipose tissue non-venule endothelial cells. In some embodiments, the gene is selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the gene is selected from the group consisting of Il1rl1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the protein expressed on the surface of the adipose tissue microvessel endothelial cell is encoded by a gene exhibiting higher expression levels in adipose tissue non-venule endothelial cells compared to adipose tissue venule endothelial cells. In some embodiments, the gene is selected from the group consisting of Adora2a, H2-Ab1, Hspg2, Gpr81, Kcna5, Jam3, and Gpc4. In some embodiments, the gene is selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some embodiments, the adipose tissue microvessel endothelial cell targeting agent delivers the coupled therapeutic agent to adipose tissue microvessel endothelial cells. In some embodiments, delivery of the therapeutic agent to the adipose tissue microvessel endothelial cell induces a local therapeutic effect in the adipose tissue microvessel endothelial cell, or a microvessel, tissue or organ surrounding the adipose tissue microvessel endothelial cell. In some embodiments, delivery of the therapeutic agent to the adipose tissue microvessel endothelial cell minimizes or eliminates an effect in the subject selected from the group consisting of a systemic effect, a toxic effect, an adverse effect, a side effect, and an undesired effect.

In some embodiments, the method further comprises modifying a dose of the therapeutic agent for local delivery to the adipose tissue microvessel endothelial cell. In some embodiments, the method further comprises selecting a subject who would likely benefit from delivery of the therapeutic agent to the subject's adipose tissue microvessel endothelial cells.

In some embodiments, the adipose tissue disorder is a disease characterized by visceral fat inflammation selected from the group consisting of cancer, CVHD, fibrosis, hypertension, lypodystrophy, obesity, metabolic syndrome, and type II diabetes. In some embodiments, the adipose tissue disorder is selected from the group consisting of obesity and related disorders selected from the group consisting of cancer, cellulitis, chronic renal failure, depression, diabetes, erectile dysfunction, fatty liver disease, gallbladder disease (e.g., gallstones), gastro-esophageal reflux disease, gout, heart disease (e.g., congestive heart failure, enlarged heart), hernia, high blood pressure, hypercholesterolemia, infection, infertility, lymph edema, osteoarthritis, pain, Pickwickian syndrome, pulmonary embolism, polycystic ovarian syndrome, ulcers, stroke, and urinary incontinence.

In some aspects, disclosed herein is a method of treating a lymph node disorder in a subject in need thereof, comprising administering to the subject an effective amount of a therapeutic agent for treating the lymph node disorder coupled to a lymph node microvessel endothelial cell targeting agent which binds to a protein expressed on the surface of a lymph node microvessel endothelial cell.

In some embodiments, the protein expressed on the surface of the lymph node microvessel endothelial cell is encoded by a gene exhibiting higher expression levels in lymph node venule endothelial cells compared to lymph node non-venule endothelial cells. In some embodiments, the gene is selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the gene is selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the protein expressed on the surface of the lymph node microvessel endothelial cell is encoded by a gene exhibiting higher expression levels in lymph node non-venule endothelial cells compared to lymph node venule endothelial cells. In some embodiments, the gene is selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the gene is selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

In some embodiments, the lymph node microvessel endothelial cell targeting agent delivers the coupled therapeutic agent to lymph node microvessel endothelial cells. In some embodiments, delivery of the therapeutic agent to the lymph node microvessel endothelial cell induces a local therapeutic effect in the lymph node microvessel endothelial cell, or a microvessel, tissue or organ surrounding the lymph node microvessel endothelial cell. In some embodiments, delivery of the therapeutic agent to the lymph node microvessel endothelial cell minimizes or eliminates an effect in the subject selected from the group consisting of a systemic effect, a toxic effect, an adverse effect, a side effect, and an undesired effect.

In some embodiments, the method further comprises modifying a dose of the therapeutic agent for local delivery to the lymph node microvessel endothelial cell. In some embodiments, the method further comprises selecting a subject who would likely benefit from delivery of the therapeutic agent to the subject's lymph node microvessel endothelial cells.

In some embodiments, the lymph node disorder is a disease characterized by lymphadenitis selected from the group consisting of (i) a cancer selected from the group consisting of leukemias, lymphomas, and metastatic cancer, (ii) a connective tissue disorder selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome, (iii) an infection selected from the group consisting of an upper respiratory tract infections, oropharyngeal infections, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the lymph node disorder is a lymph node disease selected from the group consisting of lymphoma, Hodgkins disease, tuberculosis, kikuchi disease, metastatic lymph node disease, lymphatic filiaris, mesenteric lymphadenitis, Castleman disease, lymphadenopathy, infiltration of the lymph nodes by metabolite-laden macrophages (e.g., lipid storage disorders such as Gaucher disease or Niemann-Pick disease, histiocytosis, cancer, lymphoid leukemia, splenomegaly, e.g., caused by sickle cell anemia, sarcoidosis, malaria, bacterial endocarditis, leukemia, pernicious anemia, Gaucher's disease, leishmaniasis, Hodgkin's disease, Banti's disease, hereditary spherocytosis, cysts, glandular fever, asplenia, hemangiomas, and hemangiosarcomas.

In some aspects, disclosed herein is a composition comprising a microvessel endothelial cell targeting agent which binds to a protein expressed on the surface of a microvessel endothelial cell.

In some embodiments, the composition further comprises an agent coupled to the microvessel endothelial cell targeting agent.

In some embodiments, the protein expressed on the surface of the microvessel endothelial cell is encoded by a gene that is preferentially expressed in microvessels. In some embodiments, the gene is selected from the group consisting of Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, Cd74. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some embodiments, the microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the microvessel endothelial cell targeting agent is coupled to the agent via a linker. In some embodiments, the microvessel endothelial cell targeting agent or the agent is coupled to a detectable reporter. In some embodiments, the microvessel endothelial cell targeting agent and/or the agent is encapsulated in a nanoparticle or microparticle. In some embodiments, the nanoparticle comprises a lipid nanoparticle or microparticle.

In some embodiments, administration of the composition to a subject delivers the agent to the subject's microvessel endothelial cells. In some embodiments, delivery of the agent to the subject's microvessel endothelial cells treats, prevents, or ameliorates a symptom of, a disease in the subject. In some embodiments, the disease is an inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some embodiments, the disease is a microvascular disease. In some embodiments, the microvascular disease is selected from the group consisting of venular disorders and non-venular disorders.

In some aspects, disclosed herein is a composition comprising a venule endothelial cell targeting agent which binds to a protein expressed on the surface of a venule endothelial cell.

In some embodiments, the composition further comprises an agent. In some embodiments, the agent is coupled to the venule endothelial cell targeting agent.

In some embodiments, the protein expressed on the surface of the venule endothelial cell is encoded by a gene exhibiting higher expression levels in venule endothelial cells compared to non-venule endothelial cells. In some embodiments, the gene is selected from the group consisting of Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1rl, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd5, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In some embodiments, the venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the venule endothelial cell targeting agent is coupled to the agent via a linker. In some embodiments, the venule endothelial cell targeting agent or the agent is coupled to a detectable reporter. In some embodiments, the venule endothelial cell targeting agent and/or the agent is encapsulated in a nanoparticle or microparticle. In some embodiments, the nanoparticle comprises a lipid nanoparticle or microparticle.

In some embodiments, administration of the composition to a subject delivers the agent to the subject's venule endothelial cells. In some embodiments, delivering the agent to the subject's venule endothelial cells treats, prevents, or ameliorates a symptom of, a disease in the subject. In some embodiments, the disease is an inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parasitic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some aspects, disclosed herein is a composition comprising a non-venule endothelial cell targeting agent which binds to a protein expressed on the surface of a non-venule endothelial cell.

In some embodiments, the composition further comprises an agent. In some embodiments, the agent is coupled to the non-venule endothelial cell targeting agent.

In some embodiments, the protein expressed on the surface of the non-venule endothelial cell is encoded by a gene exhibiting higher expression levels in non-venule endothelial cells compared to venule endothelial cells. In some embodiments, the gene is selected from the group consisting of Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. In some embodiments, the gene is selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some embodiments, the non-venule endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the non-venule endothelial cell targeting agent is coupled to the agent via a linker. In some embodiments, the non-venule endothelial cell targeting agent or the agent is coupled to a detectable reporter. In some embodiments, the non-venule endothelial cell targeting agent and/or the agent is encapsulated in a nanoparticle or microparticle. In some embodiments, the nanoparticle comprises a lipid nanoparticle or microparticle.

In some embodiments, administration of the composition to a subject delivers the agent to non-venule endothelial cells of the subject. In some embodiments, delivering the agent to non-venule endothelial cells of the subject treats, prevents, or ameliorates a symptom of, a disease in the subject. In some embodiments, the disease is a non-venular disease. In some embodiments, the non-venular disease is selected from the group consisting of small vessel coronary disease (e.g., cardiac syndrome X, microvascular dysfunction, non-obstructive coronary disease, and microvascular angina), thrombotic microangiopathy, microangiopathic haemolytic anaemia, microvascular occlusion, cutaneous diabetic microagniopathy, Susac's syndrome, cerebral microangiopathy, early diabetic microangiopathy, diabetic microangiopathy, glomerular microangiopathy, non-neoplastic nevus, pulmonary microangiopathy, pulmonary capillaritis (e.g., isolated pauci-immune pulmonary capillaritis), coronary microvascular disease, chronic microvascular diseases, small vessel ischemia, thrombotic thrombocytopenic purpura, arteriolosclerosis, and arterioloephosclerosis, teleangiectasia (e.g., hereditary hemorrhagic telangiectasia), and scleroderma.

In some aspects, disclosed herein is a composition comprising a skin microvessel endothelial cell targeting agent which binds to a protein expressed on the surface of a microvessel endothelial cell in skin. In some embodiments, the composition further comprises an agent. In some embodiments, the skin microvessel endothelial cell targeting agent is coupled to the agent.

In some embodiments, the protein expressed on the surface of the skin microvessel endothelial cell is encoded by a gene exhibiting higher expression levels in skin venule endothelial cells compared to skin non-venule endothelial cells. In some embodiments, the gene is selected from the group consisting of Nrp2, Gpr1, C630004H02Rik, Fndc1, 2310046K01Rik, Insr, and Slco2a1. In some embodiments, the gene is selected from the group consisting of Nrp2, Htr2b, Mr1, Lifr, Anxa1, Lphn2, Vamp5, Olr1, Eps8, Slco2b1, and Slco2a1.

In some embodiments, the protein expressed on the surface of the skin microvessel endothelial cell is encoded by a gene exhibiting higher expression levels in skin non-venule endothelial cells compared to skin venule endothelial cells. In some embodiments, the gene is selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the gene is selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

In some embodiments, the skin microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the skin microvessel endothelial cell targeting agent is coupled to the agent via a linker. In some embodiments, the skin microvessel endothelial cell targeting agent or agent is coupled to a detectable reporter.

In some embodiments, administering the composition to a subject delivers the agent to the subject's skin microvessel endothelial cells. In some embodiments, delivering the agent to skin microvessel endothelial cells of the subject treats, prevents, or ameliorates a symptom of, a skin disease in the subject. In some embodiments, the skin disease is selected from the group consisting of acne, alopecia (e.g., alopecia areata, alopecia totalis, alopecia universalis, traction alopecia), angioma, athlete's foot, basal cell carcinoma, bed sore, Behcet's Disease, blepharitis, boil, calluses and corns, canker sore, carbuncles, candidiasis (e.g., oral (oral thrush), vaginal (candidal vulvovaginitis), penile (candidal balanitis), in the diaper area (diaper rash), in the skin folds (candidal intertrigo), cellulitis, cold sores, creeping eruption, dandruff, dermatitis (eczema) (e.g., atopic dermatitis, contact dermatitis, seborrhoeic dermatitis, cradle cap, nummular dermatitis, stasis dermatitis, perioral dermatitis (muzzle rash), dermatitis herpetiformis), dermatofibroma, Bowen's Disease, bullous pemphigoid, ecthima, eczema, epidermolysis bullosa (e.g., simplex, junctional, dystrophic, hemidesmosomal), erythrasma, erysipelas, folliculitis, friction blisters, herpes (e.g., HHV1 i.e., cold sores, HHV2 i.e., genital herpes, HHV3, e.g., chickenpox, shingles, HHV6, HHV7, e.g., roseola infantum, sixth disease, HHV8, i.e., Kaposi's sarcoma herpesvirus), hidradenitis suppurativa, hives, hyperhidrosis, ichthyosis, impetigo, jock itch, Kaposi's sarcoma, keloid, keratoacanthoma, keratosis (e.g., actinic (solar) keratosis, keratosis pilaris, keratosis follicularis (Darrier's disease), seborrheic, and hyperkeratosis), lice infection, lichen planus, lichen simplex chronicus, lipoma, lymphadenitis, malignant melanoma, melisma, miliaria, molluscum contagiosum, Paget's disease of the nipple, pediculosis, pemphigus, photoallergy, photosensitivity, *pityriasis rosea, pityriasis rubra* pilaris, psoriasis, Raynaud's disease, ring worm, Raynaud's disease, rosacea, Saint Anthony's fire, scabies, scleroderma, sebaceous cyst, shingles, skin cancer, skin tags, spider veins (telangiectasia), squamous cell carcinoma, tick bite, tinea: (barbae, capitis, corporis, cruris (Jock Itch), pedis unguium, *versicolor*), trichomycosis, varicose veins, vitiligo, warts (e.g., common, planar, genital).

In some embodiments, the skin disease is a skin inflammatory disease. In some embodiments, the skin inflammatory disease is selected from the group consisting of acne, dermatitis, eczema, oily skin, rosacea, cutaneous lymphoma and urticaria. In some embodiments, the dermatitis is selected from the group consisting of atopic dermatitis, psoriasis and contact dermatitis.

In some aspects, disclosed herein is a composition comprising an adipose tissue microvessel endothelial cell targeting agent which binds to a protein expressed on the surface of a microvessel endothelial cell in adipose tissue.

In some embodiments, the composition further comprises an agent. In some embodiments, the adipose tissue microvessel endothelial cell targeting agent is coupled to the agent.

In some embodiments, the protein expressed on the surface of the adipose tissue microvessel endothelial cell is encoded by a gene exhibiting higher expression levels in adipose tissue venule endothelial cells compared to adipose tissue non-venule endothelial cells. In some embodiments, the gene is selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the gene is selected from the group consisting of Il1rl1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the protein expressed on the surface of the adipose tissue microvessel endothelial cell is encoded by a gene exhibiting higher expression levels in adipose tissue non-venule endothelial cells compared to adipose tissue venule endothelial cells. In some embodiments, the gene is selected from the group consisting of Adora2a, H2-Ab1, Hspg2, Gpr81, Kcna5, Jam3, and Gpc4. In some embodiments, the gene is selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some embodiments, the adipose tissue microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the adipose tissue microvessel endothelial cell targeting agent is coupled to the agent via a linker. In some embodiments, the adipose tissue microvessel endothelial cell targeting agent or agent is coupled to a detectable reporter.

In some embodiments, administration of the composition to a subject delivers the agent to the subject's adipose tissue microvessel endothelial cells. In some embodiments, delivering the agent to the subject's adipose tissue microvessel endothelial cells treats, prevents, or ameliorates a symptom of, an adipose tissue disease. In some embodiments, the adipose tissue disease is selected from the group consisting of obesity and related disorders selected from the group consisting of cancer, cellulitis, chronic renal failure, depression, diabetes, erectile dysfunction, fatty liver disease, gallbladder disease (e.g., gallstones), gastro-esophageal reflux disease, gout, heart disease (e.g., congestive heart failure, enlarged heart), hernia, high blood pressure, hypercholesterolemia, infection, infertility, lymph edema, osteoarthritis, pain, Pickwickian syndrome, pulmonary embolism, polycystic ovarian syndrome, ulcers, stroke, and urinary incontinence.

In some embodiments, the adipose tissue disease is a disease characterized by inflammation in the subject's visceral fat. In some embodiments, the disease is selected from the group consisting of cancer, CVHD, fibrosis, hypertension, lypodystrophy, obesity, metabolic syndrome, and type II diabetes.

In some aspects, disclosed herein is a composition comprising a lymph node microvessel endothelial cell targeting agent which binds to a protein expressed on the surface of a microvessel endothelial cell in the lymph nodes. In some embodiments, the composition further comprises an agent.

In some embodiments, the lymph node microvessel endothelial cell targeting agent is coupled to the agent.

In some embodiments, the protein expressed on the surface of the lymph node microvessel endothelial cell is encoded by a gene exhibiting higher expression levels in lymph node venule endothelial cells compared to lymph node non-venule endothelial cells. In some embodiments, the gene is selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg.

In some embodiments, the protein expressed on the surface of the lymph node microvessel endothelial cell is encoded by a gene exhibiting higher expression levels in lymph node non-venule endothelial cells compared to lymph node venule endothelial cells. In some embodiments, the gene is selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the gene is selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

In some embodiments, the lymph node microvessel endothelial cell targeting agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, the agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent is selected from a therapeutic agent, a diagnostic agent, an imaging agent, a multi-purpose agent, and combinations thereof. In some embodiments, the agent comprises a therapeutic agent. In some embodiments, the agent comprises a cytotoxic agent. In some embodiments, the cytotoxic agent is selected from the group consisting of taxol; a nitrogen mustard selected from the group consisting of mechlorethamine, cyclophosphamide, melphalan, uracil mustard and chlorambucil; thiotepa; busulfan; a nitrosourea selected from the group consisting of carmustine, lomustine, semustine and streptozocin; dacarbazine; methotrexate; fluorouracil, cytarabine, azaribine; a purine analogs selected from the group consisting of mercaptopurine and thioguanine; a vinca alkaloids selected from the group consisting of vinblastine and vincristine; an antibiotic selected from the group consisting of dactinomycin, daunorubicin, doxorubicin, bleomycin, mithramycin and mitomycin; L-asparaginase; cisplatin; hydroxyurea; procarbazine; anti-virals; vaccines; and photodynamic dyes. In some embodiments, the agent comprises a chemotherapeutic agent. In some embodiments, the chemotherapeutic agent is selected from the group consisting of vinblastine, doxorubicin, bleomycin, methotrexate, 5-fluorouracil, 6-thioguanine, cytarabine, cyclophosphamide and cisplatinum. In some embodiments, the agent comprises a diagnostic agent. In some embodiments, the agent comprises an imaging agent. In some embodiments, the lymph node microvessel endothelial cell targeting agent is coupled to the agent via a linker. In some embodiments, the microvessel endothelial cell targeting agent is coupled to a detectable reporter.

In some embodiments, administration of the composition to a subject delivers the agent to the subject's lymph node microvessel endothelial cells. In some embodiments, delivering an agent to lymph node microvessel endothelial cells of the subject treats, prevents, or ameliorates a symptom of, a lymph node disease.

In some embodiments, the lymph node disease is selected from the group consisting of lymphoma, Hodgkins disease, tuberculosis, kikuchi disease, metastatic lymph node disease, lymphatic filiaris, mesenteric lymphadenitis, Castleman disease, lymphadenopathy, infiltration of the lymph nodes by metabolite-laden macrophages (e.g., lipid storage disorders such as Gaucher disease or Niemann-Pick disease, histiocytosis, cancer, lymphoid leukemia, splenomegaly, e.g., caused by sickle cell anemia, sarcoidosis, malaria, bacterial endocarditis, leukemia, pernicious anemia, Gaucher's disease, leishmaniasis, Hodgkin's disease, Banti's disease, hereditary spherocytosis, cysts, glandular fever, asplenia, hemangiomas, and hemangiosarcomas. In some embodiments, delivering an agent to lymph node microvessel endothelial cells of the subject treats, prevents, or ameliorates a symptom of, a disease characterized by lymphadenopathy or lymphadenitis.

In some embodiments, the disease is selected from the group consisting of cancer, a connective tissue disorder, and infection. In some embodiments, the cancer is selected from the group consisting of leukemias, lymphomas, and metastatic cancer. In some embodiments, the infection is selected from the group consisting of a bacterial infection and a viral infection. In some embodiments, the infection is selected from the group consisting of an upper respiratory tract infection, an oropharyngeal infection, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess. In some embodiments, the connective tissue disorder is selected from the group consisting of systemic lupus erythematosus (SLE), sarcoidosis, Kawasaki disease, juvenile idiopathic arthritis, Kikuchi lymphadenopathy, rheumatoid arthritis, and Sjögren syndrome.

In some aspects, disclosed herein is a method of identifying a candidate microvessel endothelial cell targeting agent which binds to a protein expressed on the surface of a microvessel endothelial cell, comprising: (a) contacting a protein expressed on the surface of a microvessel endothelial cell with a test agent; and (b) assessing the ability of the test agent to bind the protein expressed on the surface of the microvessel endothelial cell, wherein a test agent that binds to the protein expressed on the surface of the microvessel endothelial cell is a candidate microvessel endothelial cell targeting agent.

In some aspects, disclosed herein is a method of identifying a candidate microvessel endothelial cell targeting agent which binds to a protein expressed on the surface of a microvessel endothelial cell and delivers an agent to a microvessel endothelial cell in a subject, comprising: (a) administering to a subject a test microvessel endothelial cell targeting agent which binds to a protein expressed on the surface of a microvessel endothelial cell coupled to an agent; and (b) assessing the ability of the microvessel endothelial cell targeting agent to deliver the agent to a microvessel endothelial cell in the subject, wherein a test agent that delivers the agent to a microvessel endothelial cell in the subject is a candidate microvessel endothelial cell targeting agent.

In some embodiments, the protein expressed on the surface of the microvessel endothelial cell is encoded by a gene that is preferentially expressed in microvessels.

In some embodiments, the gene is selected from the group consisting of Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, administration comprises intravenous infusion.

In some embodiments, the agent comprises a fluorescent component.

In some embodiments, the agent is a fluorescent reagent.

In some embodiments, assessing the ability of the microvessel endothelial cell targeting agent to deliver the agent to a microvessel endothelial cell comprises in situ imaging of the test agent or the agent. In some embodiments, assessing the ability of the microvessel endothelial cell targeting agent to deliver the agent to a microvessel endothelial cell comprises analyzing internalization of the test agent or the agent in a microvessel, tissue, or organ surrounding the microvessel endothelial cell. In some embodiments, assessing the ability of the microvessel endothelial cell targeting agent to deliver the agent to a microvessel endothelial cell comprises analyzing accumulation of the test agent or the agent in a microvessel, tissue, or organ surrounding the microvessel endothelial cell.

In some aspects, disclosed herein is a method of identifying a candidate venule endothelial cell targeting agent which binds to a protein expressed on the surface of a venule endothelial cell, comprising: (a) contacting a protein expressed on the surface of a venule endothelial cell with a test agent; and (b) assessing the ability of the test agent to bind the protein expressed on the surface of the venule endothelial cell, wherein a test agent that binds to the protein expressed on the surface of the venule endothelial cell is a candidate venule endothelial cell targeting agent.

In some aspects, disclosed herein is a method of identifying a candidate venule endothelial cell targeting agent which binds to a protein expressed on the surface of a venule endothelial cell and delivers an agent to a venule endothelial cell in a subject, comprising: (a) administering to a subject a test venule endothelial cell targeting agent which binds to a protein expressed on the surface of a venule endothelial cell coupled to an agent; and (b) assessing the ability of the venule endothelial cell targeting agent to deliver the agent to a venule endothelial cell in the subject, wherein a test agent that delivers the agent to a venule endothelial cell in the subject is a candidate venule endothelial cell targeting agent.

In some embodiments, the protein expressed on the surface of the venule endothelial cell is encoded by a gene exhibiting higher expression levels in venule endothelial cells compared to non-venule endothelial cells. In some embodiments, the gene is selected from the group consisting of Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. In some embodiments, the gene is selected from the group consisting of Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, administration comprises intravenous infusion.

In some embodiments, the agent comprises a fluorescent component. In some embodiments, the agent is a fluorescent reagent.

In some embodiments, assessing the ability of the venule endothelial cell targeting agent to deliver the agent to a venule endothelial cell comprises in situ imaging of the test agent or the agent. In some embodiments, assessing the ability of the venule endothelial cell targeting agent to deliver the agent to a venule endothelial cell comprises analyzing internalization of the test agent or the agent in a venule, tissue, or organ surrounding the venule endothelial cell. In some embodiments, assessing the ability of the venule endothelial cell targeting agent to deliver the agent to a venule endothelial cell comprises analyzing accumulation of the test agent or the agent in a venule, tissue, or organ surrounding the venule endothelial cell.

In some aspects, disclosed herein is a method of identifying a candidate non-venule endothelial cell targeting agent which binds to a protein expressed on the surface of a non-venule endothelial cell, comprising: (a) contacting a protein expressed on the surface of a non-venule endothelial cell with a test agent; and (b) assessing the ability of the test agent to bind the protein expressed on the surface of the non-venule endothelial cell, wherein a test agent that binds to the protein expressed on the surface of the non-venule endothelial cell is a candidate non-venule endothelial cell targeting agent.

In some aspects, disclosed herein is a method of identifying a candidate microvessel endothelial cell targeting agent which binds to a protein expressed on the surface of a non-venule endothelial cell and delivers an agent to a non-venule endothelial cell in a subject, comprising: (a) administering to a subject a test non-venule endothelial cell targeting agent which binds to a protein expressed on the surface of a non-venule endothelial cell coupled to an agent; and (b) assessing the ability of the non-venule endothelial cell targeting agent to deliver the agent to a non-venule endothelial cell in the subject, wherein a test agent that delivers the agent to a non-venule endothelial cell in the subject is a candidate microvessel endothelial cell targeting agent.

In some embodiments, the protein expressed on the surface of the non-venule endothelial cell is encoded by a gene exhibiting higher expression levels in non-venule endothelial cells compared to venule endothelial cells. In some embodiments, the gene is selected from the group consisting of Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. In some embodiments, the gene is selected from the group consisting of Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, administration comprises intravenous infusion.

In some embodiments, the agent comprises a fluorescent component. In some embodiments, the agent is a fluorescent reagent.

In some embodiments, assessing the ability of the non-venule endothelial cell targeting agent to deliver the agent to a non-venule endothelial cell comprises in situ imaging of the test agent or the agent. In some embodiments, assessing the ability of the non-venule endothelial cell targeting agent to deliver the agent to a non-venule endothelial cell comprises analyzing internalization of the test agent or the agent in a non-venule, tissue, or organ surrounding the non-venule endothelial cell. In some embodiments, assessing the ability of the non-venule endothelial cell targeting agent to deliver the agent to a non-venule endothelial cell comprises analyzing accumulation of the test agent or the agent in a non-venule, tissue, or organ surrounding the microvessel endothelial cell.

In some aspects, disclosed herein is a method of identifying a candidate skin microvessel endothelial cell targeting agent which binds to a protein expressed on the surface of a skin microvessel endothelial cell, comprising: (a) contacting a protein expressed on the surface of a skin microvessel endothelial cell with a test agent; and (b) assessing the ability of the test agent to bind the protein expressed on the surface of the skin microvessel endothelial cell, wherein a test agent that binds to the protein expressed on the surface of the skin microvessel endothelial cell is a candidate skin microvessel endothelial cell targeting agent.

In some aspects, disclosed herein is a method of identifying a candidate skin microvessel endothelial cell targeting agent which binds to a protein expressed on the surface of a skin microvessel endothelial cell and delivers an agent to a skin microvessel endothelial cell in a subject, comprising: (a) administering to a subject a test skin microvessel endothelial cell targeting agent which binds to a protein expressed on the surface of a skin microvessel endothelial cell coupled to an agent; and (b) assessing the ability of the test skin microvessel endothelial cell targeting agent to deliver the agent to a skin microvessel endothelial cell in the subject, wherein a test skin microvessel endothelial cell targeting agent that delivers the agent to a skin microvessel endothelial cell in the subject is a candidate skin microvessel endothelial cell targeting agent.

In some embodiments, the protein expressed on the surface of the skin microvessel endothelial cell is encoded by a gene exhibiting higher expression levels in skin venule endothelial cells compared to skin non-venule endothelial cells. In some embodiments, the gene is selected from the group consisting of Nrp2, Gpr1, C630004H02Rik, Fndc1, 2310046K01Rik, Insr, and Slco2a1. In some embodiments, the gene is selected from the group consisting of Nrp2, Htr2b, Mr1, Lifr, Anxa1, Lphn2, Vamp5, Olr1, Eps8, Slco2b1, and Slco2a1.

In some embodiments, the protein expressed on the surface of the skin microvessel endothelial cell is encoded by a gene exhibiting higher expression levels in skin non-venule endothelial cells compared to skin venule endothelial cells. In some embodiments, the gene is selected from the group consisting of Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, the gene is selected from the group consisting of Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, administration comprises intravenous infusion.

In some embodiments, the agent comprises a fluorescent component. In some embodiments, the agent is a fluorescent reagent.

In some embodiments, assessing the ability of the skin microvessel endothelial cell targeting agent to deliver the agent to a skin microvessel endothelial cell comprises in situ imaging of the test agent or the agent. In some embodiments, assessing the ability of the skin microvessel endothelial cell targeting agent to deliver the agent to a skin microvessel endothelial cell comprises analyzing internalization of the test agent or the agent in a microvessel, tissue, or organ surrounding the skin microvessel endothelial cell. In some embodiments, assessing the ability of the skin microvessel endothelial cell targeting agent to deliver the agent to a skin microvessel endothelial cell comprises analyzing accumulation of the test agent or the agent in a microvessel, tissue, or organ surrounding the skin microvessel endothelial cell.

In some aspects, disclosed herein is a method of identifying a candidate adipose tissue microvessel endothelial cell targeting agent which binds to a protein expressed on the surface of an adipose tissue microvessel endothelial cell, comprising: (a) contacting a protein expressed on the surface of an adipose tissue microvessel endothelial cell with a test agent; and (b) assessing the ability of the test agent to bind the protein expressed on the surface of the adipose tissue microvessel endothelial cell, wherein a test agent that binds to the protein expressed on the surface of the adipose tissue microvessel endothelial cell is a candidate adipose tissue microvessel endothelial cell targeting agent.

In some embodiments, disclosed herein is a method of identifying a candidate adipose tissue microvessel endothelial cell targeting agent which binds to a protein expressed on the surface of an adipose tissue microvessel endothelial cell and delivers an agent to an adipose tissue microvessel endothelial cell in a subject, comprising: (a) administering to a subject a test adipose tissue microvessel endothelial cell targeting agent which binds to a protein expressed on the surface of an adipose tissue microvessel endothelial cell coupled to an agent; and (b) assessing the ability of the test adipose tissue microvessel endothelial cell targeting agent to deliver the agent to an adipose tissue microvessel endothelial cell in the subject, wherein a test adipose tissue microvessel endothelial cell targeting agent that delivers the agent to an adipose tissue microvessel endothelial cell in the subject is a candidate adipose tissue microvessel endothelial cell targeting agent.

In some embodiments, the protein expressed on the surface of the adipose tissue microvessel endothelial cell is encoded by a gene exhibiting higher expression levels in adipose tissue venule endothelial cells compared to adipose tissue non-venule endothelial cells. In some embodiments, the gene is selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, the gene is selected from the group consisting of Il1rl1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the protein expressed on the surface of the adipose tissue microvessel endothelial cell is encoded by a gene exhibiting higher expression levels in adipose tissue non-venule endothelial cells compared to adipose tissue venule endothelial cells. In some embodiments, the gene is selected from the group consisting of Adora2a, H2-Ab1, Hspg2, Gpr81, Kcna5, Jam3, and Gpc4. In some embodiments, the gene is selected from the group consisting of Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some embodiments, the test agent is selected from the group consisting of small organic or inorganic molecules;

saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, administration comprises intravenous infusion.

In some embodiments, the agent comprises a fluorescent component. In some embodiments, the agent is a fluorescent reagent.

In some embodiments, assessing the ability of the adipose tissue microvessel endothelial cell targeting agent to deliver the agent to an adipose tissue microvessel endothelial cell comprises in situ imaging of the test agent or the agent.

In some embodiments, assessing the ability of the adipose tissue microvessel endothelial cell targeting agent to deliver the agent to an adipose tissue microvessel endothelial cell comprises analyzing internalization of the test agent or the agent in a microvessel, tissue, or organ surrounding the adipose tissue microvessel endothelial cell. In some embodiments, assessing the ability of the adipose tissue microvessel endothelial cell targeting agent to deliver the agent to an adipose tissue microvessel endothelial cell comprises analyzing accumulation of the test agent or the agent in a microvessel, tissue, or organ surrounding the adipose tissue microvessel endothelial cell.

In some aspects, disclosed herein is a method of identifying a candidate lymph node microvessel endothelial cell targeting agent which binds to a protein expressed on the surface of a lymph node microvessel endothelial cell, comprising: (a) contacting a protein expressed on the surface of a lymph node microvessel endothelial cell with a test agent; and (b) assessing the ability of the test agent to bind the protein expressed on the surface of the lymph node microvessel endothelial cell, wherein a test agent that binds to the protein expressed on the surface of the lymph node microvessel endothelial cell is a candidate lymph node microvessel endothelial cell targeting agent.

In some aspects, disclosed herein is a method of identifying a candidate lymph node microvessel endothelial cell targeting agent which binds to a protein expressed on the surface of a lymph node microvessel endothelial cell and delivers an agent to a lymph node microvessel endothelial cell in a subject, comprising: (a) administering to a subject a test lymph node microvessel endothelial cell targeting agent which binds to a protein expressed on the surface of a lymph node microvessel endothelial cell coupled to an agent; and (b) assessing the ability of the test lymph node microvessel endothelial cell targeting agent to deliver the agent to a lymph node microvessel endothelial cell in the subject, wherein a test lymph node microvessel endothelial cell targeting agent that delivers the agent to a lymph node microvessel endothelial cell in the subject is a candidate lymph node microvessel endothelial cell targeting agent.

In some embodiments, the protein expressed on the surface of the lymph node microvessel endothelial cell is encoded by a gene exhibiting higher expression levels in lymph node venule endothelial cells compared to lymph node non-venule endothelial cells. In some embodiments, the gene is selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. In some embodiments, the gene is selected from the group consisting of Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the protein expressed on the surface of the lymph node microvessel endothelial cell is encoded by a gene exhibiting higher expression levels in lymph node non-venule endothelial cells compared to lymph node venule endothelial cells. In some embodiments, the gene is selected from the group consisting of Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, the gene is selected from the group consisting of Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

In some embodiments, administration comprises intravenous infusion.

In some embodiments, the agent comprises a fluorescent component. In some embodiments, the agent is a fluorescent reagent.

In some embodiments, assessing the ability of the lymph node microvessel endothelial cell targeting agent to deliver the agent to a lymph node microvessel endothelial cell comprises in situ imaging of the test agent or the agent. In some embodiments, assessing the ability of the lymph node microvessel endothelial cell targeting agent to deliver the agent to a lymph node microvessel endothelial cell comprises analyzing internalization of the test agent or the agent in a microvessel, tissue, or organ surrounding the lymph node microvessel endothelial cell. In some embodiments, assessing the ability of the lymph node microvessel endothelial cell targeting agent to deliver the agent to a lymph node microvessel endothelial cell comprises analyzing accumulation of the test agent or the agent in a microvessel, tissue, or organ surrounding the lymph node microvessel endothelial cell.

In some aspects, the disclosure provides a method of delivering an agent to a venule endothelial cell in a subject, comprising administering to the subject a venule endothelial cell targeting agent which binds to il6st on the surface of a venule endothelial cell. In some embodiments, the venule endothelial cell targeting agent causes an effect in the venule endothelial cell, or a venule, tissue or organ adjacent to the venule endothelial cell. In some embodiments, the venule endothelial cell targeting agent is coupled to an agent which causes an effect in the venule endothelial cell, or venule, tissue or organ adjacent to the venule endothelial cell. In some embodiments, the venule endothelial cell targeting agent and/or agent is internalized into or transported across the endothelial cells lining the venule. In some embodiments, internalization of the venule endothelial cell targeting agent and/or agent into the endothelial cells lining the microvessel causes the venule endothelial cell targeting agent and/or agent to accumulate in a venule, tissue or organ adjacent to the venule endothelial cell. In some embodiments, the venule endothelial cell targeting agent and/or agent does not accumulate in non-target venules, tissues, or organs. In some embodiments, the venule endothelial cell targeting agent and/or agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the venule endothelial cell targeting agent and/or agent comprises an aptide. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the venule endothelial cell targeting agent is coupled to the agent via a linker. In some embodiments, the venule endothelial cell targeting agent or the agent is coupled to a detectable reporter. In some embodiments, the venule endothelial cell targeting agent and/or the agent is encapsulated in a nanoparticle or microparticle. In some embodiments, the nanoparticle comprises a lipid nanoparticle or microparticle. In some embodiments, the nanoparticle comprises a polymeric nanoparticle constructed from low molecular weight polyamines and lipids. In some embodiments, delivering an agent to venule endothelial cells of the subject treats, prevents, or ameliorates a symptom of, a disease in the subject. In some embodiments, the disease is an inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some aspects, the disclosure provides a method of delivering an agent to a venule endothelial cell in skin, comprising administering to a subject a skin venule endothelial cell targeting agent which binds to a il6st on the surface of a venule endothelial cell in skin. In some embodiments, the skin venule endothelial cell targeting agent causes an effect in the skin venule endothelial cell, or venule, tissue, or organ adjacent to the skin venule endothelial cell. In some embodiments, the skin venule endothelial cell targeting agent is coupled to an agent which causes an effect in the skin venule endothelial cell, or venule, tissue, or organ adjacent to the skin venule endothelial cell. In some embodiments, the skin venule endothelial cell targeting agent and/or agent is internalized into or transported across the endothelial cells lining a venule in the subject's skin. In some embodiments, internalization of the skin venule endothelial cell targeting agent into the endothelial cells lining the venule in the subject's skin causes the skin venule endothelial cell targeting agent and/or agent to accumulate in the subject's skin. In some embodiments, the skin venule endothelial cell targeting agent and/or agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the skin venule endothelial cell targeting agent and/or agent comprises an aptide. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the skin venule endothelial cell targeting agent is coupled to the agent via a linker. In some embodiments, the skin venule endothelial cell targeting agent or agent is coupled to a detectable reporter. In some embodiments, the skin venule endothelial cell targeting agent and/or agent are encapsulated in nanoparticles or microparticles. In some embodiments, the nanoparticle comprises a polymeric nanoparticle constructed from low molecular weight polyamines and lipids. In some embodiments, delivering an agent to skin venule endothelial cells of the subject treats, prevents, or ameliorates a symptom of, a skin disease. In some embodiments, the skin disease is selected from the group consisting of acne, alopecia (e.g., alopecia areata, alopecia totalis, alopecia universalis, traction alopecia), angioma, athlete's foot, basal cell carcinoma, bed sore, Behcet's Disease, blepharitis, boil, calluses and corns, canker sore, carbuncles, candidiasis (e.g., oral (oral thrush), vaginal (candidal vulvovaginitis), penile (candidal balanitis), in the diaper area (diaper rash), in the skin folds (candidal intertrigo), cellulitis, cold sores, creeping eruption, dandruff, dermatitis (eczema) (e.g., atopic dermatitis, contact dermatitis, seborrhoeic dermatitis, cradle cap, nummular dermatitis, stasis dermatitis, perioral dermatitis (muzzle rash), dermatitis herpetiformis), dermatofibroma, Bowen's Disease, bullous pemphigoid, echtima, eczema, epidermolysis bullosa (e.g., simplex, junctional, dystrophic, hemidesmosomal), erythrasma, erysipelas, folliculitis, friction blisters, herpes (e.g., HHV1 i.e., cold sores, HHV2 i.e., genital herpes, HHV3, e.g., chickenpox, shingles, HHV6, HHV7, e.g., roseola infantum, sixth disease, HHV8, i.e., Kaposi's sarcoma herpesvirus), hidradenitis suppurativa, hives, hyperhidrosis, ichthyosis, impetigo, jock itch, Kaposi's sarcoma, keloid, keratoacanthoma, keratosis (e.g., actinic (solar) keratosis, keratosis pilaris, keratosis follicularis (Darrier's disease), seborrheic, and hyperkeratosis), lice infection, lichen planus, lichen simplex chronicus, lipoma, lymphadenitis, malignant melanoma, melisma, miliaria, molluscum contagiosum, Paget's disease of the nipple, pediculosis, pemphigus, photoallergy, photosensitivity, *pityriasis rosea, pityriasis rubra* pilaris, psoriasis, Raynaud's disease, ring worm, Raynaud's disease, rosacea, Saint Anthony's fire, scabies, scleroderma, sebaceous cyst, shingles, skin cancer, skin tags, spider veins (telangiectasia), squamous cell carcinoma, tick bite, tinea: (barbae, capitis, corporis, cruris (Jock Itch), pedis unguium, *versicolor*), trichomycosis, varicose veins, vitiligo, warts (e.g., common, planar, genital). In some embodiments, the skin disease is a skin inflammatory disease. In some embodiments, the skin inflammatory disease is selected from the group consisting of acne, dermatitis, eczema, oily skin, rosacea, cutaneous lymphoma and urticaria. In some embodiments, the dermatitis is selected from the group consisting of atopic dermatitis, psoriasis and contact dermatitis.

In some aspects, the disclosure provides a method of delivering an agent to a venule endothelial cell in adipose tissue, comprising administering to a subject an adipose tissue venule endothelial cell targeting agent which binds to il6st on the surface of a venule endothelial cell in adipose tissue. In some embodiments, the adipose tissue venule endothelial cell targeting agent causes an effect in the adipose tissue venule endothelial cell, or venule, tissue, or organ adjacent to the adipose tissue venule endothelial cell. In some embodiments, the adipose tissue venule endothelial cell targeting agent is coupled to an agent which causes an effect in the adipose tissue venule endothelial cell, or venule, tissue, or organ adjacent to the adipose tissue venule endothelial cell. In some embodiments, the adipose tissue venule endothelial cell targeting agent and/or agent is internalized into or transported across the endothelial cells lining a venule in the subject's adipose tissue. In some embodiments, internalization of the adipose tissue venule endothelial cell targeting agent into the endothelial cells lining the venule in the subject's adipose tissue causes the adipose tissue venule endothelial cell targeting agent and/or agent to accumulate in subject's adipose tissue. In some embodiments, the adipose tissue venule endothelial cell targeting agent and/or agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the agent comprises a therapeutic agent. In some embodiments, the adipose tissue venule endothelial cell targeting agent and/or agent comprises an aptide. In some embodiments, the agent comprises an anti-inflammatory agent. In some embodiments, the agent comprises a diagnostic agent. In some embodiments, the agent comprises an imaging agent. In some embodiments, the adipose tissue venule endothelial cell targeting agent is coupled to the agent via a linker. In some embodiments, the adipose tissue venule endothelial cell targeting agent or agent is coupled to a detectable reporter. In some embodiments, the adipose tissue venule endothelial cell targeting agent and/or agent are encapsulated in nanoparticles or microparticles. In some embodiments, the nanoparticle comprises a polymeric nanoparticle constructed from low molecular weight polyamines and lipids. In some embodiments, targeting an agent to the subject's adipose tissue venule endothelial cells treats, prevents, or ameliorates a symptom of, an adipose tissue disease. In some embodiments, the adipose tissue disease is selected from the group consisting of obesity and related disorders selected from the group consisting of cancer, cellulitis, chronic renal failure, depression, diabetes, erectile dysfunction, fatty liver disease, gallbladder disease (e.g., gallstones), gastro-esophageal reflux disease, gout, heart disease (e.g., congestive heart failure, enlarged heart), hernia, high blood pressure, hypercholesterolemia, infection, infertility, lymph edema, osteoarthritis, pain, Pickwickian syndrome, pulmonary embolism, polycystic ovarian syndrome, ulcers, stroke, and urinary incontinence. In some embodiments, targeting an agent to the subject's adipose tissue venule endothelial cells treats, prevents, or ameliorates a symptom of, a disease characterized by inflammation in the subject's visceral fat. In some embodiments, the disease is selected from the group consisting of cancer, CVHD, fibrosis, hypertension, lypodystrophy, obesity, metabolic syndrome, and type II diabetes.

In some aspects, the disclosure provides a method of treating a venule endothelial cell-associated disorder in a subject in need thereof, comprising administering to the subject an effective amount of a therapeutic agent for treating the venule endothelial cell-associated disorder coupled to a venule endothelial cell targeting agent which binds to il6st on the surface of a venule endothelial cell. In some embodiments, the venule endothelial cell targeting agent delivers the coupled therapeutic agent to venule endothelial cells. In some embodiments, delivery of the therapeutic agent to the venule endothelial cell induces a local therapeutic effect in the venule endothelial cell, or a venule, tissue or organ surrounding the venule endothelial cell. In some embodiments, delivery of the therapeutic agent to the venule endothelial cell minimizes or eliminates an effect in the subject selected from the group consisting of a systemic effect, a toxic effect, an adverse effect, a side effect, and an undesired effect. In some embodiments, the method includes modifying a dose of the therapeutic agent for local delivery to the venule endothelial cell. In some embodiments, the method includes selecting a subject who would likely benefit from delivery of the therapeutic agent to the subject's venule endothelial cells. In some embodiments, the venule endothelial cell-associated disorder is an inflammatory disease selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease. In some embodiments, the venule endothelial cell-associated disorder is a venular disorder selected from the group consisting of high endothelial venules, rheumatoid arthritis, chronic inflammation associated with high endothelial venules, inflammatory bowel diseases, venule occlusion, small vessel disease, cardiovascular disease associated with small vessel disease, age-related small vessel diseases, hypertension-related small vessel diseases, and cerebral amyloid angiopathy.

In some aspects, the disclosure provides a method of treating a skin disorder in a subject in need thereof, comprising administering to the subject an effective amount of a therapeutic agent for treating the skin disorder coupled to a skin venule endothelial cell targeting agent which binds to il6st on the surface of a skin venule endothelial cell. In some embodiments, the skin venule endothelial cell targeting agent delivers the coupled therapeutic agent to skin venule endothelial cells. In some embodiments, delivery of the therapeutic agent to the skin venule endothelial cell induces a local therapeutic effect in the skin venule endothelial cell, or a venule, tissue or organ surrounding the skin venule endothelial cell. In some embodiments, delivery of the therapeutic agent to the skin venule endothelial cell minimizes or eliminates an effect in the subject selected from the group consisting of a systemic effect, a toxic effect, an adverse effect, a side effect, and an undesired effect. In some embodiments, the method includes modifying a dose of the therapeutic agent for local delivery to the skin venule endothelial cell. In some embodiments, the method includes selecting a subject who would likely benefit from delivery of the therapeutic agent to the subject's skin venule endothelial cells. In some embodiments, the skin disorder is a skin inflammatory disease selected from the group consisting of acne, dermatitis, eczema, oily skin, rosacea, cutaneous lymphoma and urticaria. In some embodiments, the skin disorder is selected from the group consisting of acne, alopecia (e.g., alopecia areata, alopecia totalis, alopecia universalis, traction alopecia), angioma, athlete's foot, basal cell carcinoma, bed sore, Behcet's Disease, blepharitis, boil, calluses and corns, canker sore, carbuncles, candidiasis (e.g., oral (oral thrush), vaginal (candidal vulvovaginitis), penile (candidal balanitis), in the diaper area (diaper rash), in the skin folds (candidal intertrigo), cellulitis, cold sores, creeping eruption, dandruff, dermatitis (eczema) (e.g., atopic dermatitis, contact dermatitis, seborrhoeic dermatitis, cradle cap, nummular dermatitis, stasis dermatitis, perioral dermatitis (muzzle rash), dermatitis herpetiformis), dermatofibroma, Bowen's Disease, bullous pemphigoid, echtima, eczema, epidermolysis bullosa (e.g., simplex, junctional, dystrophic, hemidesmosomal), erythrasma, erysipelas, folliculitis, friction blisters, herpes (e.g., HHV1 i.e., cold sores, HHV2 i.e., genital herpes, HHV3, e.g., chickenpox, shingles, HHV6, HHV7, e.g., roseola infantum, sixth disease, HHV8, i.e., Kaposi's sarcoma herpesvirus), hidradenitis suppurativa, hives, hyperhidrosis, ichthyosis, impetigo, jock itch, Kaposi's sarcoma, keloid, keratoacanthoma, keratosis (e.g., actinic (solar) keratosis, keratosis pilaris, keratosis follicularis (Daffier's disease), seborrheic, and hyperkeratosis), lice infection, lichen planus, lichen simplex chronicus, lipoma, lymphadenitis, malignant melanoma, melisma, miliaria, molluscum contagiosum, Paget's disease of the nipple, pediculosis, pemphigus, photoallergy, photosensitivity, *pityriasis rosea, pityriasis rubra* pilaris, psoriasis, Raynaud's disease, ring worm, Raynaud's disease, rosacea, Saint Anthony's fire, scabies, scleroderma, sebaceous cyst, shingles, skin cancer, skin tags, spider veins (telangiectasia), squamous cell carcinoma, tick bite, tinea: (barbae, capitis, corporis, cruris (Jock Itch), pedis unguium, *versicolor*), trichomycosis, varicose veins, vitiligo, and warts (e.g., common, planar, genital).

In some aspects, the disclosure provides a method of treating an adipose tissue disorder in a subject in need thereof, comprising administering to the subject an effective amount of a therapeutic agent for treating the adipose tissue disorder coupled to an adipose tissue venule endothelial cell targeting agent which binds to il6st on the surface of an adipose tissue venule endothelial cell. In some embodiments, the adipose tissue venule endothelial cell targeting agent delivers the coupled therapeutic agent to adipose tissue venule endothelial cells. In some embodiments, delivery of the therapeutic agent to the adipose tissue venule endothelial cell induces a local therapeutic effect in the adipose tissue venule endothelial cell, or a venule, tissue or organ surrounding the adipose tissue venule endothelial cell. In some embodiments, delivery of the therapeutic agent to the adipose tissue venule endothelial cell minimizes or eliminates an effect in the subject selected from the group consisting of a systemic effect, a toxic effect, an adverse effect, a side effect, and an undesired effect. In some embodiments, the method includes modifying a dose of the therapeutic agent for local delivery to the adipose tissue venule endothelial cell. In some embodiments, the method includes selecting a subject who would likely benefit from delivery of the therapeutic agent to the subject's adipose tissue venule endothelial cells. In some embodiments, the adipose tissue disorder is a disease characterized by visceral fat inflammation selected from the group consisting of cancer, CVHD, fibrosis, hypertension, lypodystrophy, obesity, metabolic syndrome, and type II diabetes. In some embodiments, the adipose tissue disorder is selected from the group consisting of obesity and related disorders selected from the group consisting of cancer, cellulitis, chronic renal failure, depression, diabetes, erectile dysfunction, fatty liver disease, gallbladder disease (e.g., gallstones), gastroesophageal reflux disease, gout, heart disease (e.g., congestive heart failure, enlarged heart), hernia, high blood pressure, hypercholesterolemia, infection, infertility, lymph edema, osteoarthritis, pain, Pickwickian syndrome, pulmonary embolism, polycystic ovarian syndrome, ulcers, stroke, and urinary incontinence.

In some aspects, the disclosure provides a composition comprising a venule endothelial cell targeting agent which binds to il6st on the surface of a venule endothelial cell. In some embodiments, the composition includes an agent. In some embodiments, the agent is coupled to the venule endothelial cell targeting agent. In some embodiments, the venule endothelial cell targeting agent and/or agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the venule endothelial cell targeting agent and/or agent comprises an aptide. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the venule endothelial cell targeting agent is coupled to the agent via a linker. In some embodiments, the venule endothelial cell targeting agent or the agent is coupled to a detectable reporter. In some embodiments, the venule endothelial cell targeting agent and/or the agent is encapsulated in a nanoparticle or microparticle. In some embodiments, the nanoparticle comprises a lipid nanoparticle or microparticle. In some embodiments, the nanoparticle comprises a polymeric nanoparticle constructed from low molecular weight polyamines and lipids. In some embodiments, administration of the composition to a subject delivers the agent to the subject's venule endothelial cells. In some embodiments, delivering the agent to the subject's venule endothelial cells treats, prevents, or ameliorates a symptom of, a disease in the subject. In some embodiments, the disease is an inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some aspects, the disclosure provides a composition comprising a skin venule endothelial cell targeting agent which binds to a protein expressed on the surface of a venule endothelial cell in skin. In some embodiments, the composition includes an agent. In some embodiments, the skin venule endothelial cell targeting agent is coupled to the agent. In some embodiments, the skin venule endothelial cell targeting agent and/or agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the skin venule endothelial cell targeting agent and/or agent comprises an aptide. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the skin venule endothelial cell targeting agent is coupled to the agent via a linker. In some embodiments, the skin venule endothelial cell targeting agent or agent is coupled to a detectable reporter. In some embodiments, the skin venule endothelial cell targeting agent and/or agent are encapsulated in nanoparticles or microparticles. In some embodiments, the nanoparticle comprises a polymeric nanoparticle constructed from low molecular weight polyamines and lipids. In some embodiments, administering the composition to a subject delivers the agent to the subject's skin venule endothelial cells. In some embodiments, delivering the agent to skin venule endothelial cells of the subject treats, prevents, or ameliorates a symptom of, a skin disease in the subject. In some embodiments, the skin disease is selected from the group consisting of acne, alopecia (e.g., alopecia areata, alopecia totalis, alopecia universalis, traction alopecia), angioma, athlete's foot, basal cell carcinoma, bed sore, Behcet's Disease, blepharitis, boil, calluses and corns, canker sore, carbuncles, candidiasis (e.g., oral (oral thrush), vaginal (candidal vulvovaginitis, penile (candidal balanitis), in the diaper area (diaper rash), in the skin folds (candidal intertrigo), cellulitis, cold sores, creeping eruption, dandruff, dermatitis (eczema) (e.g., atopic dermatitis, contact dermatitis, seborrhoeic dermatitis, cradle cap, nummular dermatitis, stasis dermatitis, perioral dermatitis (muzzle rash), dermatitis herpetiformis), dermatofibroma, Bowen's Disease, bullous pemphigoid, echtima, eczema, epidermolysis bullosa (e.g., simplex, junctional, dystrophic, hemidesmosomal), erythrasma, erysipelas, folliculitis, friction blisters, herpes (e.g., HHV1 i.e., cold sores, HHV2 i.e., genital herpes, HHV3, e.g., chickenpox, shingles, HHV6, HHV7, e.g., roseola infantum, sixth disease, HHV8, i.e., Kaposi's sarcoma herpesvirus), hidradenitis suppurativa, hives, hyperhidrosis, ichthyosis, impetigo, jock itch, Kaposi's sarcoma, keloid, keratoacanthoma, keratosis (e.g., actinic (solar) keratosis, keratosis pilaris, keratosis follicularis (Darrier's disease), seborrheic, and hyperkeratosis), lice infection, lichen planus, lichen simplex chronicus, lipoma, lymphadenitis, malignant melanoma, melisma, miliaria, molluscum contagiosum, Paget's disease of the nipple, pediculosis, pemphigus, photoallergy, photosensitivity, *pityriasis rosea*, *pityriasis rubra* pilaris, psoriasis, Raynaud's disease, ring worm, Raynaud's disease, rosacea, Saint Anthony's fire, scabies, scleroderma, sebaceous cyst, shingles, skin cancer, skin tags, spider veins (telangiectasia), squamous cell carcinoma, tick bite, tinea: (barbae, capitis, corporis, cruris (Jock Itch), pedis unguium, *versicolor*), trichomycosis, varicose veins, vitiligo, warts (e.g., common, planar, genital). In some embodiments, the skin disease is a skin inflammatory disease. In some embodiments, the skin inflammatory disease is selected from the group consisting of acne, dermatitis, eczema, oily skin, rosacea, cutaneous lymphoma and urticaria. In some embodiments, the dermatitis is selected from the group consisting of atopic dermatitis, psoriasis and contact dermatitis.

In some aspects, the disclosure provides a composition comprising an adipose tissue venule endothelial cell targeting agent which binds to il6st on the surface of a venule endothelial cell in adipose tissue. In some embodiments, the composition includes an agent. In some embodiments, the adipose tissue venule endothelial cell targeting agent is coupled to the agent. In some embodiments, the adipose tissue venule endothelial cell targeting agent and/or agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the adipose tissue venule endothelial cell targeting agent and/or agent comprises an aptide. In some embodiments, the agent comprises a therapeutic agent. In some embodiments, the agent comprises an anti-inflammatory agent. In some embodiments, the agent comprises a diagnostic agent. In some embodiments, the agent comprises an imaging agent. In some embodiments, the adipose tissue venule endothelial cell targeting agent is coupled to the agent via a linker. In some embodiments, the adipose tissue venule endothelial cell targeting agent or agent is coupled to a detectable reporter. In some embodiments, the adipose tissue venule endothelial cell targeting agent and/or agent are encapsulated in a nanoparticle or microparticle. In some embodiments, the nanoparticle comprises a polymeric nanoparticle constructed from low molecular weight polyamines and lipids. In some embodiments, administration of the composition to a subject delivers the agent to the subject's adipose tissue venule endothelial cells. In some embodiments, delivering the agent to the subject's adipose tissue venule endothelial cells treats, prevents, or ameliorates a symptom of, an adipose tissue disease. In some embodiments, the adipose tissue disease is selected from the group consisting of obesity and related disorders selected from the group consisting of cancer, cellulitis, chronic renal failure, depression, diabetes, erectile dysfunction, fatty liver disease, gallbladder disease (e.g., gallstones), gastro-esophageal reflux disease, gout, heart disease (e.g., congestive heart failure, enlarged heart), hernia, high blood pressure, hypercholesterolemia, infection, infertility, lymph edema, osteoarthritis, pain, Pickwickian syndrome, pulmonary embolism, polycystic ovarian syndrome, ulcers, stroke, and urinary incontinence. In some embodiments, the adipose tissue disease is a disease characterized by inflammation in the subject's visceral fat. In some embodiments, the disease is selected from the group consisting of cancer, CVHD, fibrosis, hypertension, lypodystrophy, obesity, metabolic syndrome, and type II diabetes.

In some aspects, the disclosure provides a method of identifying a candidate venule endothelial cell targeting agent which binds to il6st on the surface of a venule endothelial cell, comprising: (a) contacting il6st on the surface of a venule endothelial cell with a test agent; and (b) assessing the ability of the test agent to bind il6st on the surface of the venule endothelial cell, wherein a test agent that binds to il6st on the surface of the venule endothelial cell is a candidate venule endothelial cell targeting agent. In some aspects, the disclosure provides a method of identifying a candidate venule endothelial cell targeting agent which binds to a il6st on the surface of a venule endothelial cell and delivers an agent to a venule endothelial cell in a subject, comprising: (a) administering to a subject a test venule endothelial cell targeting agent which binds to il6st on the surface of a venule endothelial cell coupled to an agent; and (b) assessing the ability of the venule endothelial cell targeting agent to deliver the agent to a venule endothelial cell in the subject, wherein a test agent that delivers the agent to a venule endothelial cell in the subject is a candidate venule endothelial cell targeting agent. In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the test agent comprises an aptide. In some embodiments, administration comprises intravenous infusion. In some embodiments, the agent comprises a fluorescent component. In some embodiments, the agent is a fluorescent reagent. In some embodiments, assessing the ability of the venule endothelial cell targeting agent to deliver the agent to a venule endothelial cell comprises in situ imaging of the test agent or the agent. In some embodiments, assessing the ability of the venule endothelial cell targeting agent to deliver the agent to a venule endothelial cell comprises analyzing internalization of the test agent or the agent in a venule, tissue, or organ surrounding the venule endothelial cell. In some embodiments, assessing the ability of the venule endothelial cell targeting agent to deliver the agent to a venule endothelial cell comprises analyzing accumulation of the test agent or the agent in a venule, tissue, or organ surrounding the venule endothelial cell.

In some aspects, the disclosure provides a method of identifying a candidate skin venule endothelial cell targeting agent which binds to il6st on the surface of a skin venule endothelial cell, comprising: (a) contacting il6st on the surface of a skin venule endothelial cell with a test agent; and (b) assessing the ability of the test agent to bind il6st on the surface of the skin venule endothelial cell, wherein a test agent that binds to il6st on the surface of the skin venule endothelial cell is a candidate skin venule endothelial cell targeting agent. In some aspects, the disclosure provides a method of identifying a candidate skin venule endothelial cell targeting agent which binds to il6st on the surface of a skin venule endothelial cell and delivers an agent to a skin venule endothelial cell in a subject, comprising: (a) administering to a subject a test skin venule endothelial cell targeting agent which binds to il6st on the surface of a skin venule endothelial cell coupled to an agent; and (b) assessing the ability of the test skin venule endothelial cell targeting agent to deliver the agent to a skin venule endothelial cell in the subject, wherein a test skin venule endothelial cell targeting agent that delivers the agent to a skin venule endothelial cell in the subject is a candidate skin venule endothelial cell targeting agent. In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the test agent comprises an aptide. In some embodiments, administration comprises intravenous infusion. In some embodiments, the agent comprises a fluorescent component. In some embodiments, the agent is a fluorescent reagent. In some embodiments, assessing the ability of the skin venule endothelial cell targeting agent to deliver the agent to a skin venule endothelial cell comprises in situ imaging of the test agent or the agent. In some embodiments, assessing the ability of the skin venule endothelial cell targeting agent to deliver the agent to a skin venule endothelial cell comprises analyzing internalization of the test agent or the agent in a venule, tissue, or organ surrounding the skin venule endothelial cell. In some embodiments, assessing the ability of the skin venule endothelial cell targeting agent to deliver the agent to a skin venule endothelial cell comprises analyzing accumulation of the test agent or the agent in a venule, tissue, or organ surrounding the skin venule endothelial cell.

In some aspects, the disclosure provides a method of identifying a candidate adipose tissue venule endothelial cell targeting agent which binds to il6st on the surface of an adipose tissue venule endothelial cell, comprising: (a) contacting il6st on the surface of an adipose tissue venule endothelial cell with a test agent; and (b) assessing the ability of the test agent to bind il6st on the surface of the adipose tissue venule endothelial cell, wherein a test agent that binds to il6st on the surface of the adipose tissue venule endothelial cell is a candidate adipose tissue venule endothelial cell targeting agent. In some aspects, the disclosure provides a method of identifying a candidate adipose tissue venule endothelial cell targeting agent which binds to il6st on the surface of an adipose tissue venule endothelial cell and delivers an agent to an adipose tissue venule endothelial cell in a subject, comprising: (a) administering to a subject a test adipose tissue venule endothelial cell targeting agent which binds to il6st on the surface of an adipose tissue venule endothelial cell coupled to an agent; and (b) assessing the ability of the test adipose tissue venule endothelial cell targeting agent to deliver the agent to an adipose tissue venule endothelial cell in the subject, wherein a test adipose tissue venule endothelial cell targeting agent that delivers the agent to an adipose tissue venule endothelial cell in the subject is a candidate adipose tissue venule endothelial cell targeting agent. In some embodiments, the test agent is selected from the group consisting of small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, the test agent comprises an aptide. In some embodiments, administration comprises intravenous infusion. In some embodiments, the agent comprises a fluorescent component. In some embodiments, the agent is a fluorescent reagent. In some embodiments, assessing the ability of the adipose tissue venule endothelial cell targeting agent to deliver the agent to an adipose tissue venule endothelial cell comprises in situ imaging of the test agent or the agent. In some embodiments, assessing the ability of the adipose tissue venule endothelial cell targeting agent to deliver the agent to an adipose tissue venule endothelial cell comprises analyzing internalization of the test agent or the agent in a venule, tissue, or organ surrounding the adipose tissue venule endothelial cell. In some embodiments, assessing the ability of the adipose tissue venule endothelial cell targeting agent to deliver the agent to an adipose tissue venule endothelial cell comprises analyzing accumulation of the test agent or the agent in a venule, tissue, or organ surrounding the adipose tissue venule endothelial cell.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 demonstrates targeted delivery of agents to tissues (e.g., adipose tissue and skin) based on their ability to bind surface markers (e.g., CD130, also known as GP130 or il6st) expressed in a microvessel (e.g., venules). FIG. 1 is a micrograph of whole mount staining in mouse omentum (top row) and skin (bottom row) showing staining of the microvasculature with anti-CD31 Ab (first panel) and venules with anti-DARC Ab (second panel). The third and fourth panels show the presence of anti-CD130 conjugated fluorescent beads and isotype control conjugated beads respectively, after intravenous injection. The specific binding of anti-CD130 conjugated beads to DARC+ venules has been validated in vivo by intravital microscopy as well.

DETAILED DESCRIPTION OF THE INVENTION

Disclosed herein are methods, compositions, agents, and kits useful for targeted delivery of agents to tissues based on their ability to bind to surface markers expressed in microvessels (e.g., venules or non-venules), methods of identifying agents that target microvessels, methods for treating diseases of microvessel endothelial origin (e.g., microvasculature diseases, diseases associated with leukocyte trafficking, inflammatory diseases, cancer, infection, etc.) and compositions and kits for use in the methods.

As used herein, "venule" refers to a microvessel in which the endothelium of the microvessel comprises venule endothelial cells, and in which leukocyte trafficking occurs (e.g., a post-capillary venule or a collecting venule). As used herein, "venule endothelial cells," "V-ECs" and "venular endothelial cells" are used interchangeably to refer to endothelial cells that form the endothelium of venules. It should be appreciated that a venule or venule endothelial cell may display a marker or combination of markers indicative of venuleness (e.g., a gene or combination of genes which is differentially or selectively expressed in venule endothelial cells compared to non-venule endothelial cells, e.g., DARC+/CD31+). In contrast to a venule, a "non-venule" refers to a microvessel in which the endothelium of the microvessel comprises non-venule endothelial cells, and in which leukocyte trafficking typically does not occur (e.g., a capillary or arteriole). As used herein, "non-venule endothelial cell", and "NV-EC" are used interchangeably to refer to endothelial cells that form the endothelium of non-venules. It should be appreciated hat a non-venule or non-venule endothelial cell may display a marker or combination of markers indicative of non-venuleness (e.g., a gene or combination of genes which is differentially or selectively expressed in non-venule endothelial cells compared to venule-endothelial cells, e.g., DARC−/CD31+).

Targeting Methods

In an aspect, disclosed herein are methods of delivering an agent to a microvessel endothelial cell in a subject. An exemplary method of delivering an agent to a microvessel endothelial cell in a subject comprises administering to the subject a microvessel endothelial cell targeting agent which binds to a protein expressed on the surface of a microvessel endothelial cell.

As used herein "deliver", "delivering", "target", "targeting" and related terminology are used interchangeably to refer to delivering a molecule (e.g., an agent described herein, including an endothelial cell targeting agent described herein) to a specific intended site in a way that minimizes delivery of the molecule to an unintended site.

As used herein a "targeting agent" refers to any molecule that recognizes, binds to, or otherwise interacts with an endothelial cell surface marker described herein or a variant thereof with sufficient affinity and specificity to deliver the molecule to an endothelial cell expressing such surface marker, without delivering or only negligibly delivering the molecule to other cells. It should be appreciated that the targeting agent can recognize, bind to, or otherwise interact with an endothelial cell surface marker described herein or a variant thereof and can influence the physiological function of the endothelial cell surface marker (e.g., by inhibiting or augmenting the surface marker itself or downstream activities of the surface marker). Alternatively or additionally, a targeting agent can recognize, bind to, or otherwise interact with an endothelial cell surface marker described herein or a variant thereof and bring an agent described herein into close proximity to an endothelial cell expressing the surface marker. In such instances, the agent may influence the physiological function of the endothelial cell surface marker or otherwise be internalized into or transported across the endothelial cell.

In some embodiments, the microvessel endothelial cell targeting agent causes an effect in the microvessel endothelial cell, or a microvessel, tissue or organ adjacent to the microvessel endothelial cell. In some embodiments, the microvessel endothelial cell targeting agent is coupled to an agent which causes an effect in the microvessel endothelial cell, or a microvessel, tissue or organ adjacent to the microvessel endothelial cell.

As used herein, "microvessel endothelial cell targeting agent" refers to a targeting agent that is capable of targeting endothelial cells lining a microvessel by binding to a microvessel endothelial cell surface marker described herein (e.g., a protein expressed on the surface of a microvessel endothelial cell). In some embodiments, the protein expressed on the surface of the microvessel endothelial cell is encoded by a gene that is preferentially expressed in microvessels. As used herein, "preferentially expressed in microvessels" means that a gene is over-represented or under-represented in venules as compared to non-venules, or vice versa. Exemplary genes which are preferentially expressed in microvessels include, but are not limited to, Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4; Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, Cd74. Exemplary genes which are preferentially expressed in microvessels include, but are not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mrl, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

Table 1 lists microvessel endothelial cell surface markers. As used herein "Table 1" includes Table 1A and Table 1B below. It should be appreciated that the various aspects and embodiments of the disclosure contemplate using the genes (including mRNA and/or protein) listed in Table 1, as well as corresponding human genes (i.e., genes which exhibit similar sequence and functionality in the respective tissue). One of skill in the art will readily be able to obtain amino acid sequences of endothelial cell surface marker polypeptides, and the genomic and mRNA sequences encoding them, from publicly available databases, such as those available at the National Center for Biotechnology Information (NCBI), e.g., Gene, GenBank, Proteins, etc. For example, the Nucleotide database provides sequence information (e.g., accession numbers for reference sequences (in the RefSeq database)) and functional information, which can be obtained, e.g., by searching on a name or Accession Number for a nucleic acid or protein of interest. Table 1 provides a list of the official symbol and Accession Numbers of certain microvessel endothelial cell surface marker genes of interest.

TABLE 1

| Microvessel Endothelial Cell Surface Markers | | |
|---|---|---|
| Gene Symbol | Gene Name | Gene Accession Number |
| Sele | selectin, endothelial cell | NM_011345 |
| Selp | selectin, platelet | NM_011347 |
| Il6st | interleukin 6 signal transducer | NM_010560 |
| Plxnb2 | plexin B2 | NM_138749, NM_001159521 |
| Lepr | leptin receptor | NM_146146, NM_001122899, NM_010704 |
| Bst1 | bone marrow stromal cell antigen 1 | NM_009763 |
| Icam1 | intercellular adhesion molecule 1 | NM_010493 |
| Nrp2 | neuropilin 2 | NM_001077403, NM_001077404, NM_010939, NM_001077405, NM_001077406, NM_001077407 |
| Gpr1 | G protein-coupled receptor 1 | NM_146250 |
| C630004H02Rik | RIKEN cDNA C630004H02 gene | NM_175454 |
| Fndc1 | fibronectin type III domain containing 1 | NM_001081416 |
| 2310046K01Rik | RIKEN cDNA 2310046K01 gene | BC016127 |
| Insr | insulin receptor | NM_010568 |
| Slco2a1 | solute carrier organic anion transporter family, member 2a1 | NM_033314 |
| Il1rl1 | interleukin 1 receptor-like 1 | NM_001025602, NM_010743 |
| Csprs, Gm7609 | component of Sp100-rs, predicted pseudogene 7609 | NM_033616, NM_001081746 |
| Rgs1 | regulator of G-protein signaling 1 | NM_015811 |
| Gpr126 | G protein-coupled receptor 126 | NM_001002268 |
| P2rx1 | purinergic receptor P2X, ligand-gated ion channel, 1 | NM_008771 |
| Slc6a4 | solute carrier family 6 (neurotransmitter transporter, serotonin), member 4 | NM_010484 |
| Itgb4 | integrin beta 4 | NM_001005608, NM_133663 |

TABLE 1-continued

Microvessel Endothelial Cell Surface Markers

| Gene Symbol | Gene Name | Gene Accession Number |
|---|---|---|
| A530099J19Rik | RIKEN cDNA A530099J19 gene | NM_175688 |
| Fcer1g | Fc receptor, IgE, high affinity I, gamma polypeptide | NM_010185 |
| Fcer1a | Fc receptor, IgE, high affinity I, alpha polypeptide | NM_010184 |
| Slc7a8 | solute carrier family 7 (cationic amino acid transporter, y+ system), member 8 | NM_016972 |
| Nckap1l | NCK associated protein 1 like | NM_153505 |
| Sla | src-like adaptor | NM_001029841, NM_009192 |
| Emp2 | epithelial membrane protein 2 | NM_007929 |
| Entpd1 | ectonucleoside triphosphate diphosphohydrolase 1 | NM_009848 |
| Slc18a2 | solute carrier family 18 (vesicular monoamine), member 2 | NM_172523 |
| Ms4a2 | membrane-spanning 4-domains, subfamily A, member 2 | NM_013516 |
| Cd59a, Cd59b | CD59a antigen, CD59b antigen | NM_007652, NM_001111060, NM_181858 |
| Adora3 | adenosine A3 receptor | NM_001174169, NM_009631 |
| Ddah1 | dimethylarginine dimethylaminohydrolase 1 | NM_026993 |
| Cpa3 | carboxypeptidase A3, mast cell | NM_007753 |
| I830077J02Rik | RIKEN cDNA I830077J02 gene | NM_001033780 |
| Vcam1 | vascular cell adhesion molecule 1 | NM_011693 |
| Laptm5 | lysosomal-associated protein transmembrane 5 | NM_010686 |
| Kit | kit oncogene | NM_021099, NM_001122733 |
| P2rx4 | purinergic receptor P2X, ligand-gated ion channel 4 | NM_011026 |
| Cmklr1 | chemokine-like receptor 1 | NM_008153 |
| Lat2 | linker for activation of T cells family, member 2 | NM_022964, NM_020044 |
| Pilra | paired immunoglobin-like type 2 receptor alpha | NM_153510 |
| Aqp1 | aquaporin 1 | NM_007472 |
| Gp9 | glycoprotein 9 (platelet) | NM_018762 |
| Slc6a12 | solute carrier family 6 (neurotransmitter transporter, betaine/GABA), member 12 | NM_133661 |
| Emp1 | epithelial membrane protein 1 | NM_010128 |
| Cd33 | CD33 antigen | NM_001111058, NM_021293 |
| Tph1 | tryptophan hydroxylase 1 | NM_009414, NM_001136084 |
| Mrgprb1 | MAS-related GPR, member B1 | NM_205810 |
| Mrgprb2 | MAS-related GPR, member B2 | NM_175531 |
| Slc7a5 | solute carrier family 7 (cationic amino acid transporter, y+ system), member 5 | NM_011404 |
| Mras | muscle and microspikes RAS | NM_008624 |
| Atp1b3 | ATPase, Na+/K+ transporting, beta 3 polypeptide | NM_007502 |
| Ly96 | lymphocyte antigen 96 | NM_016923, NM_001159711 |
| Ddr2 | discoidin domain receptor family, member 2 | NM_022563 |
| Madcam1 | mucosal vascular addressin cell adhesion molecule 1 | NM_013591 |
| Ctla2a | cytotoxic T lymphocyte-associated protein 2 alpha | NM_007796, NM_001145799 |
| Sema5a | sema domain, seven thrombospondin repeats (type 1 and type 1-like), transmembrane domain (TM) and short cytoplasmic domain, (semaphorin) 5A | NM_009154 |
| Enpp2 | ectonucleotide pyrophosphatase/phosphodiesterase 2 | NM_015744, NM_001136077 |
| Ly6i | lymphocyte antigen 6 complex, locus I | NM_020498 |
| Celsr1 | cadherin, EGF LAG seven-pass G-type receptor 1 (flamingo homolog, *Drosophila*) | NM_009886 |
| Glycam1 | glycosylation dependent cell adhesion molecule 1 | NM_008134 |
| Robo1 | roundabout homolog 1 (*Drosophila*) | NM_019413 |
| Dsg2 | desmoglein 2 | NM_007883 |
| Cdh2 | cadherin 2 | NM_007664 |
| Abca2 | ATP-binding cassette, sub-family A (ABC1), member 2 | NM_007379 |

TABLE 1-continued

Microvessel Endothelial Cell Surface Markers

| Gene Symbol | Gene Name | Gene Accession Number |
|---|---|---|
| Snap23 | synaptosomal-associated protein 23 | NM_009222, NM_001177792, NM_001177793 |
| Pcdh7 | protocadherin 7 | NM_001122758, NM_018764 |
| Met | met proto-oncogene | NM_008591 |
| Vmn2r43, Vmn2r31, Vmn2r35, Vmn2r39, Vmn2r50, Vmn2r44 | vomeronasal 2, receptor 43, vomeronasal 2, receptor 31, vomeronasal 2, receptor 35, vomeronasal 2, receptor 39, vomeronasal 2, receptor 50, vomeronasal 2, receptor 44 | NM_198961; NM_001105062; NM_001105067; NM_001105071; NM_001105178; NM_001105074 |
| Slc1a5 | solute carrier family 1 (neutral amino acid transporter), member 5 | NM_009201 |
| Pglyrp1 | peptidoglycan recognition protein 1 | NM_009402 |
| Olfr46, Olfr538 | olfactory receptor 46, olfactory receptor 538 | NM_146934; NM_001011867 |
| Lyve1 | lymphatic vessel endothelial hyaluronan receptor 1 | NM_053247 |
| Il27ra | interleukin 27 receptor, alpha | NM_016671 |
| Pvrl1 | poliovirus receptor-related 1 | NM_021424 |
| Stra6 | stimulated by retinoic acid gene 6 | NM_001162476, NM_009291, NM_001162475, NM_001162479 |
| Tspan3 | tetraspanin 3 | NM_019793 |
| Tspan7 | tetraspanin 7 | NM_019634 |
| Il2rg | interleukin 2 receptor, gamma chain | NM_013563 |
| Gpr182 | G protein-coupled receptor 182 | NM_007412 |
| Slco2b1 | solute carrier organic anion transporter family, member 2b1 | NM_001252530, NM_001252531, NM_175316 |
| Cd63 | CD63 antigen | NM_007653, NM_001042580 |
| Sirpa | signal-regulatory protein alpha | NM_007547, NM_001177646, NM_001177647 |
| Slc2a1 | solute carrier family 2 (facilitated glucose transporter), member 1 | NM_011400 |
| Vmn1r100 | vomeronasal 1 receptor 100 | NM_001166844 |
| Vmn1r148 | vomeronasal 1 receptor 148 | NM_030736 |
| Vmn1r132 | vomeronasal 1 receptor 132 | NM_001122682 |
| Vmn1r125 | vomeronasal 1 receptor 125 | NM_001166740 |
| Il1r1 | interleukin 1 receptor, type I | NM_008362, NM_001123382 |
| Tbc1d8 | TBC1 domain family, member 8 | NM_018775 |
| Cd55 | CD55 antigen | NM_010016 |
| Cadm3 | cell adhesion molecule 3 | NM_053199 |
| Htr2a | 5-hydroxytryptamine (serotonin) receptor 2A | NM_172812 |
| Csf2rb2 | colony stimulating factor 2 receptor, beta 2, low-affinity (granulocyte-macrophage) | NM_007781 |
| Amigo2 | adhesion molecule with Ig like domain 2 | NM_178114, NM_001164602, NM_001164563 |
| Adrb2 | adrenergic receptor, beta 2 | NM_007420 |
| Procr | protein C receptor, endothelial | NM_011171 |
| Lbp | lipopolysaccharide binding protein | NM_008489 |
| Ehd4 | EH-domain containing 4 | NM_133838 |
| Kcnb1 | potassium voltage gated channel, Shab-related subfamily, member 1 | NM_008420 |
| Tspan5 | tetraspanin 5 | NM_019571 |
| Clca1 | chloride channel calcium activated 1 | NM_009899 |
| Gem | GTP binding protein (gene overexpressed in skeletal muscle) | NM_010276 |
| Ctnnal1 | catenin (cadherin associated protein), alpha-like 1 | NM_018761 |
| Tacr1 | tachykinin receptor 1 | NM_009313 |
| Ret | ret proto-oncogene | NM_009050, NM_001080780 |
| Anpep | alanyl (membrane) aminopeptidase | NM_008486 |
| Gpm6a | glycoprotein m6a | NM_001253754, NM_153581, NM_001253756 |
| Nt5e | 5' nucleotidase, ecto | NM_011851 |
| Il13ra1 | interleukin 13 receptor, alpha 1 | NM_133990 |

TABLE 1-continued

Microvessel Endothelial Cell Surface Markers

| Gene Symbol | Gene Name | Gene Accession Number |
|---|---|---|
| Cysltr1 | cysteinyl leukotriene receptor 1 | NM_021476 |
| Flt4 | FMS-like tyrosine kinase 4 | NM_008029 |
| Jup | junction plakoglobin | NM_010593 |
| Lgals3bp | lectin, galactoside-binding, soluble, 3 binding protein | NM_011150 |
| Ednrb | endothelin receptor type B | NM_001136061, NM_007904 |
| Ptp4a3 | protein tyrosine phosphatase 4a3 | NM_001166390, NM_001166388, NM_008975, NM_001166389 |
| Gpihbp1 | GPI-anchored HDL-binding protein 1 | NM_026730 |
| Notch4 | notch 4 | NM_010929 |
| Slc9a3r2 | solute carrier family 9 (sodium/hydrogen exchanger), member 3 regulator 2 | NM_023449, NM_023055 |
| Prnd | prion protein dublet | NM_023043, NM_001126338 |
| Sdc3 | syndecan 3 | NM_011520 |
| Alpl | alkaline phosphatase, liver/bone/kidney | NM_007431 |
| Cldn15 | claudin 15 | NM_021719 |
| Kdr | kinase insert domain protein receptor | NM_010612 |
| Slc6a6 | solute carrier family 6 (neurotransmitter transporter, taurine), member 6 | NM_009320 |
| Podxl | podocalyxin-like | NM_013723 |
| Efnb2 | ephrin B2 | NM_010111 |
| Sema7a | sema domain, immunoglobulin domain (Ig), and GPI membrane anchor, (semaphorin) 7A | NM_011352 |
| Itm2a | integral membrane protein 2A | NM_008409 |
| Sell | selectin, lymphocyte | NM_011346, NM_001164059 |
| Ptprc | protein tyrosine phosphatase, receptor type, C | NM_001111316, NM_011210, NM_001268286 |
| Cd68 | CD68 antigen | NM_009853 |
| Cd79b | CD79B antigen | NM_008339 |
| Cd180 | CD180 antigen | NM_008533 |
| Ly6d | lymphocyte antigen 6 complex, locus D | NM_010742 |
| Cldn5 | claudin 5 | NM_013805 |
| Cd200 | CD200 antigen | NM_010818 |
| H2-DMa | histocompatibility 2, class II, locus DMa | NM_010386 |
| H2-Eb1 | histocompatibility 2, class II antigen E beta | NM_010382 |
| Fads2 | fatty acid desaturase 2 | NM_019699 |
| Cd44 | CD44 antigen | NM_001177787, NM_009851, NM_001177785, NM_001039150, NM_001039151, NM_001177786 |
| Cd53 | CD53 antigen | NM_007651 |
| Alox5ap | arachidonate 5-lipoxygenase activating protein | NM_009663 |
| Selplg | selectin, platelet (p-selectin) ligand | NM_009151 |
| Irak2 | interleukin-1 receptor-associated kinase 2 | NM_172161, NM_001113553 |
| Cd69 | CD69 antigen | NM_001033122 |
| Tyrobp | TYRO protein tyrosine kinase binding protein | NM_011662 |
| Nkg7 | natural killer cell group 7 sequence | NM_024253 |
| Siglech | sialic acid binding Ig-like lectin H | NM_178706 |
| Cd37 | CD37 antigen | NM_007645 |
| Gprc5b | G protein-coupled receptor, family C, group 5, member B | NM_022420, NM_001195774 |
| Cd209a | CD209a antigen | NM_133238 |
| Cd209d | CD209d antigen | NM_130904 |
| Ccr9 | chemokine (C-C motif) receptor 9 | NM_009913, NM_001166625 |
| Adora2a | adenosine A2a receptor | NM_009630 |
| H2-Ab1 | histocompatibility 2, class II antigen A, beta 1 | NM_207105 |
| Hspg2 | perlecan (heparan sulfate proteoglycan 2) | NM_008305 |
| Gpr81 | G protein-coupled receptor 81 | NM_175520 |
| Kcna5 | potassium voltage-gated channel, shaker-related subfamily, member 5 | NM_145983 |
| Jam3 | junction adhesion molecule 3 | NM_023277 |
| Gpc4 | glypican 4 | NM_008150 |
| Sdpr | serum deprivation response | NM_138741 |
| Tns1 | tensin 1 | NM_027884 |

TABLE 1-continued

Microvessel Endothelial Cell Surface Markers

| Gene Symbol | Gene Name | Gene Accession Number |
|---|---|---|
| Mpzl1 | myelin protein zero-like 1 | NM_001001880, NM_001083897 |
| Palm | paralemmin | NM_023128, NM_001161747 |
| Ptprb | protein tyrosine phosphatase, receptor type, B | NM_029928 |
| Enpp3 | ectonucleotide pyrophosphatase/phosphodiesterase 3 | NM_134005 |
| Marcks | myristoylated alanine rich protein kinase C substrate | NM_008538 |
| Ramp3 | receptor (calcitonin) activity modifying protein 3 | NM_019511 |
| Pmp22 | peripheral myelin protein 22 | NM_008885 |
| Kcnj2 | potassium inwardly-rectifying channel, subfamily J, member 2 | NM_008425 |
| Olfr1396 | olfactory receptor 1396 | NM_146337 |
| Arrdc3 | arrestin domain containing 3 | NM_001042591 |
| Ppap2a | phosphatidic acid phosphatase type 2A | NM_008903, NM_008247 |
| Ptprg | protein tyrosine phosphatase, receptor type, G | NM_008981 |
| Spata13 | spermatogenesis associated 13 | NM_001033272 |
| Fzd6 | frizzled homolog 6 (Drosophila) | NM_001162494, NM_008056 |
| Tenc1 | tensin like C1 domain-containing phosphatase | NM_153533 |
| Ly6c1 | lymphocyte antigen 6 complex, locus C1 | NM_001252057, NM_001252058, NM_010741, NM_001252056, NM_001252055 |
| Ly6c2 | lymphocyte antigen 6 complex, locus C2 | NM_001099217 |
| Tmem204 | transmembrane protein 204 | NM_001001183 |
| Ptprm | protein tyrosine phosphatase, receptor type, M | NM_008984 |
| Spry4 | sprouty homolog 4 (Drosophila) | NM_011898 |
| Sorbs1 | sorbin and SH3 domain containing 1 | NM_178362, NM_001034963, NM_001034962, NM_001034964, NM_009166 |
| Aplnr | apelin receptor | NM_011784 |
| Mertk | c-mer proto-oncogene tyrosine kinase | NM_008587 |
| Notch1 | notch 1 | NM_008714 |
| Thbd | thrombomodulin | NM_009378 |
| Npr2 | natriuretic peptide receptor 2 | NM_173788 |
| Clstn1 | calsyntenin 1 | NM_023051 |
| Cd36 | CD36 antigen | NM_007643, NM_001159555, NM_001159556, NM_001159557, NM_001159558 |
| Scarb1 | scavenger receptor class B, member 1 | NM_016741, NM_001205082, NM_001205083 |
| Flt1 | FMS-like tyrosine kinase 1 | NM_010228 |
| Dysf | dysferlin | NM_001077694, NM_021469 |
| Mgll | monoglyceride lipase | NM_001166250, NM_001166251, NM_001166249, NM_011844 |
| Klrb1f | killer cell lectin-like receptor subfamily B member 1F | NM_153094 |
| Plxnd1 | plexin D1 | NM_026376 |
| Tm6sf1 | transmembrane 6 superfamily member 1 | NM_145375 |
| Ceacam1 | carcinoembryonic antigen-related cell adhesion molecule 1 | NM_001039185, NM_001039186, NM_011926, NM_001039187 |
| Lrp3 | low density lipoprotein receptor-related protein 3 | NM_001024707 |
| Cdh13 | cadherin 13 | NM_019707 |
| Nrp1 | neuropilin 1 | NM_008737 |
| Dok4 | docking protein 4 | NM_053246 |
| Tns1 | tensin 1 | NM_027884 |
| Cxcr4 | chemokine (C—X—C motif) receptor 4 | NM_009911 |
| Atp1b1 | ATPase, Na+/K+ transporting, beta 1 polypeptide | NM_009721 |

TABLE 1-continued

Microvessel Endothelial Cell Surface Markers

| Gene Symbol | Gene Name | Gene Accession Number |
|---|---|---|
| Car4 | carbonic anhydrase 4 | NM_007607 |
| Cd7 | CD7 antigen | NM_009854 |
| Itga1 | integrin alpha 1 | NM_001033228 |
| Gja5 | gap junction protein, alpha 5 | NM_008121 |
| Laptm5 | lysosomal-associated protein transmembrane 5 | NM_010686 |
| Aqp7 | aquaporin 7 | NM_007473 |
| Gja4 | gap junction protein, alpha 4 | NM_008120 |
| Mlec | malectin | NM_175403 |
| P2ry2 | purinergic receptor P2Y, G-protein coupled 2 | NM_008773 |
| Cd97 | CD97 antigen | NM_001163030, NM_011925, NM_001163029, NM_001163031 |
| Unc5b | unc-5 homolog B (*C. elegans*) | NM_029770 |
| Lpar6, | lysophosphatidic acid receptor 6, | NM_175116; |
| Rb1 | retinoblastoma 1 | NM_009029 |
| Sema6d | sema domain, transmembrane domain (TM), and cytoplasmic domain, (semaphorin) 6D | NM_172537, NM_199238, NM_199239, NM_199240,, NM_199241 |
| Ppap2b | phosphatidic acid phosphatase type 2B | NM_080555 |
| Lpar4 | lysophosphatidic acid receptor 4 | NM_175271 |
| Ly86 | lymphocyte antigen 86 | NM_010745 |
| H2-Aa | histocompatibility 2, class II antigen A, alpha | NM_010378 |
| Cd74 | CD74 antigen (invariant polypeptide of major histocompatibility complex, class II antigen-associated) | NM_010545, NM_001042605 |

TABLE 1B

Microvessel Endothelial Cell Surface Markers

| Gene Symbol | Gene Name | Gene Accession Number |
|---|---|---|
| Sele | selectin, endothelial cell | NM_011345 |
| Selp | selectin, platelet | NM_011347 |
| Kcnh1 | potassium voltage-gated channel, subfamily H (eag-related), member 1 | NM_001038607, NM_010600 |
| Tbc1d8 | TBC1 domain family, member 8 | NM_018775 |
| Cd55 | CD55 antigen | NM_010016 |
| Gpr126 | G protein-coupled receptor 126 | NM_001002268 |
| C630004H02Rik | RIKEN cDNA C630004H02 gene | NM_175454 |
| Plxnb2 | plexin B2 | NM_001159521, NM_138749 |
| Sirpa | signal-regulatory protein alpha | NM_007547, NM_001177646, NM_001177647 |
| Vcam1 | vascular cell adhesion molecule 1 | NM_011693 |
| Clca2 | chloride channel calcium activated 2 | NM_030601 |
| Lepr | leptin receptor | NM_010704, NM_001122899, NM_146146 |
| Bst1 | bone marrow stromal cell antigen 1 | NM_009763 |
| Pcdh7 | protocadherin 7 | NM_018764, NM_001122758 |
| Met | met proto-oncogene | NM_008591 |
| Ret | ret proto-oncogene | NM_001080780, NM_009050 |
| Nt5e | 5' nucleotidase, ecto | NM_011851 |
| Cysltr1 | cysteinyl leukotriene receptor 1 | NM_021476 |
| Nrp2 | neuropilin 2 | NM_001077403 |
| Htr2b | 5-hydroxytryptamine (serotonin) receptor 2B | NM_008311 |
| Mr1 | major histocompatibility complex, class I-related | NM_008209 |
| Anxa1 | annexin A1 | NM_010730 |
| Lphn2 | latrophilin 2 | NM_001081298 |
| Vamp5 | vesicle-associated membrane protein 5 | NM_001080742, NM_016872 |
| Olr1 | oxidized low density lipoprotein (lectin-like) receptor 1 | NM_138648 |

TABLE 1B-continued

Microvessel Endothelial Cell Surface Markers

| Gene Symbol | Gene Name | Gene Accession Number |
|---|---|---|
| Eps8 | epidermal growth factor receptor pathway substrate 8 | NM_007945 |
| Slco2b1 | solute carrier organic anion transporter family, member 2b1 | NM_175316, NM_001252531, NM_001252530 |
| Slco2a1 | solute carrier organic anion transporter family, member 2a1 | NM_033314 |
| Tnfrsf11a | tumor necrosis factor receptor superfamily, member 11a | NM_009399 |
| Mpz | myelin protein zero | NM_008623 |
| Dnm3os | dynamin 3, opposite strand | NR_002870 |
| Icosl | icos ligand | NM_015790 |
| Osbpl8 | oxysterol binding protein-like 8 | NM_001003717, NM_175489 |
| Itga3 | integrin alpha 3 | NM_013565 |
| Flrt2 | fibronectin leucine rich transmembrane protein 2 | NM_201518 |
| Sla | src-like adaptor | NM_009192, NM_001029841 |
| Csf2rb2 | colony stimulating factor 2 receptor, beta 2, low-affinity (granulocyte-macrophage) | NM_007781 |
| Slc2a13 | solute carrier family 2 (facilitated glucose transporter), member 13 | NM_001033633 |
| Emp2 | epithelial membrane protein 2 | NM_007929 |
| Dll1 | delta-like 1 (*Drosophila*) | NM_007865 |
| Entpd1 | ectonucleoside triphosphate diphosphohydrolase 1 | NM_009848 |
| Ptprj | protein tyrosine phosphatase, receptor type, J | NM_001135657, NM_008982 |
| Lrrn4 | leucine rich repeat neuronal 4 | NM_177303 |
| Sulf2 | sulfatase 2 | NM_001252579, NM_001252578, NM_028072 |
| Kcnb1 | potassium voltage gated channel, Shab-related subfamily, member 1 | NM_008420 |
| Adora3 | adenosine A3 receptor | NM_009631 |
| Laptm5 | lysosomal-associated protein transmembrane 5 | NM_010686 |
| Ptafr | platelet-activating factor receptor | NM_001081211 |
| Agtrap | angiotensin II, type I receptor-associated protein | NM_009642 |
| Kit | kit oncogene | NM_001122733, NM_021099 |
| P2rx4 | purinergic receptor P2X, ligand-gated ion channel 4 | NM_011026 |
| Upk3b | uroplakin 3B | NM_175309 |
| Cmklr1 | chemokine-like receptor 1 | NM_008153 |
| Trpv4 | transient receptor potential cation channel, subfamily V, member 4 | NM_022017 |
| Aqp1 | aquaporin 1 | NM_007472 |
| Hrh1 | histamine receptor H1 | NM_001252642, NM_001252643, NM_008285 |
| Cd9 | CD9 antigen | NM_007657 |
| Kcne3 | potassium voltage-gated channel, Isk-related subfamily, gene 3 | NM_001190871, NM_001190869, NM_001190950, NM_020574, NM_001190870 |
| Slco3a1 | solute carrier organic anion transporter family, member 3a1 | NM_023908, NM_001038643 |
| Tm6sf2 | transmembrane 6 superfamily member 2 | NM_181540 |
| Cdon | cell adhesion molecule-related/down-regulated by oncogenes | NM_021339 |
| Olfr920 | olfactory receptor 920 | NM_146787 |
| Itga9 | integrin alpha 9 | NM_133721 |
| Gria3 | glutamate receptor, ionotropic, AMPA3 (alpha 3) | NM_016886 |
| L1cam | L1 cell adhesion molecule | NM_008478 |
| Ly96 | lymphocyte antigen 96 | NM_001159711, NM_016923 |
| Faim3 | Fas apoptotic inhibitory molecule 3 | NM_026976 |
| Sell | selectin, lymphocyte | NM_001164059, NM_011346 |
| Slc2a12 | solute carrier family 2 (facilitated glucose transporter), member 12 | NM_178934 |

TABLE 1B-continued

Microvessel Endothelial Cell Surface Markers

| Gene Symbol | Gene Name | Gene Accession Number |
|---|---|---|
| Ggt5 | gamma-glutamyltransferase 5 | NM_011820 |
| Madcam1 | mucosal vascular addressin cell adhesion molecule 1 | NM_013591 |
| Cd63 | CD63 antigen | NM_001042580, NM_007653 |
| Rtn4rl1 | reticulon 4 receptor-like 1 | NM_177708 |
| Ccr7 | chemokine (C-C motif) receptor 7 | NM_007719 |
| Cd79b | CD79B antigen | NM_008339 |
| Tshr | thyroid stimulating hormone receptor | NM_001113404, NM_011648 |
| Ly86 | lymphocyte antigen 86 | NM_010745 |
| Sema5a | sema domain, seven thrombospondin repeats (type 1 and type 1-like), transmembrane domain (TM) and short cytoplasmic domain, (semaphorin) 5A | NM_009154 |
| Sntb1 | syntrophin, basic 1 | NM_016667 |
| Lynx1 | Ly6/neurotoxin 1 | NM_011838 |
| Ly6i | lymphocyte antigen 6 complex, locus I | NM_020498 |
| Robo1 | roundabout homolog 1 (Drosophila) | NM_019413 |
| Robo2 | roundabout homolog 2 (Drosophila) | NM_175549 |
| H2-DMa | histocompatibility 2, class II, locus DMa | NM_010386 |
| H2-Aa | histocompatibility 2, class II antigen A, alpha | NM_010378 |
| H2-M2 | histocompatibility 2, M region locus 2 | NM_008204 |
| Dsg2 | desmoglein 2 | NM_007883 |
| Cd74 | CD74 antigen (invariant polypeptide of major histocompatibility complex, class II antigen-associated) | NM_001042605 NM_010545 |
| Cdh2 | cadherin 2 | NM_007664 |
| Slc26a2 | solute carrier family 26 (sulfate transporter), member 2 | NM_007885 |
| Vldlr | very low density lipoprotein receptor | NM_001161420, NM_013703 |
| Fads2 | fatty acid desaturase 2 | NM_019699 |
| Ms4a1 | membrane-spanning 4-domains, subfamily A, member 1 | NM_007641 |
| Abca2 | ATP-binding cassette, sub-family A (ABC1), member 2 | NM_007379 |
| Flrt3 | fibronectin leucine rich transmembrane protein 3 | NM_178382, NM_001172160 |
| Cldn11 | claudin 11 | NM_008770 |
| Mme | membrane metallo endopeptidase | NM_008604 |
| Frrs1 | ferric-chelate reductase 1 | NM_001113478, NM_009146 |
| Cd53 | CD53 antigen | NM_007651 |
| Gm13305 /// Gm2002 /// Il11ra2 /// Il11ra1 | predicted gene 13305 /// predicted gene 2002 /// interleukin 11 receptor, alpha chain 2 /// interleukin 11 receptor, alpha chain 1 | NM_001099348, NM_010549, NM_010550, NM_001163401, NM_001172054 |
| Hvcn1 | hydrogen voltage-gated channel 1 | NM_001042489, NM_028752 |
| Daglb | diacylglycerol lipase, beta | NM_144915 |
| P2rx2 | purinergic receptor P2X, ligand-gated ion channel, 2 | NM_001164834, NM_001164833, NM_153400 |
| Cldn13 | claudin 13 | NM_020504 |
| Slc1a5 | solute carrier family 1 (neutral amino acid transporter), member 5 | NM_009201 |
| Cd79a | CD79A antigen (immunoglobulin-associated alpha) | NM_007655 |
| Grin2d | glutamate receptor, ionotropic, NMDA2D (epsilon 4) | NM_008172 |
| Relt | RELT tumor necrosis factor receptor | NM_177073 |
| Lyve1 | lymphatic vessel endothelial hyaluronan receptor 1 | NM_053247 |
| Fgfr2 | fibroblast growth factor receptor 2 | NM_010207, NM_201601 |
| Cdh3 | cadherin 3 | NM_001037809, NM_007665 |
| Fcer2a | Fc receptor, IgE, low affinity II, alpha polypeptide | NM_001253743 |
| Csmd1 | CUB and Sushi multiple domains 1 | NM_053171 |
| Marveld3 | MARVEL (membrane-associating) domain containing 3 | NM_212447, NM_028584 |

TABLE 1B-continued

Microvessel Endothelial Cell Surface Markers

| Gene Symbol | Gene Name | Gene Accession Number |
|---|---|---|
| Ldlr | low density lipoprotein receptor | NM_001252658, NM_010700, NM_001252659 |
| Pvrl1 | poliovirus receptor-related 1 | NM_021424 |
| Stra6 | stimulated by retinoic acid gene 6 | NM_001162479, NM_001162475, NM_009291, NM_001162476 |
| Ccbp2 | chemokine binding protein 2 | NM_021609 |
| Chrnb4 | cholinergic receptor, nicotinic, beta polypeptide 4 | NM_148944 |
| Tspan3 | tetraspanin 3 | NM_019793 |
| Tspan7 | tetraspanin 7 | NM_019634 |
| Chic1 | cysteine-rich hydrophobic domain 1 | NM_009767 |
| Gpr182 | G protein-coupled receptor 182 | NM_007412 |
| H60b | histocompatibility 60b | NM_001177775 |
| Ppap2c | phosphatidic acid phosphatase type 2C | NM_015817 |
| Celsr1 | cadherin, EGF LAG seven-pass G-type receptor 1 (flamingo homolog, *Drosophila*) | NM_009886 |
| Glycam1 | glycosylation dependent cell adhesion molecule 1 | NM_008134 |
| Slc37a1 | solute carrier family 37 (glycerol-3-phosphate transporter), member 1 | NM_001242427, NM_153062 |
| Cd59a | CD59a antigen | NM_007652, NM_001111060 |
| Slc2a1 | solute carrier family 2 (facilitated glucose transporter), member 1 | NM_011400 |
| Tnfrsf9 | tumor necrosis factor receptor superfamily, member 9 | NM_001077509, NM_001077508, NM_011612 |
| Tes | testis derived transcript | NM_207176 |
| Pglyrp1 | peptidoglycan recognition protein 1 | NM_009402 |
| Il27ra | interleukin 27 receptor, alpha | NM_016671 |
| Eda2r | ectodysplasin A2 receptor | NM_001161433, NM_001161432, NM_175540 |
| Il1r1 | interleukin 1 receptor, type I | NM_001123382, NM_008362 |
| Gpr1 | G protein-coupled receptor 1 | NM_146250 |
| Cadm3 | cell adhesion molecule 3 | NM_053199 |
| Itgb4 | integrin beta 4 | NM_001005608, NM_133663 |
| Il6st | interleukin 6 signal transducer | NM_010560 |
| Htr2a | 5-hydroxytryptamine (serotonin) receptor 2A | NM_172812 |
| Stab1 | stabilin 1 | NM_138672 |
| Amigo2 | adhesion molecule with Ig like domain 2 | NM_001164563, NM_001164602, NM_178114 |
| Fndc1 | fibronectin type III domain containing 1 | NM_001081416 |
| Cd14 | CD14 antigen | NM_009841 |
| Adrb2 | adrenergic receptor, beta 2 | NM_007420 |
| Atp8b1 | ATPase, class I, type 8B, member 1 | NM_001001488 |
| Slc52a3 | solute carrier protein family 52, member 3 | NM_027172, NM_001164820, NM_001164819 |
| Procr | protein C receptor, endothelial | NM_011171 |
| Lbp | lipopolysaccharide binding protein | NM_008489 |
| Ehd4 | EH-domain containing 4 | NM_133838 |
| Tspan5 | tetraspanin 5 | NM_019571 |
| Clca1 | chloride channel calcium activated 1 | NM_009899 |
| Gem | GTP binding protein (gene overexpressed in skeletal muscle) | NM_010276 |
| Tlr4 | toll-like receptor 4 | NM_021297 |
| Ctnnal1 | catenin (cadherin associated protein), alpha-like 1 | NM_018761 |
| Tacr1 | tachykinin receptor 1 | NM_009313 |
| Anpep | alanyl (membrane) aminopeptidase | NM_008486 |
| Gpm6a | glycoprotein m6a | NM_001253756, NM_001253754, NM_153581 |
| Insr | insulin receptor | NM_010568 |
| Icam1 | intercellular adhesion molecule 1 | NM_010493 |
| Mras | muscle and microspikes RAS | NM_008624 |
| Il13ra1 | interleukin 13 receptor, alpha 1 | NM_133990 |
| Cxcr4 | chemokine (C—X—C motif) receptor 4 | NM_009911 |
| Unc5b | unc-5 homolog B (*C. elegans*) | NM_029770 |

TABLE 1B-continued

Microvessel Endothelial Cell Surface Markers

| Gene Symbol | Gene Name | Gene Accession Number |
|---|---|---|
| Flt4 | FMS-like tyrosine kinase 4 | NM_008029 |
| Ednrb | endothelin receptor type B | NM_007904, NM_001136061 |
| Notch4 | notch 4 | NM_010929 |
| Prnd | prion protein dublet | NM_001126338, NM_023043 |
| Gja5 | gap junction protein, alpha 5 | NM_008121 |
| Gja4 | gap junction protein, alpha 4 | NM_008120 |
| Alpl | alkaline phosphatase, liver/bone/kidney | NM_007431 |
| Kcna5 | potassium voltage-gated channel, shaker-related subfamily, member 5 | NM_145983 |
| P2ry2 | purinergic receptor P2Y, G-protein coupled 2 | NM_008773 |
| Efnb2 | ephrin B2 | NM_010111 |
| Itm2a | integral membrane protein 2A | NM_008409 |
| Gm7609, Csprs | predicted pseudogene 7609 /// component of Sp100-rs | NM_033616, NM_001081746 |
| Tns1 | tensin 1 | NM_027884 |
| Ptprc | protein tyrosine phosphatase, receptor type, C | NM_001268286, NM_011210, NM_001111316 |
| Rgs1 | regulator of G-protein signaling 1 | NM_015811 |
| Fcer1g | Fc receptor, IgE, high affinity I, gamma polypeptide | NM_010185 |
| Itgb2 | integrin beta 2 | NM_008404 |
| Slc41a2 | solute carrier family 41, member 2 | NM_177388 |
| Cd68 | CD68 antigen | NM_009853 |
| Cd300c | CD300C antigen | NM_199225 |
| Cd7 | CD7 antigen | NM_009854 |
| Cd180 | CD180 antigen | NM_008533 |
| Gpr183 | G protein-coupled receptor 183 | NM_183031 |
| Ptp4a3 | protein tyrosine phosphatase 4a3 | NM_001166389, NM_008975, NM_001166388 |
| Nckap1l | NCK associated protein 1 like | NM_153505 |
| Il7r | interleukin 7 receptor | NM_008372 |
| Sla | src-like adaptor | NM_009192, NM_001029841 |
| Ly6d | lymphocyte antigen 6 complex, locus D | NM_010742 |
| Il2rb | interleukin 2 receptor, beta chain | NM_008368 |
| Slc38a1 | solute carrier family 38, member 1 | NM_134086, NM_001166456, NM_001166458 |
| Cldn5 | claudin 5 | NM_013805 |
| Tigit | T cell immunoreceptor with Ig and ITIM domains | NM_001146325 |
| Cd200 | CD200 antigen | NM_010818 |
| H2-DMa | histocompatibility 2, class II, locus DMa | NM_010386 |
| H2-Ab1 | histocompatibility 2, class II antigen A, beta 1 | NM_207105 |
| H2-Eb1 | histocompatibility 2, class II antigen E beta | NM_010382 |
| H2-Aa | histocompatibility 2, class II antigen A, alpha | NM_010378 |
| Rftn1 | raftlin lipid raft linker 1 | NM_181397 |
| 9430020K01Rik | RIKEN cDNA 9430020K01 gene | NM_001081963 |
| Cd74 | CD74 antigen (invariant polypeptide of major histocompatibility complex, class II antigen-associated) | NM_001042605, NM_010545 |
| Fads2 | fatty acid desaturase 2 | NM_019699 |
| Itga4 | integrin alpha 4 | NM_010576 |
| Slc28a2 | solute carrier family 28 (sodium-coupled nucleoside transporter), member 2 | NM_172980 |
| Cd44 | CD44 antigen | NM_001177787, NM_001177785, NM_009851, NM_001039150, NM_001177786 |
| Stmn2 | stathmin-like 2 | NM_025285 |
| Cd53 | CD53 antigen | NM_007651 |
| Laptm5 | lysosomal-associated protein transmembrane 5 | NM_010686 |
| Kit | kit oncogene | NM_001122733, NM_021099 |
| Hvcn1 | hydrogen voltage-gated channel 1 | NM_001042489, NM_028752 |

TABLE 1B-continued

Microvessel Endothelial Cell Surface Markers

| Gene Symbol | Gene Name | Gene Accession Number |
|---|---|---|
| Gpr30 | G protein-coupled receptor 30 | NM_029771 |
| Alox5ap | arachidonate 5-lipoxygenase activating protein | NM_009663 |
| Prom1 | prominin 1 | NM_001163585, NM_008935, NM_001163582, NM_001163578, NM_001163583, NM_001163584, NM_001163577 |
| Selplg | selectin, platelet (p-selectin) ligand | NM_009151 |
| Cd8b1 | CD8 antigen, beta chain 1 | NM_009858 |
| Cd4 | CD4 antigen | NM_013488 |
| Cd69 | CD69 antigen | NM_001033122 |
| Cd79a | CD79A antigen (immunoglobulin-associated alpha) | NM_007655 |
| Tyrobp | TYRO protein tyrosine kinase binding protein | NM_011662 |
| Nkg7 | natural killer cell group 7 sequence | NM_024253 |
| Siglech | sialic acid binding Ig-like lectin H | NM_178706 |
| Itgal | integrin alpha L | NM_001253874, NM_001253873, NM_008400, NM_001253872 |
| Ifitm1 | interferon induced transmembrane protein 1 | NM_001112715, NM_026820 |
| Lair1 | leukocyte-associated Ig-like receptor 1 | NM_001113474, NM_178611 |
| Cd37 | CD37 antigen | NM_007645 |
| Gprc5b | G protein-coupled receptor, family C, group 5, member B | NM_001195774, NM_022420 |
| Igsf6 | immunoglobulin superfamily, member 6 | NM_030691 |
| Cd209a | CD209a antigen | AF373408 |
| Cd209d | CD209d antigen | ENSMUST00000011445 /// AF373411 |
| Tlr9 | toll-like receptor 9 | NM_031178 |
| Ccr9 | chemokine (C-C motif) receptor 9 | NM_009913, NM_001166625 |
| Mtap2 | microtubule-associated protein 2 | NM_001039934, NM_008632 |
| CXcr7 | chemokine (C—X—C motif) receptor 7 | NM_007722 |
| Palm | paralemmin | NM_001161747, NM_023128 |
| Tbxa2r | thromboxane A2 receptor | NM_009325 |
| Enpp3 | ectonucleotide pyrophosphatase/phosphodiesterase 3 | NM_134005 |
| Pmp22 | peripheral myelin protein 22 | NM_008885 |
| Mmd | monocyte to macrophage differentiation-associated | NM_026178 |
| Ptprg | protein tyrosine phosphatase, receptor type, G | NM_008981 |
| Spata13 | spermatogenesis associated 13 | NM_001033272 |
| Lpar6 | lysophosphatidic acid receptor 6 | NM_175116 |
| Fzd6 | frizzled homolog 6 (*Drosophila*) | NM_001162494, NM_008056 |
| Npr3 | natriuretic peptide receptor 3 | NM_001039181, NM_001286395, NM_008728 |
| Itgb5 | integrin beta 5 | NM_001145884, NM_010580 |
| Scube3 | signal peptide, CUB domain, EGF-like 3 | NM_001004366 |
| Spry4 | sprouty homolog 4 (*Drosophila*) | NM_011898 |
| Ms4a4d | membrane-spanning 4-domains, subfamily A, member 4D | NM_025658 |
| Fas | Fas (TNF receptor superfamily member 6) | NM_007987 |
| Aplnr | apelin receptor | NM_011784 |
| Sema6d | sema domain, transmembrane domain (TM), and cytoplasmic domain, (semaphorin) 6D | NM_172537, NM_199238, NM_199240, NM_199239, NM_199241 |
| Mertk | c-mer proto-oncogene tyrosine kinase | NM_008587 |
| Thbd | thrombomodulin | NM_009378 |
| Enpep | glutamyl aminopeptidase | NM_007934 |
| Npr2 | natriuretic peptide receptor 2 | NM_173788 |
| Ppap2b | phosphatidic acid phosphatase type 2B | NM_080555 |
| Clstn1 | calsyntenin 1 | NM_023051 |
| Agrn | agrin | NM_021604 |

TABLE 1B-continued

Microvessel Endothelial Cell Surface Markers

| Gene Symbol | Gene Name | Gene Accession Number |
|---|---|---|
| Cd36 | CD36 antigen | NM_001159558, NM_001159557, NM_001159556, NM_007643, NM_001159555 |
| Kdr | kinase insert domain protein receptor | NM_010612 |
| Mlec | malectin | NM_175403 |
| Gpr81 | G protein-coupled receptor 81 | NM_175520 |
| Cald1 | caldesmon 1 | NM_145575 |
| Dysf | dysferlin | NM_001077694, NM_021469 |
| Mgll | monoglyceride lipase | NM_001166251, NM_001166249, NM_011844 |
| Tspan12 | tetraspanin 12 | NM_173007 |
| Podxl | podocalyxin-like | NM_013723 |
| Plxnd1 | plexin D1 | NM_026376 |
| Kcne3 | potassium voltage-gated channel, Isk-related subfamily, gene 3 | NM_001190871, NM_001190869, NM_001190950, NM_020574, NM_001190870 |
| Lrp3 | low density lipoprotein receptor-related protein 3 | NM_001024707 |
| Aqp11 | aquaporin 11 | NM_175105 |
| F2rl3 | coagulation factor II (thrombin) receptor-like 3 | NM_007975 |
| Cdh13 | cadherin 13 | NM_019707 |
| Nrp1 | neuropilin 1 | NM_008737 |
| Dok4 | docking protein 4 | NM_053246 |
| Fxyd6 | FXYD domain-containing ion transport regulator 6 | NM_022004 |
| Ephb1 | Eph receptor B1 | NM_001168296, NM_173447 |
| Rtp3 | receptor transporter protein 3 | NM_153100 |
| Ccrl2 | chemokine (C-C motif) receptor-like 2 | NM_017466 |
| Tgfbr2 | transforming growth factor, beta receptor II | NM_029575, NM_009371 |
| Lpar4 | lysophosphatidic acid receptor 4 | NM_175271 |
| A630033H20Rik | RIKEN cDNA A630033H20 gene | NM_175442, NM_001122596, NM_001122595 |
| Kcnj2 | potassium inwardly-rectifying channel, subfamily J, member 2 | NM_008425 |
| Abca8b | ATP-binding cassette, sub-family A (ABC1), member 8b | NM_013851 |
| F2r | coagulation factor II (thrombin) receptor | NM_010169 |
| Robo2 | roundabout homolog 2 (Drosophila) | NM_175549 |
| Ms4a1 | membrane-spanning 4-domains, subfamily A, member 1 | NM_007641 |
| Arhgef26 | Rho guanine nucleotide exchange factor (GEF) 26 | NM_001081295 |
| Ttll7 | tubulin tyrosine ligase-like family, member 7 | NM_027594 |
| Clca5 | chloride channel calcium activated 5 | NM_178697 |
| Vmn1r100 | vomeronasal 1 receptor 100 | NM_001166844 |
| Vmn1r148 | vomeronasal 1 receptor 148 | NM_030736 |
| Vmn1r114 | vomeronasal 1 receptor 114 | NM_001166837 |
| Vmn1r132 | vomeronasal 1 receptor 132 | NM_001122682 |
| Vmn1r93 | vomernasal 1 receptor Vmn1r93 | NM_207547 |
| Vmn1r-ps79 | vomeronasal 1 receptor, pseudogene 79 | NR_030707 |
| Vmn1r125 | vomeronasal 1 receptor 125 | NM_001166740 |
| Epor | erythropoietin receptor | NM_010149 |
| Jam3 | junction adhesion molecule 3 | NM_023277 |
| Atp1b1 | ATPase, Na+/K+ transporting, beta 1 polypeptide | NM_009721 |
| Car4 | carbonic anhydrase 4 | NM_007607 |
| Jup | junction plakoglobin | NM_010593 |
| Lgals3bp | lectin, galactoside-binding, soluble, 3 binding protein | NM_011150 |
| Ppap2a | phosphatidic acid phosphatase type 2A | NM_008903, NM_008247 |
| Itga1 | integrin alpha 1 | NM_001033228 |
| Gpihbp1 | GPI-anchored HDL-binding protein 1 | NM_026730 |
| Slc9a3r2 | solute carrier family 9 (sodium/hydrogen exchanger), member 3 regulator 2 | NM_023055, NM_023449 |
| Sdc3 | syndecan 3 | NM_011520 |
| Aqp7 | aquaporin 7 | NM_007473 |
| Mlec | malectin | NM_175403 |

TABLE 1B-continued

Microvessel Endothelial Cell Surface Markers

| Gene Symbol | Gene Name | Gene Accession Number |
|---|---|---|
| Slc6a6 | solute carrier family 6 (neurotransmitter transporter, taurine), member 6 | NM_009320 |
| Irak2 | interleukin-1 receptor-associated kinase 2 | NM_001113553 |
| Klrb1f | killer cell lectin-like receptor subfamily B member 1F | NM_153094 |
| Cd97 | CD97 antigen | NM_001163031, NM_001163029, NM_011925, NM_001163030 |
| Gpc4 | glypican 4 | NM_008150 |
| Ramp3 | receptor (calcitonin) activity modifying protein 3 | NM_019511 |
| Olfr1396 | olfactory receptor 1396 | NM_146337 |
| Slc1a1 | solute carrier family 1 (neuronal/epithelial high affinity glutamate transporter, system Xag), member 1 | NM_009199 |
| Cldn15 | claudin 15 | NM_021719 |
| Cd109 | CD109 antigen | NM_153098 |
| Sell | selectin, lymphocyte | NM_001164059, NM_011346 |
| Cd79b | CD79B antigen | NM_008339 |
| Ly86 | lymphocyte antigen 86 | NM_010745 |
| Chrm3 | cholinergic receptor, muscarinic 3, cardiac | NM_033269 |
| Ptger4 | prostaglandin E receptor 4 (subtype EP4) | NM_008965, NM_001136079 |
| Sema7a | sema domain, immunoglobulin domain (Ig), and GPI membrane anchor, (semaphorin) 7A | NM_011352 |

The microvessel endothelial cell targeting agents described herein are capable of recognizing, binding to, or otherwise interacting with endothelial cell surface markers lining microvessels. Accordingly, in some embodiments, the microvessel endothelial cell targeting agent binds to a protein expressed on the surface of an endothelial cell lining a microvessel. In some instances, the microvessel endothelial cell targeting agent influences a physiological function of the protein itself or downstream activities of the protein (e.g., signaling pathways).

In other instances, the microvessel endothelial cell targeting agent is internalized into or transported across the endothelial cells lining the microvessel. In some embodiments, internalization of the microvessel endothelial cell targeting agent into the endothelial cells lining the microvessel causes the microvessel endothelial cell targeting agent to accumulate in a microvessel, tissue or organ adjacent to the microvessel endothelial cell. In some embodiments, the microvessel endothelial cell targeting agent accumulates in the subject's skin. In some embodiments, the microvessel endothelial cell targeting agent accumulates in the subject's adipose tissue. In some embodiments, the microvessel endothelial cell targeting agent accumulates in the venule endothelial cells in the subject's lymph nodes. In some embodiments, the microvessel endothelial cell targeting agent does not accumulate in non-target tissues. In some embodiments, negligible amounts of the microvessel endothelial cell targeting agent accumulate in non-target tissues.

In some embodiments, internalization of the microvessel endothelial cell targeting agent into the endothelial cells lining the microvessel causes the agent to accumulate in a microvessel, tissue or organ adjacent to the microvessel endothelial cell. In some embodiments, the agent accumulates in the subject's skin. In some embodiments, the agent accumulates in the subject's adipose tissue. In some embodiments, the agent accumulates in the subject's lymph nodes. In some embodiments, the agent does not accumulate in non-target tissues. In some embodiments, negligible amounts of the agent accumulate in non-target tissues.

In some instances, the agent is internalized into or transported across the endothelial cells lining the microvessel. In some embodiments, internalization or transport of the agent into the endothelial cells lining or transport across the endothelial lining of the microvessel causes the agent to accumulate in a microvessel, tissue, or organ adjacent to the microvessel endothelial cell. In some embodiments, the agent does not accumulate in non-target tissues. In some embodiments, negligible amounts of the microvessel endothelial cell targeting agent accumulate in non-target tissues.

The disclosure contemplates delivering an agent to microvessel endothelial cells for any purpose in which such delivering would be desirable. In some embodiments, delivering an agent to microvessel endothelial cells of a subject treats, prevents, or ameliorates a symptom of, a disease in the subject. In some embodiments, the disease is an inflammatory disease. In such embodiments, the agent can comprise an anti-inflammatory agent coupled to a microvessel endothelial cell targeting agent. In some embodiments, the microvessel endothelial cell targeting agent may exhibit anti-inflammatory activity, for example, by binding to an endothelial cell surface marker in the microvessel (e.g., venules) in a way that interferes with leukocyte trafficking, adhesion, and/or extravasation into the extravascular compartment surrounding the microvessel (e.g., a target tissue).

The disclosure contemplates treating, preventing, or ameliorating a symptom of, any inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some embodiments, the disease is a microvasculature disease. In some embodiments, the microvasculature disease is a venular disease. As used herein, "venular disease" refers to a disease associated with, involving, originating in, or otherwise affecting venules. The disclosure contemplates treating any venular disease in which delivering a microvessel endothelial cell targeting agent to a subject would be desirable. Exemplary venular diseases include, but are not limited to, high endothelial venules, rheumatoid arthritis, chronic inflammation associated with high endothelial venules, inflammatory bowel diseases (Crohn's disease, ulcerative colitis, autoimmune thyroiditis (Graves' disease and Hashimoto's thyroiditis), venule occlusion, small vessel disease, cardiovascular disease associated with small vessel disease, age-related small vessel diseases, hypertension-related small vessel diseases, and cerebral amyloid angiopathy.

In some embodiments, the microvasculature disease is a non-venular disease. As used herein, "non-venular disease" refers to a disease associated with, involving, originating in, or otherwise affecting non-venules. The disclosure contemplates treating any venular disease in which delivering a microvessel endothelial cell targeting agent to a subject would be desirable. Examples of such non-venular diseases include, but are not limited to, small vessel coronary disease (e.g., cardiac syndrome X, microvascular dysfunction, non-obstructive coronary disease, and microvascular angina), thrombotic microangiopathy, microangiopathic haemolytic anaemia, microvascular occlusion, cutaneous diabetic microagniopathy, Susac's syndrome, cerebral microangiopathy, early diabetic microangiopathy, diabetic microangiopathy, glomerular microangiopathy, non-neoplastic nevus, pulmonary microangiopathy, pulmonary capillaritis (e.g., isolated pauci-immune pulmonary capillaritis), coronary microvascular disease, chronic microvascular diseases, small vessel ischemia, thrombotic thrombocytopenic purpura, arteriolosclerosis, and arterioloephosclerosis, teleangiectasia (e.g., hereditary hemorrhagic telangiectasia), and scleroderma.

The disclosure contemplates delivering agents to any microvessel in which delivering an agent to endothelium would be desirable.

Targeting Venules

In some aspects, the disclosure contemplates targeting venules. In an aspect, disclosed herein is a method of delivering an agent to a venule endothelial cell in a subject. An exemplary method of delivering an agent to a venule endothelial cell in a subject comprises administering to the subject a venule endothelial cell targeting agent which binds to a protein expressed on the surface of a venule endothelial cell.

In some embodiments, the venule endothelial cell targeting agent causes an effect in the venule endothelial cell, or venule, tissue, or organ adjacent to the venule endothelial cell. In some embodiments, the venule endothelial cell targeting agent is coupled to an agent which causes an effect in the venule endothelial cell, or a venule, tissue or organ adjacent to the venule endothelial cell.

As used herein, "venule endothelial cell targeting agent" refers to a targeting agent that is capable of targeting endothelial cells lining a venule by binding to a venule endothelial cell surface marker described herein (e.g., a protein expressed on the surface of a venule endothelial cell). In some embodiments, the protein expressed on the surface of the venule endothelial cell is encoded by a gene exhibiting higher expression levels in venule endothelial cells compared to non-venule endothelial cells. Exemplary genes which exhibit higher expression levels in venule endothelial cells compared to non-venule endothelial cells include, but are not limited to, Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap11, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. Exemplary genes which exhibit higher expression levels in venule endothelial cells compared to non-venule endothelial cells also include, but are not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

The venule endothelial cell targeting agents described herein are capable of recognizing, binding to, or otherwise interacting with endothelial cell surface markers lining venules. Accordingly, in some embodiments, the venule endothelial cell targeting agent binds to a protein expressed on the surface of an endothelial cell lining a venule. In some instances, the venule endothelial cell targeting agent influences a physiological function of the protein itself or downstream activities of the protein (e.g., signaling pathways).

In other instances, the venule endothelial cell targeting agent is internalized into or transported across the endothelial cells lining the venule. In some embodiments, internalization of the venule endothelial cell targeting agent into the endothelial cells lining the venule causes the venule endothelial cell targeting agent to accumulate in a venule, tissue or organ adjacent to the venule endothelial cell expressing the venule endothelial cell surface marker. In some embodiments, the venule endothelial cell targeting agent accumulates in the subject's skin. In some embodiments, the venule endothelial cell targeting agent accumulates in the subject's adipose tissue. In some embodiments, the venule endothelial cell targeting agent accumulates in the venule endothelial cells in the subject's lymph nodes. In some embodiments, the venule endothelial cell targeting agent does not accumulate in non-target tissues. In some embodiments, negligible amounts of the venule endothelial cell targeting agent accumulate in non-target tissues.

In some embodiments, internalization of the venule endothelial cell targeting agent into the endothelial cells lining the venule causes the agent to accumulate in a venule, tissue or organ adjacent to the venule endothelial cell. In some embodiments, the agent accumulates in the subject's skin. In some embodiments, the agent accumulates in the subject's adipose tissue. In some embodiments, the agent accumulates in the subject's lymph nodes. In some embodiments, the agent does not accumulate in non-target tissues. In some embodiments, negligible amounts of the agent accumulate in non-target tissues.

In some instances, the agent is internalized into or transported across the endothelial cells lining the venule. In some embodiments, internalization of the agent into the endothelial cells lining or transport across the endothelial lining of the venule causes the agent to accumulate in a venule, tissue, or organ adjacent to the venule endothelial cells. In some embodiments, the agent does not accumulate in non-target tissues. In some embodiments, negligible amounts of the venule endothelial cell targeting agent accumulate in non-target tissues.

The disclosure contemplates delivering an agent to venule endothelial cells for any purpose in which such delivering would be desirable. In some embodiments, delivering an agent to venule endothelial cells of a subject treats, prevents, or ameliorates a symptom of, a disease in the subject.

In some embodiments, the disease is venular disease. Exemplary venular diseases include, but are not limited to, high endothelial venules, rheumatoid arthritis, chronic inflammation associated with high endothelial venules, inflammatory bowel diseases (Crohn's disease, ulcerative colitis, autoimmune thyroiditis (Graves' disease and Hashimoto's thyroiditis), venule occlusion, small vessel disease, cardiovascular disease associated with small vessel disease, age-related small vessel diseases, hypertension-related small vessel diseases, and cerebral amyloid angiopathy.

In some embodiments, the disease is an inflammatory disease. In such embodiments, the agent can comprise an anti-inflammatory agent coupled to a venule endothelial cell targeting agent. In some embodiments, the venule endothelial cell targeting agent may exhibit anti-inflammatory activity, for example, by binding to an endothelial cell surface marker in the venule in a way that interferes with leukocyte trafficking, adhesion, and/or extravasation into the extravascular compartment surrounding the venule (e.g., a target tissue).

The disclosure contemplates treating, preventing, or ameliorating a symptom of, any inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parasitic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

Methods for Targeting Non-Venules

In some aspects, the disclosure contemplates targeting non-venules. In an aspect, the disclosure provides a method of delivering an agent to a non-venule endothelial cell in a subject. An exemplary method of delivering an agent to a non-venule endothelial cell in a subject comprises administering to the subject a non-venule endothelial cell targeting agent which binds to a protein expressed on the surface of a non-venule endothelial cell.

In some embodiments, the non-venule endothelial cell targeting agent causes an effect in the non-venule endothelial cell, or non-venule, tissue, or organ adjacent to the non-venule endothelial cell. In some embodiments, the non-venule endothelial cell targeting agent is coupled to an agent which causes an effect in the non-venule endothelial cell, or a non-venule, tissue or organ adjacent to the non-venule endothelial cell.

As used herein, "non-venule endothelial cell targeting agent" refers to a targeting agent that is capable of targeting endothelial cells lining a non-venule by binding to a non-venule endothelial cell surface marker described herein (e.g., a protein expressed on the surface of a non-venule endothelial cell). In some embodiments, the protein expressed on the surface of the non-venule endothelial cell is encoded by a gene exhibiting higher expression levels in non-venule endothelial cells compared to venule endothelial cells. Exemplary genes which exhibit higher expression levels in non-venule endothelial cells compared to venule endothelial cells include, but are not limited to, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. Exemplary genes which exhibit higher expression levels in non-venule endothelial cells compared to venule endothelial cells also include, but are not limited to, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

The non-venule endothelial cell targeting agents described herein are capable of recognizing, binding to, or otherwise interacting with endothelial cell surface markers lining non-venules. Accordingly, in some embodiments, the non-venule endothelial cell targeting agent binds to a protein expressed on the surface of an endothelial cell lining a non-venule. In some instances, the non-venule endothelial cell targeting agent influences a physiological function of the protein itself or downstream activities of the protein (e.g., signaling pathways).

In other instances, the non-venule endothelial cell targeting agent is internalized into or transported across the endothelial cells lining the non-venule. In some embodiments, internalization of the non-venule endothelial cell targeting agent into the endothelial cells lining the non-venule causes the non-venule endothelial cell targeting agent to accumulate in a non-venule, tissue or organ adjacent to the non-venule endothelial cell expressing the non-venule endothelial cell surface marker. In some embodiments, the non-venule endothelial cell targeting agent accumulates in the subject's skin. In some embodiments, the non-venule endothelial cell targeting agent accumulates in the subject's adipose tissue. In some embodiments, the non-venule endothelial cell targeting agent accumulates in the non-venule endothelial cells in the subject's lymph nodes. In some embodiments, the non-venule endothelial cell targeting agent does not accumulate in non-target tissues. In some embodiments, negligible amounts of the non-venule endothelial cell targeting agent accumulate in non-target tissues.

In some embodiments, internalization of the non-venule endothelial cell targeting agent into the endothelial cells lining the non-venule causes the agent to accumulate in a non-venule, tissue or organ adjacent to the non-venule endothelial cell. In some embodiments, the agent accumulates in the subject's skin. In some embodiments, the agent accumulates in the subject's adipose tissue. In some embodiments, the agent accumulates in the subject's lymph nodes. In some embodiments, the agent does not accumulate in non-target tissues. In some embodiments, negligible amounts of the agent accumulate in non-target tissues.

In some instances, the agent is internalized into or transported across the endothelial cells lining the non-venule. In some embodiments, internalization of the agent into the endothelial cells lining or transport across the endothelial lining of the non-venule causes the agent to accumulate in a non-venule, tissue, or organ adjacent to the non-venule endothelial cells. In some embodiments, the agent does not accumulate in non-target tissues. In some embodiments, negligible amounts of the non-venule endothelial cell targeting agent accumulate in non-target tissues.

The disclosure contemplates delivering an agent to non-venule endothelial cells for any purpose in which such delivering would be desirable. In some embodiments, delivering an agent to non-venule endothelial cells of a subject treats, prevents, or ameliorates a symptom of, a disease in the subject.

In some embodiments, the disease is an inflammatory disease. In such embodiments, the agent can comprise an anti-inflammatory agent coupled to a non-venule endothelial cell targeting agent.

The disclosure contemplates treating, preventing, or ameliorating a symptom of, any inflammatory disease. In some embodiments, the inflammatory disease is selected from the group consisting of endotoxemia, sepsis, cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, sleep apnea, atherosclerosis, inflammatory bowel disease, rheumatoid arthritis, vasculitis, transplant rejection, asthma, ischaemic heart disease, appendicitis, peptic, gastric and duodenal ulcers, peritonitis, pancreatitis, ulcerative, pseudomembranous, acute and ischemic colitis, diverticulitis, epiglottitis, achalasia, cholangitis, hepatitis, Crohn's disease, enteritis, Whipple's disease, allergy, anaphylactic shock, immune complex disease, organ ischemia, reperfusion injury, organ necrosis, hay fever, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, a parastic infection, a bacterial infection, a viral infection, an autoimmune disease, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, thrombophlebitis, pericarditis, myocarditis, myocardial ischemia, periarteritis nodosa, rheumatic fever, celiac disease, adult respiratory distress syndrome, meningitis, encephalitis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, periodontal disease, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, Retier's syndrome, and Hodgkins disease.

In some embodiments, the disease is non-venular disease. Examples of non-venular diseases contemplated by the disclosure include, but are not limited to, small vessel coronary disease (e.g., cardiac syndrome X, microvascular dysfunction, non-obstructive coronary disease, and microvascular angina), thrombotic microangiopathy, microangiopathic haemolytic anaemia, microvascular occlusion, cutaneous diabetic microagniopathy, Susac's syndrome, cerebral microangiopathy, early diabetic microangiopathy, diabetic microangiopathy, glomerular microangiopathy, non-neoplastic nevus, pulmonary microangiopathy, pulmonary capillaritis (e.g., isolated pauci-immune pulmonary capillaritis), coronary microvascular disease, chronic microvascular diseases, small vessel ischemia, thrombotic thrombocytopenic purpura, arteriolosclerosis, and arterioloephosclerosis, teleangiectasia (e.g., hereditary hemorrhagic telangiectasia), and scleroderma.

The disclosure also contemplates targeting agents to microvessels in a tissue-specific manner.

Methods of Targeting Skin

In aspects, the agents are targeted to microvessels in skin. In an aspect, disclosed herein is a method of delivering an agent to a microvessel endothelial cell in skin. An exemplary method of delivering an agent to a microvessel endothelial cell in skin comprises administering to a subject a skin microvessel endothelial cell targeting agent which binds to a protein expressed on the surface of a microvessel endothelial cell in skin. In some embodiments, the skin microvessel endothelial cell targeting agent causes an effect in the skin microvessel endothelial cell, or microvessel, tissue, or organ adjacent to the skin microvessel endothelial cell. In some embodiments, the skin microvessel endothelial cell targeting agent is coupled to an agent which causes an effect in the skin microvessel endothelial cell, or microvessel, tissue, or organ adjacent to the skin microvessel endothelial cell.

As used herein, "skin endothelial cell targeting agent" refers to a targeting agent that is capable of targeting endothelial cells lining skin microvessels by binding to a skin microvessel endothelial cell surface marker described herein (e.g., a protein expressed on the surface of a skin microvessel endothelial cell).

In some embodiments, the microvessel in the subject's skin comprises a venule (e.g., the venules to be specifically targeted are skin venules). In such embodiments, the skin microvessel endothelial cell targeting agent comprises a skin venule endothelial cell targeting agent. In such embodiments, the protein is encoded by a gene exhibiting higher expression levels in skin venule endothelial cells compared to skin non-venule endothelial cells. Examples of such genes include, but are not limited to, Nrp2, Gpr1, C630004H02Rik, Fndc1, 2310046K01Rik, Insr, and Slco2a1. Examples of such genes also include, but are not limited to, Nrp2, Htr2b, Mr1, Lifr, Anxa1, Lphn2, Vamp5, Olr1, Eps8, Slco2b1, and Slco2a1.

In some embodiments, the microvessel in the subject's skin comprises a non-venule (e.g., the non-venules to be specifically targeted are skin non-venules). In such embodiments, the skin microvessel endothelial cell targeting agent comprises a skin non-venule endothelial cell targeting agent. In such embodiments, the protein is encoded by a gene exhibiting higher expression levels in skin non-venule endothelial cells compared to skin venule endothelial cells. Examples of such genes include, but are not limited to Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. Examples of such genes also include, but are not limited to Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

The skin microvessel endothelial cell targeting agents described herein are capable of recognizing, binding to, or otherwise interacting with skin endothelial cell surface markers lining skin microvessels. Accordingly, in some embodiments, the skin microvessel endothelial cell targeting agent binds to a protein expressed on the surface of an endothelial cell lining a microvessel in the subject's skin. In some instances, the skin microvessel endothelial cell targeting agent influences a physiological function of the protein itself or downstream activities of the protein (e.g., signaling pathways).

In other instances, the skin microvessel endothelial cell targeting agent is internalized into or transported across the endothelial cells lining a microvessel in the subject's skin. In some embodiments, internalization of the skin microvessel endothelial cell targeting agent into the endothelial cells lining the microvessel in the subject's skin causes the skin microvessel endothelial cell targeting agent to accumulate in the subject's skin. In some embodiments, the skin microvessel endothelial cell targeting agent does not accumulate in tissues other than skin. In some embodiments, the negligible amounts of the skin microvessel endothelial cell targeting agent accumulate in tissues other than skin.

In some embodiments, internalization of the skin microvessel endothelial cell targeting agent into the endothelial cells lining the microvessel in the subject's skin causes the agent to be internalized into or transported across the endothelial cells lining the microvessel in the subject's skin. In some embodiments, internalization or transport of the agent causes the agent to accumulate in the subject's skin. In some embodiments, the agent does not accumulate in tissues other than skin. In some embodiments, negligible amounts of the agent accumulate in tissues other than skin.

In some embodiments, the agent is internalized into or transported across the endothelial cells lining a microvessel in the subject's skin. In some embodiments, internalization or transport of the agent causes the agent to accumulate in the subject's skin. In some embodiments, the agent does not accumulate in tissues other than skin. In some embodiments, only negligible amounts of the agent accumulate in tissues other than skin.

The disclosure contemplates targeting an agent to skin microvessel endothelial cells for any purpose in which such targeting would be desirable. In some embodiments, targeting an agent to skin microvessel endothelial cells of a subject treats, prevents, or ameliorates a symptom of, a disease in the subject.

In some embodiments, the disease is a skin disease. The disclosure contemplates treating, preventing, or ameliorating a symptom of, any skin disease. In some embodiments, the disease is a skin disease selected from the group consisting of acne, alopecia (e.g., alopecia areata, alopecia totalis, alopecia universalis, traction alopecia), angioma, athlete's foot, basal cell carcinoma, bed sore, Behcet's Disease, blepharitis, boil, calluses and corns, canker sore, carbuncles, candidiasis (e.g., oral (oral thrush), vaginal (candidal vulvovaginitis), penile (candidal balanitis), in the diaper area (diaper rash), in the skin folds (candidal intertrigo), cellulitis, cold sores, creeping eruption, dandruff, dermatitis (eczema) (e.g., atopic dermatitis, contact dermatitis, seborrhoeic dermatitis, cradle cap, nummular dermatitis, stasis dermatitis, perioral dermatitis (muzzle rash), dermatitis herpetiformis), dermatofibroma, Bowen's Disease, bullous pemphigoid, echtima, eczema, epidermolysis bullosa (e.g., simplex, junctional, dystrophic, hemidesmosomal), erythrasma, erysipelas, folliculitis, friction blisters, herpes (e.g., HHV1 i.e., cold sores, HHV2 i.e., genital herpes, HHV3, e.g., chickenpox, shingles, HHV6, HHV7, e.g., roseola infantum, sixth disease, HHV8, i.e., Kaposi's sarcoma herpesvirus), hidradenitis suppurativa, hives, hyperhidrosis, ichthyosis, impetigo, jock itch, Kaposi's sarcoma, keloid, keratoacanthoma, keratosis (e.g., actinic (solar) keratosis, keratosis pilaris, keratosis follicularis (Daffier's disease), seborrheic, and hyperkeratosis), lice infection, lichen planus, lichen simplex chronicus, lipoma, lymphadenitis, malignant melanoma, melisma, miliaria, molluscum contagiosum, Paget's disease of the nipple, pediculosis, pemphigus, photoallergy, photosensitivity, *pityriasis rosea*, *pityriasis rubra* pilaris, psoriasis, Raynaud's disease, ring worm, Raynaud's disease, rosacea, Saint Anthony's fire, scabies, scleroderma, sebaceous cyst, shingles, skin cancer, skin tags, spider veins (telangiectasia), squamous cell carcinoma, tick bite, tinea: (barbae, capitis, corporis, cruris (Jock Itch), pedis unguium, *versicolor*), trichomycosis, varicose veins, vitiligo, warts (e.g., common, planar, genital).

In some embodiments, the disease is a skin inflammatory disease. The disclosure contemplates treating, preventing, or ameliorating a symptom of, any skin inflammatory disease. In some embodiments, the skin inflammatory disease is selected from the group consisting of acne, dermatitis, eczema, oily skin, rosacea, cutaneous lymphoma and urticaria. In some embodiments, the dermatitis is selected from the group consisting of atopic dermatitis, psoriasis and contact dermatitis.

Methods of Targeting Adipose

In some aspects, the agents are targeted to microvessel in adipose tissue. In an aspect, disclosed herein is a method of delivering an agent to a microvessel endothelial cell in adipose tissue. An exemplary method of delivering an agent to a microvessel endothelial cell in adipose tissue comprises administering to a subject an adipose tissue microvessel endothelial cell targeting agent which binds to a protein expressed on the surface of a microvessel endothelial cell in adipose tissue.

In some embodiments, the adipose tissue microvessel endothelial cell targeting agent causes an effect in the adipose tissue microvessel endothelial cell, or microvessel, tissue, or organ adjacent to the adipose tissue microvessel endothelial cell. In some embodiments, the adipose tissue microvessel endothelial cell targeting agent is coupled to an agent which causes an effect in the adipose tissue microvessel endothelial cell, or microvessel, tissue, or organ adjacent to the adipose tissue microvessel endothelial cell.

As used herein, "adipose tissue endothelial cell targeting agent" refers to a targeting agent that is capable of targeting endothelial cells lining adipose tissue microvessels by binding to an adipose tissue microvessel endothelial cell surface marker described herein (e.g., a protein expressed on the surface of an adipose tissue microvessel endothelial cell).

In some embodiments, the microvessel in the subject's adipose tissue comprises a venule (e.g., the venules to be specifically targeted are adipose tissue venules). In such embodiments, the adipose tissue microvessel endothelial cell targeting agent comprises an adipose tissue venule endothelial cell targeting agent. In such embodiments, the protein is encoded by a gene exhibiting higher expression levels in adipose tissue venule endothelial cells compared to adipose tissue non-venule endothelial cells. Examples of such genes include, but are not limited to, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. Examples of such genes also include, but are not limited to, Il1rl1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the microvessel in the subject's adipose tissue comprises a non-venule (e.g., the non-venules to be specifically targeted are adipose tissue non-venules). In such embodiments, the adipose tissue microvessel endothelial cell targeting agent comprises an adipose tissue non-venule endothelial cell targeting agent. In such embodiments, the protein is encoded by a gene exhibiting higher expression levels in adipose tissue non-venule endothelial cells compared to adipose tissue venule endothelial cells. Examples of such genes include, but are not limited to, Adora2a, H2-Ab1, Hspg2, Gpr81, Kcna5, Jam3, and Gpc4. Examples of such genes also include, but are not limited to, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

The adipose tissue microvessel endothelial cell targeting agents described herein are capable of recognizing, binding to, or otherwise interacting with adipose tissue endothelial cell surface markers lining adipose tissue microvessels. Accordingly, in some embodiments, the adipose tissue microvessel endothelial cell targeting agent binds to a protein expressed on the surface of an endothelial cell lining a microvessel in the subject's adipose tissue. In some instances, the adipose tissue microvessel endothelial cell targeting agent influences a physiological function of the protein itself or downstream activities of the protein (e.g., signaling pathways).

In other instances, the adipose tissue microvessel endothelial cell targeting agent is internalized into or transported across the endothelial cells lining a microvessel in the subject's adipose tissue. In some embodiments, internalization of the adipose tissue microvessel endothelial cell targeting agent into the endothelial cells lining the microvessel in the subject's adipose tissue causes the adipose tissue microvessel endothelial cell targeting agent to accumulate in the subject's adipose tissue. In some embodiments, the adipose tissue microvessel endothelial cell targeting agent does not accumulate in tissues other than adipose tissue. In some embodiments, negligible amounts of the adipose tissue microvessel endothelial cell targeting agent accumulate in tissues other than adipose tissue.

In some embodiments, internalization of the adipose tissue microvessel endothelial cell targeting agent into the endothelial cells lining the microvessel in the subject's adipose tissue causes the agent to be internalized into or transported across the endothelial cells lining the microvessel in the subject's adipose tissue. In some embodiments, internalization or transport of the agent causes the agent to accumulate in the subject's adipose tissue. In some embodiments, the agent does not accumulate in tissues other than adipose tissue. In some embodiments, negligible amounts of the agent accumulate in tissues other than adipose tissue.

In some embodiments, the agent is internalized into or transported across the endothelial cells lining a microvessel in the subject's adipose tissue. In some embodiments, internalization or transport of the agent causes the agent to accumulate in the subject's adipose tissue. In some embodiments, the agent does not accumulate in tissues other than adipose tissue. In some embodiments, only negligible amounts of the agent accumulate in tissues other than adipose tissue.

The disclosure contemplates targeting an agent to adipose tissue microvessel endothelial cells for any purpose in which such targeting would be desirable. In some embodiments, targeting an agent to adipose tissue microvessel endothelial cells of a subject treats, prevents, or ameliorates a symptom of, a disease in the subject. In some embodiments, the disease is an adipose tissue disease. The disclosure contemplates treating, preventing, or ameliorating a symptom of, any adipose tissue disease. Examples of adipose tissue diseases include, but are not limited to, obesity and related disorders, including, for example cancer, cellulitis, chronic renal failure, depression, diabetes, erectile dysfunction, fatty liver disease, gallbladder disease (e.g., gallstones), gastroesophageal reflux disease, gout, heart disease (e.g., congestive heart failure, enlarged heart), hernia, high blood pressure, hypercholesterolemia, infection, infertility, lymph edema, osteoarthritis, pain, Pickwickian syndrome, pulmonary embolism, polycystic ovarian syndrome, ulcers, stroke, and urinary incontinence. In some embodiments, the disease is a disease characterized by inflammation in the subject's visceral fat. The disclosure contemplates treating, preventing, or ameliorating a symptom of, any disease characterized by visceral fat inflammation. In some embodiments, the disease is selected from the group consisting of cancer, CVHD, fibrosis, hypertension, lypodystrophy, obesity, metabolic syndrome, and diabetes (e.g., type II diabetes).

Methods of Targeting Lymph Nodes

In some embodiments, the agents are targeted to microvessels in lymph nodes. In an aspect, disclosed herein is a method of delivering an agent to a microvessel endothelial cell in lymph nodes. An exemplary method of delivering an agent to a microvessel endothelial cell in a lymph nodes comprises administering to a subject a lymph node microvessel endothelial cell targeting agent which binds to a protein expressed on the surface of a microvessel endothelial cell in the lymph nodes.

In some embodiments, the lymph node microvessel endothelial cell targeting agent causes an effect in the lymph node microvessel endothelial cell, or microvessel, tissue, or organ adjacent to the lymph node microvessel endothelial cell. In some embodiments, the lymph node microvessel endothelial cell targeting agent is coupled to an agent which causes an effect in the lymph node microvessel endothelial cell, or microvessel, tissue, or organ adjacent to the lymph node microvessel endothelial cell.

As used herein, "lymph node endothelial cell targeting agent" refers to a targeting agent that is capable of targeting endothelial cells lining lymph node microvessels by binding to a lymph node microvessel endothelial cell surface marker described herein (e.g., a protein expressed on the surface of a lymph node microvessel endothelial cell).

In some embodiments, the microvessel in the subject's lymph node comprises a venule (e.g., the venules to be specifically targeted are lymph node venules). In such embodiments, the lymph node microvessel endothelial cell targeting agent comprises a lymph node venule endothelial cell targeting agent. In such embodiments, the protein is encoded by a gene exhibiting higher expression levels in lymph node venule endothelial cells compared to lymph node non-venule endothelial cells. Examples of such genes include, but are not limited to Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. Examples of such genes also include, but are not limited to, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the microvessel in the subject's lymph node comprises a non-venule (e.g., the non-venules to be specifically targeted are lymph node non-venules). In such embodiments, the lymph node microvessel endothelial cell targeting agent comprises a lymph node non-venule endothelial cell targeting agent. In such embodiments, the protein is encoded by a gene exhibiting higher expression levels in lymph node non-venule endothelial cells compared to lymph node venule endothelial cells. Examples of such genes include, but are not limited to, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. Examples of such genes also include, but are not limited to, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

The lymph node microvessel endothelial cell targeting agents described herein are capable of recognizing, binding to, or otherwise interacting with lymph node endothelial cell surface markers lining lymph node microvessels. Accordingly, in some embodiments, the lymph node microvessel endothelial cell targeting agent binds to a protein expressed on the surface of an endothelial cell lining a microvessel in the subject's lymph nodes. In some instances, the lymph node microvessel endothelial cell targeting agent influences a physiological function of the protein itself or downstream activities of the protein (e.g., signaling pathways).

In other instances, the lymph node microvessel endothelial cell targeting agent is internalized into or transported across the endothelial cells lining a microvessel in the subject's lymph nodes. In some embodiments, internalization of the lymph node microvessel endothelial cell targeting agent into the endothelial cells lining the microvessel in the subject's lymph nodes causes the lymph node microvessel endothelial cell targeting agent to accumulate in the subject's lymph nodes. In some embodiments, the lymph node microvessel endothelial cell targeting agent does not accumulate in tissues other than lymph nodes. In some embodiments, negligible amounts of the lymph node microvessel endothelial cell targeting agent accumulate in tissues other than lymph nodes.

In some embodiments, internalization of the lymph node microvessel endothelial cell targeting agent into the endothelial cells lining the microvessel in the subject's lymph nodes causes the agent to be internalized into or transported across the endothelial cells lining the microvessel in the subject's lymph nodes. In some embodiments, internalization or transport of the agent causes the agent to accumulate in the subject's lymph nodes. In some embodiments, the agent does not accumulate in tissues other than lymph nodes. In some embodiments, negligible amounts of the agent accumulate in tissues other than lymph nodes.

In some embodiments, the agent is internalized into or transported across the endothelial cells lining a microvessel in the subject's lymph nodes. In some embodiments, internalization or transport of the agent causes the agent to accumulate in the subject's lymph nodes. In some embodiments, the agent does not accumulate in tissues other than lymph nodes. In some embodiments, only negligible amounts of the agent accumulate in tissues other than lymph nodes.

The disclosure contemplates targeting an agent to lymph node microvessel endothelial cells for any purpose in which such targeting would be desirable. In some embodiments, targeting an agent to lymph node microvessel endothelial cells of a subject treats, prevents, or ameliorates a symptom of, a disease. In some embodiments, the disease is a lymph node disease. The disclosure contemplates the treatment, prevention, or amelioration of a symptom of, any lymph node disease. In some embodiments, the lymph node disease is selected from the group consisting of lymphoma, Hodgkins disease, tuberculosis, kikuchi disease, metastatic lymph node disease, lymphatic filiaris, mesenteric lymphadenitis, Castleman disease, lymphadenopathy, infiltration of the lymph nodes by metabolite-laden macrophages (e.g., lipid storage disorders such as Gaucher disease or Niemann-Pick disease, histiocytosis, cancer, lymphoid leukemia, splenomegaly, e.g., caused by sickle cell anemia, sarcoidosis, malaria, bacterial endocarditis, leukemia, pernicious anemia, Gaucher's disease, leishmaniasis, Hodgkin's disease, Banti's disease, hereditary spherocytosis, cysts, glandular fever, asplenia, hemangiomas, and hemangiosarcomas.

In some embodiments, the disease is a disease characterized by lymphadenitis. The disclosure contemplates the treatment, prevention, or amelioration of a symptom of, any disease characterized by lymphadenitis. In some embodiments, the disease is cancer (e.g., leukemias, lymphomas, and metastatic cancer). In some embodiments, the disease is a connective tissue disorder (e.g., systemic lupus erythematosus (SLE), sarcoidosis, Kawasaki disease, juvenile idiopathic arthritis, Kikuchi lymphadenopathy, rheumatoid arthritis, and Sjögren syndrome). In some embodiments, the disease is an infection (e.g., a bacterial or viral infection). Examples of such infections include, but are not limited to, upper respiratory tract infections, oropharyngeal infections, mononucleosis, tuberculosis, HIV, herpes simplex, chlamydial infections, syphilis, cellulitis, abscess of skin or soft-tissue, cat scratch disease, toxoplasmosis, brucellosis, cytomegalovirus infection, histoplasmosis, paracoccidioimycosis, plague, rat bite fever, and tularemia. In some embodiments, the oropharyngeal infection is selected from the group consisting of pharyngitis, stomatitis, and dental abscess.

Binding Partners

In some aspects, disclosed herein are binding partners specific for an endothelial cell surface marker described herein. Exemplary binding partners include binding partners specific for an endothelial cell surface marker selected from the group consisting of: (1) a microvessel endothelial cell surface marker selected from the group consisting of Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4; Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, Cd74; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enepp, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a; (2) a venule endothelial cell surface marker selected from the group consisting of Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1; (3) a non-venule endothelial cell surface marker selected from the group consisting of Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74; and/or Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enepp, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a; (4) a skin microvessel endothelial cell surface marker selected from the group consisting of Nrp2, Gpr1, C630004H02Rik, Fndc1, 2310046K01Rik, Insr, Slco2a1, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Nrp2, Htr2b, Mr1, Lifr, Anxa1, Lphn2, Vamp5, Olr1, Eps8, Slco2b1, Slco2a1, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (5) an adipose tissue microvessel endothelial cell surface marker selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Adora2a, H2-Ab1, Hspg2, Gpr81, Kcna5, Jam3, and Gpc4; and/or Il1rl1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; (6) a lymph node microvessel endothelial cell surface marker selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

In some embodiments, the binding partner is an antibody specific for an endothelial cell surface marker described herein. The skilled artisan will appreciate that the binding partners (e.g., antibodies) described herein can be used for a variety of purposes (e.g., identifying venules, for example, by conjugating a detectable label or reporter moiety to the binding partner). In some embodiments, the binding partner (e.g., antibody) is used in FACS.

Exemplary antibodies include, but are not limited to, polyclonal antibodies, monoclonal antibodies, chimeric antibodies, single-chain antibodies, antibody fragments, humanized antibodies, multi-specific antibodies, and modified antibodies.

In some embodiments, the binding partner comprises an aptide.

Screening Methods

The disclosure contemplates various screening methods using the microvessel endothelial cell surface markers described herein. Generally, test agents can be assessed for their ability to recognize, bind to, or otherwise interact with microvessel endothelial cell surface markers described herein, and internalization and/or accumulation of the test agents in the microvessel endothelial cells expressing those markers, or accumulation in a microvessel, tissue, or organ surrounding the microvessel endothelial cell surface markers can be measured. Identification of agents that target microvessel endothelial cells (e.g., by binding to a protein expressed on the surface of a microvessel endothelial cell) can be used to deliver agents to microvessel endothelial cells for use in methods of treatment, diagnosis, and/or imaging.

A variety of techniques are available to the skilled artisan to identify or screen for agents that bind to, recognize, or otherwise interact with a microvessel endothelial cell surface marker described herein (e.g., high-throughput screening, combinatorial chemistry, in silico screening, etc.). The disclosure contemplates the use of any such technique.

In some aspects, the disclosure contemplates methods for screening for microvessel endothelial cell targeting agents that recognize, bind to or otherwise interact with the microvessel endothelial cell surface markers identified herein. Generally, the candidate targeting agents may be selected from, for example, antibodies, antibody fragment, small peptides, small molecules (organic and non-organic), oligonucleotides, aptamers selected via screens of small combinatorial libraries and fusion proteins. The targeting agents may influence physiological function of the surface markers by inhibiting or augmenting (partially or fully) downstream activities of the identified surface markers. That is, for example, by influencing signaling pathways that are activated, increased, decreased or inhibited by the identified surface markers. The agents may or may not work by entering the cell and directly or indirectly interacting with constituents of the downstream pathway(s). Agents that work without entering the cell may work by inducing or inhibiting (fully or partly) other competing pathways via interaction with other cell surface molecules or with agents that interact with other cell surface molecules. Agents that work by entering the cell may work by interacting with downstream elements or molecules that interact with downstream elements. Additionally, agents that affect transcription and/or translation of the identified cell surface markers, competing markers or pathway constituents may also influence the activities of the identified cell surface markers. It is noted here that the phrase "competes with" or similar, may mean working in opposition to the identified marker and associated pathway to partly or fully inhibit the activity; likewise, the phrase may mean working in conjunction with the identified marker and associated pathway to partly or fully augment the activity. Both meanings are assumed unless noted differently herein by the context in which the phrase is used.

An exemplary screening method for identifying targeting agents is a yeast two-hybrid system (commercially available from Clontech) which allows for the detection of protein-protein interactions in yeast. See generally, Ausubel, et al., Current Protocols in Molecular Biology (John Wiley & Sons) (pp. 13.14.1-13.14.14). The system can be used to screen specially constructed cDNA libraries for proteins that interact with a target protein (e.g., a microvessel endothelial cell surface marker described herein). The disclosure contemplates the use of the two-hybrid system to screen for agents that will bind to a protein (e.g., a microvessel endothelial cell surface marker described herein). Agents (e.g., proteins) identified in a two-hybrid screen which bind to the protein (e.g., microvessel endothelial cell surface marker) may represent agents capable of blocking or augmenting the signaling of the protein (e.g., microvessel endothelial cell surface marker).

The disclosure contemplates using phage display selection to identify aptides that show high affinity and selectivity for a target protein (e.g., an endothelial cell surface marker described herein). As used herein, "aptide" refers to a scaffold-based affinity molecule that demonstrates high affinity (e.g., less than 100 nM) and selectivity for a specific protein. In certain embodiments, aptides can be synthesized to include a "tweezer-like" structure comprising a unique central structure-stabilizing scaffolding region flanked by two high-affinity target-binding components. Aptides specific for a target protein (e.g., an endothelial cell surface marker described herein) can be identified by screening an aptide-based phage library for target protein-specific ligands. In certain embodiments, the aptides comprise an amino acid sequence having a length of 24 amino acid residues. In certain embodiments, the unique central structure-stabilizing scaffolding comprises 12 amino acid residues. In certain embodiments, each of the flanking high-affinity target-binding components comprises 6 amino acid residues, which may be the same or different. Preferably, aptides possessing nanomolar-range binding affinity for the target protein are identified. Additional information about aptides can be found in the literature (see e.g., Sangyong Jon, et al., "HER2-specific aptide conjugated magneto-nanoclusters for potential breast cancer imaging and therapy," *J. Materials Chemistry B*. 2013; DOI: 10.1039/C3TB20613K; Jon, et al., "Fibronectin extra domain B-specific aptide conjugated nanoparticles for targeted cancer imaging," *J. Control Release*. 2012; 163(2):111-8; Kim, et al., "VEGF-binding aptides and the inhibition of choroidal and retinal neovascularization," *Biomaterials*. 2014; 35(9): 3052-9). Candidate aptides identified in this way can be assessed for their ability to accumulate in vivo in a specific tissue or organ, such as skin, adipose tissue, or lymph node, by intravenous injection of the adptide conjugated to an imaging agent or moiety, such as an immunoflorescent reagent.

The disclosure contemplates the use of the phage display selection to screen for aptides that will bind to a protein (e.g., (1) an endothelial cell surface marker, e.g., Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Tttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a; (2) a venule endothelial cell surface marker, e.g., Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1; (3) a non-venule endothelial cell surface marker, e.g., Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Ja5, Laptm5, Aqp7, Gja4, Mlec, P2ry2, Cd97, Unc5b, Lpar6, Sema6d, Ppap2b, Lpar4, Ly86, H2-Aa, and Cd74; and/or Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a; (4) a skin microvessel endothelial cell surface marker e.g., Nrp2, Gpr1, C630004H02Rik, Fndc1, 2310046K01Rik, Insr, Slco2a1, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Nrp2, Htr2b, Mr1, Lifr, Anxa1, Lphn2, Vamp5, Olr1, Eps8, Slco2b1, Slco2a1, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; an adipose tissue microvessel endothelial cell surface marker, e.g., Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Adora2a, H2-Ab1, Hspg2, Gpr81, Kcna5, Jam3, and Gpc4; and/or Il1rl1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; and (6) a lymph node microvessel endothelial cell surface marker, e.g., Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik).

In some aspects, the disclosure provides an aptide that specifically binds to a protein (e.g., (1) an endothelial cell surface marker, e.g., Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a; (2) a venule endothelial cell surface marker, e.g., Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1; (3) a non-venule endothelial cell surface marker, e.g., Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74; and/or Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a; (4) a skin microvessel endothelial cell surface marker e.g., Nrp2, Gpr1, C630004H02Rik, Fndc1, 2310046K01Rik, Insr, Slco2a1, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Nrp2, Htr2b, Mr1, Lifr, Anxa1, Lphn2, Vamp5, Olr1, Eps8, Slco2b1, Slco2a1, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9; (5) an adipose tissue microvessel endothelial cell surface marker, e.g., Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Adora2a, H2-Ab1, Hspg2, Gpr81, Kcna5, Jam3, and Gpc4; and/or Il1rl1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3; and (6) a lymph node microvessel endothelial cell surface marker, e.g., Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik).

The disclosure also contemplates in vitro screening methods. Protein interactions may also be detected using, for example, gel electrophoresis where protein interactions can be detected by changes in electrophoretic mobility (detecting, for example, changes in size due to the binding of one or more proteins with another protein). Additionally, protein interactions can be detected by Western blotting. Western blotting detects proteins by transferring proteins from an electrophoresis gel to, e.g., nitrocellulose paper. Antibodies are then used to detect proteins that may have been transferred to the paper. Co-localization of two or more antibodies indicates possible protein-protein interaction.

Similarly, protein-protein interactions can be detected using affinity column chromatography. In this procedure, a binding agent (e.g., a target protein such as a microvessel endothelial cell targeting agent) is bound to the column media (usually, for example, sepharose beads treated to bind the selected target protein and then treated to block any unused binding sites). The test agent (e.g., a protein or a mixture of proteins) suspected of interacting with the selected target protein is then run over the column. Proteins capable of interacting with the selected protein will bind the target protein and non-interacting proteins will run through the column. Bound, interactive proteins can then be released by changing stringency conditions.

The screening methods contemplate employing combinatorial peptide and small molecule libraries. For example, another aspect of the disclosure relates to identifying agents which bind the surface markers identified herein by screening combinatorial polypeptide libraries which encode either a random or controlled collection of amino acids. One such method is identifying molecules which bind, for example, a microvessel endothelial cell surface marker described herein from a polypeptide array. An array of polypeptides is synthesized on a solid support (e.g., a biological chip) as described by Pirrung et al., U.S. Pat. No. 5,143,854, the contents of which are incorporated herein by reference. The polypeptides which are attached to the support are called probes. The resulting product is then processed to determine which polypeptides of the array bind a target protein (e.g., an endothelial cell surface marker described herein). The array linked support can be contacted with the target molecule under conditions appropriate for binding, and specific probe proteins which bind the target molecule are identified. Methods for detecting labeled markers on a support are provided by Trulson et al., U.S. Pat. No. 5,578,832, the contents of which are incorporated herein by reference.

Another method for identifying polypeptides from a library which bind to a specified molecule is provided by Dower et al., U.S. Pat. No. 5,432,018, the contents of which are incorporated herein by reference. In addition, libraries of non-polypeptide chemical agents can be screened for binding to and/or inhibition of an endothelial cell surface marker described herein by the method according to Zambias et al., U.S. Pat. No. 5,807,754, the contents of which are incorporated herein by reference, and also the method according to J. Ellman, U.S. Pat. No. 5,288,514, the contents of which are incorporated herein by reference.

In an aspect, disclosed herein is a method of identifying a candidate microvessel endothelial cell targeting agent which binds to a protein expressed on the surface of a microvessel endothelial cell. An exemplary method of identifying a candidate microvessel endothelial cell targeting agent which binds to a protein expressed on the surface of a microvessel endothelial cell comprises: (a) contacting a protein expressed on the surface of a microvessel endothelial cell with a test agent; and (b) assessing the ability of the test agent to bind the protein expressed on the surface of the microvessel endothelial cell, wherein a test agent that binds to the protein expressed on the surface of the microvessel endothelial cell is a candidate microvessel endothelial cell targeting agent.

In an aspect, disclosed herein is a method of identifying a candidate microvessel endothelial cell targeting agent which binds to a protein expressed on the surface of a microvessel endothelial cell and delivers an agent to a microvessel endothelial cell in a subject. An exemplary method of identifying a candidate microvessel endothelial cell targeting agent which binds to a protein expressed on the surface of a microvessel endothelial cell and delivers an agent to a microvessel endothelial cell in a subject comprises: (a) administering to a subject a test microvessel endothelial cell targeting agent which binds to a protein expressed on the surface of a microvessel endothelial cell coupled to an agent; and (b) assessing the ability of the microvessel endothelial cell targeting agent to deliver the agent to a microvessel endothelial cell in the subject, wherein a test agent that delivers the agent to a microvessel endothelial cell in the subject is a candidate microvessel endothelial cell targeting agent.

Generally, the protein expressed on the surface of the microvessel endothelial cell is encoded by a gene that is preferentially expressed in microvessels. Exemplary such genes include, but are not limited to, Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74. Exemplary such genes also include, but are not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some aspects, the disclosure provides methods of identifying venule endothelial cell targeting agents. In an aspect, disclosed herein is a method of identifying a candidate venule endothelial cell targeting agent which binds to a protein expressed on the surface of a venule endothelial cell. In some embodiments, a method of identifying a candidate venule endothelial cell targeting agent which binds to a protein expressed on the surface of a venule endothelial cell comprises: (a) contacting a protein expressed on the surface of a venule endothelial cell with a test agent; and (b) assessing the ability of the test agent to bind the protein expressed on the surface of the venule endothelial cell, wherein a test agent that binds to the protein expressed on the surface of the venule endothelial cell is a candidate venule endothelial cell targeting agent.

In an aspect, a method of identifying a candidate venule endothelial cell targeting agent which binds to a protein expressed on the surface of a venule endothelial cell and delivers an agent to a venule endothelial cell in a subject. An exemplary method of identifying a candidate venule endothelial cell targeting agent which binds to a protein expressed on the surface of a venule endothelial cell and delivers an agent to a venule endothelial cell in a subject comprises: (a) administering to a subject a test venule endothelial cell targeting agent which binds to a protein expressed on the surface of a venule endothelial cell coupled to an agent; and (b) assessing the ability of the test venule endothelial cell targeting agent to deliver the agent to a venule endothelial cell in the subject, wherein a test agent that delivers the agent to a venule endothelial cell in the subject is a candidate venule endothelial cell targeting agent.

Generally, the protein expressed on the surface of the venule endothelial cell is encoded by a gene exhibiting higher expression levels in venule endothelial cells compared to non-venule endothelial cells. Examples of such genes include, but are not limited to, Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. Examples of such genes also include, but are not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In an aspect, disclosed herein is a method of identifying a candidate non-venule endothelial cell targeting agent which binds to a protein expressed on the surface of a non-venule endothelial cell. An exemplary method of identifying a candidate non-venule endothelial cell targeting agent which binds to a protein expressed on the surface of a non-venule endothelial cell comprises: (a) contacting a protein expressed on the surface of a non-venule endothelial cell with a test agent; and (b) assessing the ability of the test agent to bind the protein expressed on the surface of the non-venule endothelial cell, wherein a test agent that binds to the protein expressed on the surface of the non-venule endothelial cell is a candidate non-venule endothelial cell targeting agent.

In an aspect, a method of identifying a candidate microvessel endothelial cell targeting agent which binds to a protein expressed on the surface of a non-venule endothelial cell and delivers an agent to a non-venule endothelial cell in a subject. An exemplary method of identifying a candidate microvessel endothelial cell targeting agent which binds to a protein expressed on the surface of a non-venule endothelial cell and delivers an agent to a non-venule endothelial cell in a subject comprises: (a) administering to a subject a test non-venule endothelial cell targeting agent which binds to a protein expressed on the surface of a non-venule endothelial cell coupled to an agent; and (b) assessing the ability of the non-venule endothelial cell targeting agent to deliver the agent to a non-venule endothelial cell in the subject, wherein a test agent that delivers the agent to a non-venule endothelial cell in the subject is a candidate microvessel endothelial cell targeting agent. Generally, the protein expressed on the surface of the non-venule endothelial cell is encoded by a gene exhibiting higher expression levels in non-venule endothelial cells compared to venule endothelial cells. Examples of such genes include, but are not limited to, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. Examples of such genes also include, but are not limited to, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a. In some aspects, the disclosure provides methods of identifying candidate skin microvessel endothelial cell targeting agents. In an aspect, the disclosure provides a method of identifying a candidate skin microvessel endothelial cell targeting agent which binds to a protein expressed on the surface of a skin microvessel endothelial cell. An exemplary method of identifying a candidate skin microvessel endothelial cell targeting agent which binds to a protein expressed on the surface of a skin microvessel endothelial cell comprises: (a) contacting a protein expressed on the surface of a skin microvessel endothelial cell with a test agent; and (b) assessing the ability of the test agent to bind the protein expressed on the surface of the skin microvessel endothelial cell, wherein a test agent that binds to the protein expressed on the surface of the skin microvessel endothelial cell is a candidate skin microvessel endothelial cell targeting agent.

In an aspect, the disclosure provides a method of identifying a candidate skin microvessel endothelial cell targeting agent which binds to a protein expressed on the surface of a skin microvessel endothelial cell and delivers an agent to a skin microvessel endothelial cell in a subject. An exemplary method of identifying a candidate skin microvessel endothelial cell targeting agent which binds to a protein expressed on the surface of a skin microvessel endothelial cell and delivers an agent to a skin microvessel endothelial cell in a subject comprises: (a) administering to a subject a test skin microvessel endothelial cell targeting agent which binds to a protein expressed on the surface of a skin microvessel endothelial cell coupled to an agent; and (b) assessing the ability of the test skin microvessel endothelial cell targeting agent to deliver the agent to a skin microvessel endothelial cell in the subject, wherein a test skin microvessel endothelial cell targeting agent that delivers the agent to a skin microvessel endothelial cell in the subject is a candidate skin microvessel endothelial cell targeting agent.

In some embodiments, the protein expressed on the surface of the skin microvessel endothelial cell is encoded by a gene exhibiting higher expression levels in skin venule endothelial cells compared to skin non-venule endothelial cells. Examples of such genes include, but are not limited to, Nrp2, Gpr1, C630004H02Rik, Fndc1, 2310046K01Rik, Insr, and Slco2a1. Examples of such genes also include, but are not limited to, Nrp2, Htr2b, Mr1, Lifr, Anxa1, Lphn2, Vamp5, Olr1, Eps8, Slco2b1, and Slco2a1.

In some embodiments, the protein expressed on the surface of the skin microvessel endothelial cell is encoded by a gene exhibiting higher expression levels in skin non-venule endothelial cells compared to skin venule endothelial cells. Examples of such genes include, but are not limited to, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. Examples of such genes also include, but are not limited to, Gm7609, Tns1, Ptprc, Rgs1, Fcer1g, Itgb2, Slc41a2, Cd68, Cd300c, Cd7, Cd180, Gpr183, Ptp4a3, Nckap11, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

In some aspects, the disclosure provides methods of identifying candidate adipose tissue microvessel endothelial cell targeting agents. In an aspect, disclosed herein is a method of identifying a candidate adipose tissue microvessel endothelial cell targeting agent which binds to a protein expressed on the surface of an adipose tissue microvessel endothelial cell. An exemplary method of identifying a candidate adipose tissue microvessel endothelial cell targeting agent which binds to a protein expressed on the surface of an adipose tissue microvessel endothelial cell comprises: (a) contacting a protein expressed on the surface of an adipose tissue microvessel endothelial cell with a test agent; and (b) assessing the ability of the test agent to bind the protein expressed on the surface of the adipose tissue microvessel endothelial cell, wherein a test agent that binds to the protein expressed on the surface of the adipose tissue microvessel endothelial cell is a candidate adipose tissue microvessel endothelial cell targeting agent.

In an aspect, the disclosure provides a method of identifying a candidate adipose tissue microvessel endothelial cell targeting agent which binds to a protein expressed on the surface of an adipose tissue microvessel endothelial cell and delivers an agent to an adipose tissue microvessel endothelial cell in a subject. An exemplary method of identifying a candidate adipose tissue microvessel endothelial cell targeting agent which binds to a protein expressed on the surface of an adipose tissue microvessel endothelial cell and delivers an agent to an adipose tissue microvessel endothelial cell in a subject comprises: (a) administering to a subject a test adipose tissue microvessel endothelial cell targeting agent which binds to a protein expressed on the surface of an adipose tissue microvessel endothelial cell coupled to an agent; and (b) assessing the ability of the test adipose tissue microvessel endothelial cell targeting agent to deliver the agent to an adipose tissue microvessel endothelial cell in the subject, wherein a test adipose tissue microvessel endothelial cell targeting agent that delivers the agent to an adipose tissue microvessel endothelial cell in the subject is a candidate adipose tissue microvessel endothelial cell targeting agent.

In some embodiments, the protein expressed on the surface of the adipose tissue microvessel endothelial cell is encoded by a gene exhibiting higher expression levels in adipose tissue venule endothelial cells compared to adipose tissue non-venule endothelial cells. Exemplary such genes include, but are not limited to, Il1rl1, Gm7609, Rgs1, Gpr126, P2rx1, Slc6a4, Itgb4, A530099J19Rik, Fcer1g, Fcer1a, Slc7a8, Nckap11, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. Exemplary such genes also include, but are not limited to, Il1rl1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the protein expressed on the surface of the adipose tissue microvessel endothelial cell is encoded by a gene exhibiting higher expression levels in adipose tissue non-venule endothelial cells compared to adipose tissue venule endothelial cells. Exemplary such genes include, but are not limited to, Adora2a, H2-Ab1, Hspg2, Gpr81, Kcna5, Jam3, and Gpc4. Exemplary such genes include, but are not limited to, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some aspects, the disclosure provides methods of identifying candidate lymph node microvessel endothelial cell targeting agents. In an aspect, the disclosure provides a method of identifying a candidate lymph node microvessel endothelial cell targeting agent which binds to a protein expressed on the surface of a lymph node microvessel endothelial cell. An exemplary method of identifying a candidate lymph node microvessel endothelial cell targeting agent which binds to a protein expressed on the surface of a lymph node microvessel endothelial cell comprises: (a) contacting a protein expressed on the surface of a lymph node microvessel endothelial cell with a test agent; and (b) assessing the ability of the test agent to bind the protein expressed on the surface of the lymph node microvessel endothelial cell, wherein a test agent that binds to the protein expressed on the surface of the lymph node microvessel endothelial cell is a candidate lymph node microvessel endothelial cell targeting agent.

In an aspect, the disclosure provides a method of identifying a candidate lymph node microvessel endothelial cell targeting agent which binds to a protein expressed on the surface of a lymph node microvessel endothelial cell and delivers an agent to a lymph node microvessel endothelial cell in a subject. An exemplary method of identifying a candidate lymph node microvessel endothelial cell targeting agent which binds to a protein expressed on the surface of a lymph node microvessel endothelial cell and delivers an agent to a lymph node microvessel endothelial cell in a subject comprises: (a) administering to a subject a test lymph node microvessel endothelial cell targeting agent which binds to a protein expressed on the surface of a lymph node microvessel endothelial cell coupled to an agent; and (b) assessing the ability of the test lymph node microvessel endothelial cell targeting agent to deliver the agent to a lymph node microvessel endothelial cell in the subject, wherein a test lymph node microvessel endothelial cell targeting agent that delivers the agent to a lymph node microvessel endothelial cell in the subject is a candidate lymph node microvessel endothelial cell targeting agent.

In some embodiments, the protein expressed on the surface of the lymph node microvessel endothelial cell is encoded by a gene exhibiting higher expression levels in lymph node venule endothelial cells compared to lymph node non-venule endothelial cells. Exemplary such genes include, but are not limited to, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg.

In some embodiments, the protein expressed on the surface of the lymph node microvessel endothelial cell is encoded by a gene exhibiting higher expression levels in lymph node non-venule endothelial cells compared to lymph node venule endothelial cells. Exemplary such genes include, but are not limited to, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. Exemplary such genes also include, but are not limited to, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

The disclosure contemplates assessing various test targeting agents, including, for example test microvessel endothelial cell targeting agents, test venule endothelial cell targeting agents, test non-venule endothelial cell targeting agents, test skin microvessel endothelial cell targeting agents (e.g., a skin venule endothelial cell targeting agent and a skin non-venule endothelial cell targeting agent), test adipose tissue microvessel endothelial cell targeting agents (e.g., an adipose tissue venule endothelial cell targeting agent and an adipose tissue non-venule endothelial cell targeting agent), and test lymph node endothelial cell targeting agents (e.g., a lymph node venule endothelial cell targeting agent and a lymph node non-venule endothelial cell targeting agent).

Exemplary types of agents suitable for use as such test targeting agents (e.g., test microvessel endothelial cell targeting agents, test venule endothelial cell targeting agents, test non-venule endothelial cell targeting agents, test skin microvessel endothelial cell targeting agents, test adipose endothelial cell targeting agents, test lymph node endothelial cell targeting agents) include, but are not limited to, small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, an exemplary agent for use as a test targeting agent comprises an aptide.

The disclosure contemplates administering a test agent (e.g., test microvessel endothelial cell targeting agents, test venule endothelial cell targeting agents, test non-venule endothelial cell targeting agents, test skin microvessel endothelial cell targeting agents, test adipose endothelial cell targeting agents, test lymph node endothelial cell targeting agents) to a subject in any suitable manner. In some embodiments, administration comprises intravenous infusion.

The disclosure contemplates various methods of assessing the ability of the test agent (e.g., test microvessel endothelial cell targeting agents, test venule endothelial cell targeting agents, test non-venule endothelial cell targeting agents, test skin microvessel endothelial cell targeting agents, test adipose endothelial cell targeting agents, test lymph node endothelial cell targeting agents) and/or agent to be internalized into or transported across the microvessel endothelial cell expressing the endothelial cell surface marker (e.g., microvessel endothelial cell surface marker, venule endothelial cell surface marker, non-venule endothelial cell surface marker, skin endothelial cell surface marker, adipose tissue endothelial cell surface marker, and lymph node endothelial cell surface marker), and/or to accumulate in a microvessel, tissue or organ surrounding the endothelial cell expressing that marker. For example, the test agent and/or agent can include a detectable component. In some embodiments, the test agent comprises a fluorescent component. In some embodiments, the agent comprises a fluorescent component. In some embodiments, the agent is a fluorescent reagent. In some embodiments, assessing the ability of the test targeting agent to deliver the agent to a microvessel endothelial cell comprises in situ imaging of the test agent or the agent (e.g., Multi-photon intravital microscopy). In some embodiments, assessing the ability of the test targeting agent to deliver the agent to a microvessel endothelial cell comprises analyzing internalization of the test agent or the agent in a microvessel, tissue, or organ surrounding the microvessel endothelial cell. In some embodiments, assessing the ability of the test targeting agent to deliver the agent to a microvessel endothelial cell comprises analyzing accumulation of the test targeting agent or the agent in a microvessel, tissue, or organ surrounding the microvessel endothelial cell.

In some embodiments the methods further comprise assessing the ability of the agent to exhibit a therapeutic, diagnostic, or imaging effect.

In some embodiments, the methods further comprise coupling the candidate agent to an endothelial cell targeting agent described that binds to a protein expressed on the surface of a microvessel endothelial cell, and assessing the ability of the microvessel endothelial cell targeting agent to target the candidate agent to a targeted tissue comprising the endothelial cell. Exemplary endothelial cell targeting agents include: (1) microvessel endothelial cell targeting agents that bind to a protein expressed on the surface of microvessel endothelial cells (e.g., a protein encoded by a gene selected from the group consisting of Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a); (2) a venule endothelial cell targeting agent that binds to a protein expressed on the surface of venule endothelial cells (e.g., a protein encoded by a gene selected from the group consisting of Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1; and/or Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1); (3) a non-venule endothelial cell targeting agent that binds to a protein expressed on the surface of non-venule endothelial cells (e.g., a protein encoded by a gene selected from the group consisting of Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74; and/or Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a); (4) a skin microvessel endothelial cell targeting agent that binds to a protein expressed on the surface of skin microvessel endothelial cells (e.g., a protein encoded by a gene selected from the group consisting of Nrp2, Gpr1, C630004H02Rik, Fndc1, 2310046K01Rik, Insr, Slco2a1, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9; and/or Nrp2, Htr2b, Mr1, Lifr, Anxa1, Lphn2, Vamp5, Olr1, Eps8, Slco2b1, Slco2a1, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9); (5) adipose tissue microvessel endothelial cell targeting agent that binds to a protein expressed on the surface of adipose tissue microvessel endothelial cells (e.g., a protein encoded by a gene selected from the group consisting of Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Adora2a, H2-Ab1, Hspg2, Gpr81, Kcna5, Jam3, and Gpc4; and/or Il1rl1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3); and (6) a lymph node microvessel endothelial cell targeting agent that binds to a protein expressed on the surface of lymph node venule endothelial cells (e.g., a protein encoded by a gene selected from the group consisting of Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5; and/or Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik).

Generally, the endothelial cell targeting agents can be assessed for their ability to target the candidate agent to the desired location (e.g., the skin microvessel endothelial cell targeting agent is assessed for its ability to target the candidate agent to the skin; the adipose tissue microvessel endothelial cell targeting agent is assessed for its ability to target the candidate agent to adipose tissue; the lymph node microvessel endothelial cell targeting agent is assessed for its ability to target the candidate agent to lymph nodes). The disclosure contemplates any suitable protocol for assessing the ability of the endothelial cell targeting agents to target a candidate agent to a desired location. For example, fluorescent immunoreagents or nanoparticles conjugated to MAbs or other ligands specific for these candidate targets can be used to analyze the accumulation of targeted reagents (relative to appropriate controls) in tissues after intravenous infusion. Molecular targets in which cross-linking leads to internalization are likely to be effective endothelial cell targeting agents. Multi-photon intravital microscopy technology can be used to make such determinations by direct in situ imaging.

Methods of Treatment

The disclosure contemplates various methods of treatment involving administering agents described herein (e.g., an agent coupled to a targeting agent selected from a microvessel endothelial cell targeting agent, a venule endothelial cell targeting agent, a non-venule endothelial cell targeting agent, a skin microvessel endothelial cell targeting agent, an adipose tissue microvessel endothelial cell targeting agent, a lymph node microvessel endothelial cell targeting agent) to a subject.

By "treatment, prevention or amelioration of a disease" (e.g., an inflammatory disease, disease characterized by visceral fat inflammation, disease characterized by lymphadenitis, etc.) is meant delaying or preventing the onset of such a disorder (e.g. chronic inflammation), at reversing, alleviating, ameliorating, inhibiting, slowing down or stopping the progression, aggravation or deterioration the progression or severity of such a condition. In one embodiment, the symptom of a disease involving leukocyte trafficking is alleviated by at least 20%, at least 30%, at least 40%, or at least 50%. In one embodiment, the symptom of a disease involving leukocyte trafficking is alleviated by more that 50%. In one embodiment, the symptom of a disease involving leukocyte trafficking is alleviated by 80%, 90%, or greater. Treatment also includes improvements in immune function. In some embodiments, immune function improves by at least about 10%, 20%, 30%, 40%, 50% or more.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. In some embodiments of the invention, the subject suffers from a microvessel endothelial cell-associated disorder (e.g., a microvessel endothelial cell-associated disorder, a venule endothelial cell-associated disorder, a non-venule endothelial cell-associated disorder, a skin microvessel endothelial cell-associated disorder, an adipose tissue endothelial cell-associated disorder, or a lymph node microvessel endothelial cell-associated disorder).

In some aspects, the disclosure contemplates methods of treating microvessel endothelial cell-associated disorders. As used herein, "microvessel endothelial cell-associated disorders" refers to any disease, disorder, or condition involving, originating in, relating to, or otherwise affecting microvessel endothelial cells or a microvessel, tissue, or organ in which the microvessel endothelial cell resides, including venular disorders and non-venular disorders. In an aspect, the disclosure provides a method of treating a microvessel endothelial cell-associated disorder in a subject in need thereof, comprising administering to the subject an effective amount of a therapeutic agent for treating the microvessel endothelial cell-associated disorder coupled to a microvessel endothelial cell targeting agent which binds to a protein expressed on the surface of a microvessel endothelial cell.

In some embodiments, the protein expressed on the surface of the microvessel endothelial cell is encoded by a gene that is preferentially expressed in microvessels. Examples of such genes include, but are not limited to, Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74. Examples of such genes also include, but are not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

Generally, the microvessel endothelial cell targeting agent delivers an agent to a microvessel endothelial cell. The treatment methods contemplate coupling therapeutic agents, diagnostic agents, and imaging agents to a microvessel endothelial cell targeting agent for delivery to a microvessel endothelial cell for treating microvessel endothelial cell-associated disorders.

In some embodiments, the microvessel endothelial cell targeting agent delivers the coupled therapeutic agent to microvessel endothelial cells. In such embodiments, delivery of the therapeutic agent to the microvessel endothelial cell induces a local therapeutic effect in the microvessel endothelial cell, or a microvessel, tissue or organ surrounding the microvessel endothelial cell. In such embodiments, delivery of the therapeutic agent to the microvessel endothelial cell minimizes or eliminates an effect in the subject (e.g., a systemic effect, a toxic effect, an adverse effect, a side effect, or an undesired effect). In such embodiments, delivery of the agent to the microvessel endothelial cells can be used to treat or prevent a microvessel endothelial cell-associated disorder. The disclosure contemplates treating or preventing any microvessel endothelial cell-associated disorder in a subject in which targeted delivery of the agent to the microvessel would be desirable.

In some embodiments, the microvessel endothelial cell-associated disorder is an inflammatory disease. In some embodiments, the microvessel endothelial cell-associated disorder is a microvasculature disease (e.g., venular disorder or non-venular disorder).

Those skilled in the art will appreciate that the therapeutic agent to be delivered depends upon the particular microvessel endothelial cell-associated disorder to be treated (e.g., anti-inflammatory agents for treating inflammatory diseases).

In some embodiments, the method further comprises selecting a subject who would likely benefit from delivery of therapeutic agent to the subject's microvessels. Subjects who would likely benefit from delivery of the therapeutic agent to the subject's microvessel endothelial cells include subjects diagnosed with one or more of, having a family history of one or more of, or presenting with one or more symptoms of, the microvessel endothelial cell-associated disorders described herein.

In some embodiments, the method further comprises modifying a dose of the therapeutic agent for local delivery to the microvessel endothelial cell.

In some embodiments, the microvessel endothelial cell targeting agent delivers the coupled diagnostic agent to microvessel endothelial cells. In such embodiments, delivery of the agent to the microvessel endothelial cells can be used to diagnose a microvessel endothelial cell-associated disorder in a subject.

In some embodiments, the microvessel endothelial cell targeting agent delivers the coupled imaging agent to microvessel endothelial cells. In such embodiments, delivery of the agent to the microvessel endothelial cells can be used to image a microvessel endothelial cell-associated disorder in a subject.

It should be appreciated that one or more therapeutic agents, diagnostic agents, and/or imaging agents can be coupled to one or more microvessel endothelial cell targeting agents, and formulated as a composition for administration to the subject.

In some aspects, the disclosure contemplates methods of treating venule endothelial cell-associated disorders. As used herein, "venule endothelial cell-associated disorders" refers to any disease, disorder, or condition involving, originating in, relating to, or otherwise affecting venule endothelial cells, or a venule, tissue, or organ in which the venule endothelial cell resides. In an aspect, the disclosure provides a method of treating a venule endothelial cell-associated disorder in a subject in need thereof, comprising administering to the subject an effective amount of a therapeutic agent for treating the venule endothelial cell-associated disorder coupled to a venule endothelial cell targeting agent which binds to a protein expressed on the surface of a venule endothelial cell.

In some embodiments, the protein expressed on the surface of the venule endothelial cell is encoded by a gene that is preferentially expressed in venule endothelial cells. Examples of such genes include, but are not limited to, Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. Examples of such genes also include, but are not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

Generally, the venule endothelial cell targeting agent delivers an agent to a venule endothelial cell. The treatment methods contemplate coupling therapeutic agents, diagnostic agents, and imaging agents to a venule endothelial cell targeting agent for delivery to a venule endothelial cell for treating venule endothelial cell-associated disorders.

In some embodiments, the venule endothelial cell targeting agent delivers the coupled therapeutic agent to venule endothelial cells. In such embodiments, delivery of the therapeutic agent to the venule endothelial cell induces a local therapeutic effect in the venule endothelial cell, or a venule, tissue or organ surrounding the venule endothelial cell. In such embodiments, delivery of the therapeutic agent to the venule endothelial cell minimizes or eliminates an effect in the subject (e.g., a systemic effect, a toxic effect, an adverse effect, a side effect, and an undesired effect). In such embodiments, delivery of the agent to the venule endothelial cells can be used to treat or prevent a venule endothelial cell-associated disorder. The disclosure contemplates treating or preventing any venule endothelial cell-associated disorder in a subject in which targeted delivery of the agent to the venules would be desirable. In some embodiments, the venule endothelial cell-associated disorder is an inflammatory disease. In some embodiments, the venule endothelial-associated disorder is a venular disorder.

Those skilled in the art will appreciate that the appropriate therapeutic agent to select for any particular treatment will depend upon the particular venule endothelial cell-associated disorder to be treated.

In some embodiments, the method further comprises selecting a subject who would likely benefit from delivery of the therapeutic agent to the subject's venule endothelial cells. Subjects who would likely benefit from delivery of the therapeutic agent to the subject's venule endothelial cells include subjects diagnosed with one or more of, having a family history of one or more of, or presenting with one or more symptoms of, the venule endothelial cell-associated disorders described herein.

In some embodiments, the method further comprises modifying a dose of the therapeutic agent for local delivery to the venule endothelial cell.

In some embodiments, the venule endothelial cell targeting agent delivers the coupled diagnostic agent to venule endothelial cells in the subject. In such embodiments, delivery of the agent to the venule endothelial cells can be used to diagnose a venule endothelial cell-associated disorder in a subject.

In some embodiments, the venule endothelial cell targeting agent delivers the coupled imaging agent to venule endothelial cells in the subject. In such embodiments, delivery of the agent to the venule endothelial cells can be used to image a venule endothelial cell-associated disorder in a subject.

In some aspects, the disclosure contemplates methods of treating non-venule endothelial cell-associated disorders. As used herein, "non-venule endothelial cell-associated disorders" refers to any disease, disorder, or condition involving, originating in, relating to, or otherwise affecting non-venule endothelial cells, or a non-venule, tissue, or organ in which the non-venule endothelial cell resides. In an aspect, disclosed herein is a method of treating a non-venule endothelial cell-associated disorder in a subject in need thereof, comprising administering to the subject an effective amount of a therapeutic agent for treating the non-venule endothelial cell-associated disorder coupled to a non-venule endothelial cell targeting agent which binds to a protein expressed on the surface of a non-venule endothelial cell.

In some embodiments, the protein expressed on the surface of the non-venule endothelial cell is encoded by a gene that is preferentially expressed in non-venule endothelial cells. Examples of such genes include, but are not limited to, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. Examples of such genes also include, but are not limited to, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

Generally, the non-venule endothelial cell targeting agent delivers an agent to a non-venule endothelial cell. The treatment methods contemplate coupling therapeutic agents, diagnostic agents, and imaging agents to a non-venule endothelial cell targeting agent for delivery to a non-venule endothelial cell for treating non-venule endothelial cell-associated disorders.

In some embodiments, the non-venule endothelial cell targeting agent delivers the coupled therapeutic agent to non-venule endothelial cells. In such embodiments, delivery of the therapeutic agent to the non-venule endothelial cell induces a local therapeutic effect in the non-venule endothelial cell, or a non-venule, tissue or organ surrounding the non-venule endothelial cell. In such embodiments, delivery of the therapeutic agent to the non-venule endothelial cell minimizes or eliminates an effect in the subject selected from the group consisting of a systemic effect, a toxic effect, an adverse effect, a side effect, and an undesired effect. In such embodiments, delivery of the agent to the non-venule endothelial cells can be used to treat or prevent a non-venule endothelial cell-associated disorder. The disclosure contemplates treating or preventing any non-venule endothelial cell-associated disorder in a subject in which targeted delivery of the agent to the non-venule would be desirable. In some embodiments, the non-venule endothelial cell-associated disorder is a non-venular disorder. In some embodiments, the non-venule endothelial cell-associated disorder is an inflammatory disease.

Those skilled in the art will appreciate that the appropriate therapeutic agent to use will depend upon the particular non-venule endothelial cell-associated disorder to be treated.

In some embodiments, the methods further comprise selecting a subject who would likely benefit from delivery of the therapeutic agent to the subject's non-venule endothelial cells. Subjects who would likely benefit from delivery of the therapeutic agent to the subject's non-venule endothelial cells include subjects diagnosed with one or more of, having a family history of one or more of, or presenting with one or more symptoms of, the non-venule endothelial cell-associated disorders described herein.

In some embodiments, the methods further comprise modifying a dose of the therapeutic agent for local delivery to the non-venule endothelial cell.

In some embodiments, the non-venule endothelial cell targeting agent delivers the coupled diagnostic agent to non-venule endothelial cells in the subject. In such embodiments, delivery of the agent to the non-venule endothelial cells can be used to diagnose a non-venule endothelial cell-associated disorder in a subject.

In some embodiments, the non-venule endothelial cell targeting agent delivers the coupled imaging agent to non-venule endothelial cells in the subject. In such embodiments, delivery of the agent to the non-venule endothelial cells can be used to image a non-venule endothelial cell-associated disorder in a subject.

In some aspects, the disclosure provides methods of treating skin microvessel endothelial cell-associated disorders in a subject in need thereof. As used herein, "skin microvessel endothelial cell-associated disorders" refers to any disease, disorder, or condition involving, originating in, relating to, or otherwise affecting skin microvessel endothelial cells, or a microvessel, tissue, or organ in which the skin microvessel endothelial cell resides. In an aspect, disclosed herein is a method of treating a skin microvessel endothelial cell-associated disorder in a subject in need thereof, comprising administering to the subject an effective amount of a therapeutic agent for treating the skin microvessel endothelial cell-associated disorder coupled to a skin microvessel endothelial cell targeting agent which binds to a protein expressed on the surface of a skin microvessel endothelial cell.

In some embodiments, the protein expressed on the surface of the skin microvessel endothelial cell is encoded by a gene exhibiting higher expression levels in skin venule endothelial cells compared to skin non-venule endothelial cells. Examples of such genes include, but are not limited to Nrp2, Gpr1, C630004H02Rik, Fndc1, 2310046K01Rik, Insr, and Slco2a1. Examples of such genes also include, but are not limited to Nrp2, Htr2b, Mr1, Lifr, Anxa1, Lphn2, Vamp5, Olr1, Eps8, Slco2b1, and Slco2a1.

In some embodiments, the protein expressed on the surface of the skin microvessel endothelial cell is encoded by a gene exhibiting higher expression levels in skin non-venule endothelial cells compared to skin venule endothelial cells. Examples of such genes include, but are not limited to, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. Examples of such genes also include, but are not limited to, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

Generally, the skin microvessel endothelial cell targeting agent delivers an agent to a skin microvessel endothelial cell. The treatment methods contemplate coupling therapeutic agents, diagnostic agents, and imaging agents to a skin microvessel endothelial cell targeting agent for delivery to a skin microvessel endothelial cell for treating skin microvessel endothelial cell-associated disorders.

In some embodiments, the skin microvessel endothelial cell targeting agent delivers the coupled therapeutic agent to skin microvessel endothelial cells. Delivery of the therapeutic agent to the skin microvessel endothelial cell induces a local therapeutic effect in the skin microvessel endothelial cell, or a microvessel, tissue or organ surrounding the skin microvessel endothelial cell. Delivery of the therapeutic agent to the skin microvessel endothelial cell minimizes or eliminates an effect in the subject (e.g., a systemic effect, a toxic effect, an adverse effect, a side effect, and an undesired effect). In such embodiments, delivery of the agent to the skin microvessel endothelial cells can be used to treat or prevent a skin microvessel endothelial cell-associated disorder in a subject. The disclosure contemplates treating or preventing any skin microvessel endothelial cell-associated disorder in a subject in which targeted delivery of the agent to the skin would be desirable. In some embodiments, the skin microvessel endothelial cell-associated disorder is a skin inflammatory disease. In some embodiments, the skin microvessel endothelial cell-associated disorder is a skin disease.

Those skilled in the art will appreciate that the appropriate therapeutic agent to be used depends on the particular skin microvessel endothelial cell-associated disorder to be treated.

In some embodiments, the methods further comprise selecting a subject who would likely benefit from delivery of the therapeutic agent to the subject's skin microvessel endothelial cells. Subjects who would likely benefit from delivery of the therapeutic agent to the subject's skin microvessel endothelial cells include subjects diagnosed with one or more of, having a family history of one or more of, or presenting with one or more symptoms of, the skin microvessel endothelial cell-associated disorders described herein.

In some embodiments, the methods further comprise modifying a dose of the therapeutic agent for local delivery to the skin microvessel endothelial cell.

In some embodiments, the skin microvessel endothelial cell targeting agent delivers the coupled diagnostic agent to skin microvessel endothelial cells. In such embodiments, delivery of the agent to the skin microvessel endothelial cells can be used to diagnose a skin microvessel endothelial cell-associated disorder in a subject.

In some embodiments, the skin microvessel endothelial cell targeting agent delivers the coupled imaging agent to skin microvessel endothelial cells. In such embodiments, delivery of the agent to the skin microvessel endothelial cells can be used to image a skin microvessel endothelial cell-associated disorder in a subject.

It should be appreciated that one or more therapeutic agents, diagnostic agents, and/or imaging agents can be coupled to one or more skin microvessel endothelial cell targeting agents, and formulated as a composition for administration to the subject.

In some aspects, the disclosure provides methods of treating adipose tissue microvessel endothelial cell-associated disorders in a subject in need thereof. As used herein, "adipose tissue microvessel endothelial cell-associated disorders" refers to any disease, disorder, or condition involving, originating in, relating to, or otherwise affecting adipose tissue microvessel endothelial cells, or a microvessel, tissue, or organ in which the adipose tissue microvessel endothelial cell resides. In an aspect, disclosed herein is a method of treating an adipose tissue microvessel endothelial cell-associated disorder in a subject in need thereof, comprising administering to the subject an effective amount of a therapeutic agent for treating the adipose tissue microvessel endothelial cell-associated disorder coupled to an adipose tissue microvessel endothelial cell targeting agent which binds to a protein expressed on the surface of an adipose tissue microvessel endothelial cell.

In some embodiments, the protein expressed on the surface of the adipose tissue microvessel endothelial cell is encoded by a gene exhibiting higher expression levels in adipose tissue venule endothelial cells compared to adipose tissue non-venule endothelial cells. Examples of such genes include, but are not limited to, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. Examples of such genes also include, but are not limited to, Il1rl1, Tnfrsf1a, Mpz, Dnm3os, Icos1, Osbpl8, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the protein expressed on the surface of the adipose tissue microvessel endothelial cell is encoded by a gene exhibiting higher expression levels in adipose tissue non-venule endothelial cells compared to adipose tissue venule endothelial cells. Exemplary such genes include, but are not limited to, Adora2a, H2-Ab1, Hspg2, Gpr81, Kcna5, Jam3, and Gpc4. Exemplary such genes also include, but are not limited to, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

Generally, the adipose tissue microvessel endothelial cell targeting agent delivers an agent to an adipose tissue microvessel endothelial cell. The treatment methods contemplate coupling therapeutic agents, diagnostic agents, and imaging agents to an adipose tissue microvessel endothelial cell targeting agent for delivery to an adipose tissue microvessel endothelial cell for treating adipose tissue microvessel endothelial cell-associated disorders.

In some embodiments, the adipose tissue microvessel endothelial cell targeting agent delivers the coupled therapeutic agent to adipose tissue microvessel endothelial cells. In such embodiments, delivery of the therapeutic agent to the adipose tissue microvessel endothelial cell induces a local therapeutic effect in the adipose tissue microvessel endothelial cell, or a microvessel, tissue or organ surrounding the adipose tissue microvessel endothelial cell. In such embodiments, delivery of the therapeutic agent to the adipose tissue microvessel endothelial cell minimizes or eliminates an effect in the subject (e.g., a systemic effect, a toxic effect, an adverse effect, a side effect, and an undesired effect). In such embodiments, delivery of the agent to the adipose tissue microvessel endothelial cells can be used to treat or prevent an adipose tissue microvessel endothelial cell-associated disorder. In some embodiments, the adipose tissue microvessel endothelial cell-associated disorder is a disease characterized by visceral fat inflammation. In some embodiments, the adipose tissue microvessel endothelial cell-associated disorder is obesity or a related disorder.

Those skilled in the art will appreciate that the appropriate therapeutic agent to select will depend upon the particular an adipose tissue microvessel endothelial cell-associated disorder to be treated.

In some embodiments, the methods further comprise selecting a subject who would likely benefit from delivery of the therapeutic agent to the subject's adipose tissue microvessel endothelial cells. Subjects who would likely benefit from delivery of the therapeutic agent to the subject's adipose tissue microvessel endothelial cells include subjects diagnosed with one or more of, having a family history of one or more of, or presenting with one or more symptoms of, the adipose tissue disorders described herein.

In some embodiments, the methods further comprise modifying a dose of the therapeutic agent for local delivery to the adipose tissue microvessel endothelial cell.

In some embodiments, the adipose tissue microvessel endothelial cell targeting agent delivers the coupled diagnostic agent to adipose tissue microvessel endothelial cells in a subject. In such embodiments, delivery of the agent to the adipose tissue microvessel endothelial cells can be used to diagnose an adipose tissue microvessel endothelial cell-associated disorder in a subject.

In some embodiments, the adipose tissue microvessel endothelial cell targeting agent delivers the coupled imaging agent to adipose tissue microvessel endothelial cells in a subject. In such embodiments, delivery of the agent to the skin microvessel endothelial cells can be used to image a skin microvessel endothelial cell-associated disorder in a subject.

It should be appreciated that one or more therapeutic agents, diagnostic agents, and/or imaging agents can be coupled to one or more adipose tissue microvessel endothelial cell targeting agents, and formulated as a composition for administration to the subject.

In some aspects, the disclosure provides methods of treating lymph node microvessel endothelial cell-associated disorders in a subject in need thereof. As used herein, "lymph node microvessel endothelial cell-associated disorders" refers to any disease, disorder, or condition involving, originating in, relating to, or otherwise affecting lymph node microvessel endothelial cells, or a microvessel, tissue, or organ in which the lymph node microvessel endothelial cell resides. In an aspect, the disclosure provides a method of treating a lymph node microvessel endothelial cell-associated disorder in a subject in need thereof, comprising administering to the subject an effective amount of a therapeutic agent for treating the lymph node microvessel endothelial cell-associated disorder coupled to a lymph node microvessel endothelial cell targeting agent which binds to a protein expressed on the surface of a lymph node microvessel endothelial cell.

In some embodiments, the protein expressed on the surface of the lymph node microvessel endothelial cell is encoded by a gene exhibiting higher expression levels in lymph node venule endothelial cells compared to lymph node non-venule endothelial cells. Examples of such genes include, but are not limited to, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg. Examples of such genes also include, but are not limited to, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, and Chic1.

In some embodiments, the protein expressed on the surface of the lymph node microvessel endothelial cell is encoded by a gene exhibiting higher expression levels in lymph node non-venule endothelial cells compared to lymph node venule endothelial cells. Examples of such genes include, but are not limited to, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. Examples of such genes also include, but are not limited to, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik Generally, the lymph node microvessel endothelial cell targeting agent delivers an agent to lymph node microvessel endothelial cells. The treatment methods contemplate coupling therapeutic agents, diagnostic agents, and imaging agents to a lymph node microvessel endothelial cell targeting agent for delivery to a lymph node microvessel endothelial cell for treating lymph node microvessel endothelial cell-associated disorders.

In some embodiments, the lymph node microvessel endothelial cell targeting agent delivers the coupled therapeutic agent to lymph node microvessel endothelial cells. In such embodiments, delivery of the therapeutic agent to the lymph node microvessel endothelial cell induces a local therapeutic effect in the lymph node microvessel endothelial cell, or a microvessel, tissue or organ surrounding the lymph node microvessel endothelial cell. In such embodiments, delivery of the therapeutic agent to the lymph node microvessel endothelial cell minimizes or eliminates an effect in the subject selected from the group consisting of a systemic effect, a toxic effect, an adverse effect, a side effect, and an undesired effect. In such embodiments, delivery of the agent to the lymph node microvessel endothelial cells can be used to treat or prevent lymph node microvessel endothelial cell-associated disorders. The disclosure contemplates treating or preventing any lymph node microvessel endothelial cell-associated disorder in which targeted delivery of the agent to the lymph nodes would be desirable. In some embodiments, the lymph node microvessel endothelial cell-associated disorder is a disease characterized by lymphadenitis.

Those skilled in the art will appreciate that the appropriate therapeutic agent to be selected depends on the particular lymph node microvessel endothelial cell-associated disorder to be treated.

In some embodiments, the method further comprises selecting a subject who would likely benefit from delivery of the therapeutic agent to the subject's lymph node microvessel endothelial cells. Subjects who would likely benefit from delivery of the therapeutic agent to the subject's lymph node microvessel endothelial cells include subjects diagnosed with one or more of, having a family history of one or more of, or presenting with one or more symptoms of, the lymph node microvessel endothelial cell-associated disorder described herein.

In some embodiments, the method further comprises modifying a dose of the therapeutic agent for local delivery to the lymph node microvessel endothelial cell.

In some embodiments, the lymph node microvessel endothelial cell targeting agent delivers the coupled diagnostic agent to lymph node microvessel endothelial cells in a subject. In such embodiments, delivery of the agent to the skin microvessel endothelial cells can be used to diagnose a skin microvessel endothelial cell-associated disorder in a subject.

In some embodiments, the lymph node microvessel endothelial cell targeting agent delivers the coupled imaging agent to lymph node microvessel endothelial cells in a subject. In such embodiments, delivery of the agent to the skin microvessel endothelial cells can be used to image a skin microvessel endothelial cell-associated disorder in a subject.

It should be appreciated that any of the agents administered or employed in connection with the methods described herein can be administered or employed as part of a composition (e.g., a pharmaceutical composition).

In some embodiments, the methods described herein further comprise selecting a subject diagnosed with a microvessel endothelial cell-associated disorder described herein (e.g., a disorder characterized by visceral fat inflammation). A subject suffering from a microvessel endothelial cell-associated disorder can be selected based on the symptoms presented, a genetic diagnostic test, or family history. For example a subject suffering from a disorder characterized by visceral fat inflammation (e.g., metabolic syndrome) may show symptoms of fasting hyperglycemia, high blood pressure, central obesity, decreased HDL cholesterol levels, elevated triglycerides.

In some embodiments, the methods described herein further comprise selecting a subject at risk of developing a microvessel endothelial cell-associated disorder described herein (e.g., a disorder characterized by visceral fat inflammation). A subject at risk of developing a d a microvessel endothelial cell-associated disorder described herein (e.g., a disorder characterized by visceral fat inflammation, e.g., metabolic syndrome) can be selected based on a genetic diagnostic test (e.g., for a polymorphism of HMGA1, see, e.g. Chiefari et al., A polymorphism of HMGA1 is associated with increased risk of metabolic syndrome and related components. *Scientific Reports.* 2013; 3:1491) or based on the symptoms presented.

In some embodiments, the methods described herein further comprise selecting a subject suspected of having a disorder described herein (e.g., a disorder characterized by visceral fat inflammation, e.g., metabolic syndrome). A subject suspected of having a metabolic syndrome can be selected based on a genetic diagnostic test (e.g., for a polymorphism of HMGA1), based on family history, or based on the symptoms presented or a combination thereof.

Compositions

The disclosure contemplates compositions comprising at least one agent described herein (e.g., a microvessel endothelial cell targeting agent, a venule endothelial cell targeting agent, a non-venule endothelial cell targeting agent, a skin microvessel endothelial cell targeting agent, an adipose tissue endothelial cell targeting agent, a lymph node endothelial cell targeting agent, or any one or combination thereof coupled to an agent selected from a therapeutic agent, a diagnostic agent, or an imaging agent, or any combination thereof). The compositions described herein can be employed in various methods of treatment, diagnosis, and imaging described herein, as will be appreciated by those skilled in the art.

In some aspects, a composition comprises an effective amount of a microvessel endothelial cell targeting agent described herein. The composition can be used for treating, diagnosing, and imaging applications involving microvessel endothelial cells, or microvessels, tissues or organs in which the microvessel endothelial cells reside. In an aspect, the disclosure provides a composition comprising a microvessel endothelial cell targeting agent which binds to a protein expressed on the surface of a microvessel endothelial cell. In some embodiments, the protein expressed on the surface of the microvessel endothelial cell is encoded by a gene that is preferentially expressed in microvessels. Exemplary such genes include, but are not limited to, Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, PITH, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74. Exemplary such genes also include, but are not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a. In some aspects, a composition comprises an effective amount of a venule endothelial cell targeting agent described herein. The composition can be used for treating, diagnosing, and imaging applications involving venule endothelial cells, or venules, tissues or organs in which the venule endothelial cells reside. In an aspect, the disclosure provides a composition comprising a venule endothelial cell targeting agent which binds to a protein expressed on the surface of a venule endothelial cell. In some embodiments, the protein expressed on the surface of the venule endothelial cell is encoded by a gene exhibiting higher expression levels in venule endothelial cells compared to non-venule endothelial cells. Examples of such genes include, but are not limited to Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. Examples of such genes also include, but are not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2/// Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

In some aspects, a composition comprises an effective amount of a non-venule endothelial cell targeting agent described herein. The composition can be used for treating, diagnosing, and imaging applications involving non-venule endothelial cells, or non-venules, tissues or organs in which the non-venule endothelial cells reside. In an aspect, disclosed herein is a composition comprising a non-venule endothelial cell targeting agent which binds to a protein expressed on the surface of a non-venule endothelial cell. In some embodiments, the protein expressed on the surface of the non-venule endothelial cell is encoded by a gene exhibiting higher expression levels in non-venule endothelial cells compared to venule endothelial cells. Examples of such genes include, but are not limited to, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. Examples of such genes also include, but are not limited to, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some aspects, a composition comprises an effective amount of a skin microvessel endothelial cell targeting agent described herein. The composition can be used for treating, diagnosing, and imaging applications involving skin microvessel endothelial cells, or microvessels, tissues or organs in which the skin microvessel endothelial cells reside. In an aspect, disclosed herein is a composition comprising a skin microvessel endothelial cell targeting agent which binds to a protein expressed on the surface of a microvessel endothelial cell in skin.

In some embodiments, the protein expressed on the surface of the skin microvessel endothelial cell is encoded by a gene exhibiting higher expression levels in skin venule endothelial cells compared to skin non-venule endothelial cells. Examples of such genes include, but are not limited to, Nrp2, Gpr1, C630004H02Rik, Fndc1, 2310046K01Rik, Insr, and Slco2a1. Examples of such genes also include, but are not limited to, Nrp2, Htr2b, Mr1, Lifr, Anxa1, Lphn2, Vamp5, Olr1, Eps8, Slco2b1, and Slco2a1.

In some embodiments, the protein expressed on the surface of the skin microvessel endothelial cell is encoded by a gene exhibiting higher expression levels in skin non-venule endothelial cells compared to skin venule endothelial cells. Examples of such genes include, but are not limited to, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. Examples of such genes also include, but are not limited to, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

In some aspects, a composition comprises an effective amount of an adipose tissue microvessel endothelial cell targeting agent described herein. The composition can be used for treating, diagnosing, and imaging applications involving adipose tissue microvessel endothelial cells, or microvessels, tissues or organs in which the adipose tissue microvessel endothelial cells reside. In an aspect, the disclosure provides a composition comprising an adipose tissue microvessel endothelial cell targeting agent which binds to a protein expressed on the surface of a microvessel endothelial cell in adipose tissue.

In some embodiments, the protein expressed on the surface of the adipose tissue microvessel endothelial cell is encoded by a gene exhibiting higher expression levels in adipose tissue venule endothelial cells compared to adipose tissue non-venule endothelial cells. Examples of such genes include, but are not limited to, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. Examples of such genes include, but are not limited to, Il1rl1, Tnfrsf1 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam.

In some embodiments, the protein expressed on the surface of the adipose tissue microvessel endothelial cell is encoded by a gene exhibiting higher expression levels in adipose tissue non-venule endothelial cells compared to adipose tissue venule endothelial cells. Examples of such genes include, but are not limited to, Adora2a, H2-Ab1, Hspg2, Gpr81, Kcna5, Jam3, and Gpc4. Examples of such genes include, but are not limited to, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some aspects, a composition comprises an effective amount of a lymph node microvessel endothelial cell targeting agent described herein. The composition can be used for treating, diagnosing, and imaging applications involving lymph node microvessel endothelial cells, or microvessels, tissues or organs in which the lymph node microvessel endothelial cells reside. In an aspect, the disclosure provides a composition comprising a lymph node microvessel endothelial cell targeting agent which binds to a protein expressed on the surface of a microvessel endothelial cell in the lymph nodes.

In some embodiments, the protein expressed on the surface of the lymph node microvessel endothelial cell is encoded by a gene exhibiting higher expression levels in lymph node venule endothelial cells compared to lymph node non-venule endothelial cells. Examples of such genes include, but are not limited to, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, and Il2rg.

In some embodiments, the protein expressed on the surface of the lymph node microvessel endothelial cell is encoded by a gene exhibiting higher expression levels in lymph node non-venule endothelial cells compared to lymph node venule endothelial cells. Examples of such genes include, but are not limited to, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. Examples of such genes include, but are not limited to, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

The disclosure contemplates the use of any targeting agent (e.g., a microvessel endothelial cell targeting agent, a venule endothelial cell targeting agent, a non-venule endothelial cell targeting agent, a skin microvessel endothelial cell targeting agent, an adipose tissue endothelial cell targeting agent, a lymph node endothelial cell targeting agent) that is capable of recognizing, binding to, or otherwise interacting with its intended target. Exemplary targeting agents include, but are not limited to, small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. Suitable target agents can be identified for any particular target based on the screening methods disclosed herein.

The compositions described herein can further comprise an agent (e.g., a therapeutic agent, a diagnostic agent, or an imaging agent described herein). Exemplary agents include, but are not limited to, small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. In some embodiments, an exemplary agent includes an aptide.

In some embodiments, the targeting agent (e.g., a microvessel endothelial cell targeting agent, a venule endothelial cell targeting agent, a non-venule endothelial cell targeting agent, a skin microvessel endothelial cell targeting agent, an adipose tissue endothelial cell targeting agent, a lymph node endothelial cell targeting agent) is coupled to the agent. The disclosure contemplates any method of coupling an agent and a targeting agent which is available to the skilled artisan. In some embodiments, the targeting agent (e.g., a microvessel endothelial cell targeting agent, a venule endothelial cell targeting agent, a non-venule endothelial cell targeting agent, a skin microvessel endothelial cell targeting agent, an adipose tissue endothelial cell targeting agent, a lymph node endothelial cell targeting agent) is coupled to the agent via a linker. In some embodiments, the targeting agent or the agent is coupled to a detectable reporter.

In some embodiments, the targeting agent (e.g., a microvessel endothelial cell targeting agent, a venule endothelial cell targeting agent, a non-venule endothelial cell targeting agent, a skin microvessel endothelial cell targeting agent, an adipose tissue endothelial cell targeting agent, a lymph node endothelial cell targeting agent) is internalized into or transported across the endothelial cells lining the microvessel. Internalization of the targeting agent into the endothelial cells lining the microvessel causes the targeting agent to accumulate in the microvessel, tissue, or organ in which the microvessel resides. In some embodiments, the targeting agent accumulates in the subject's skin. In such embodiments, the composition can be used for treating or preventing a skin inflammatory disease (e.g., a skin inflammatory disease disclosed herein). In some embodiments, the targeting agent accumulates in the subject's adipose tissue. In such embodiments, the composition can be used for treating or preventing a disease (e.g., a characterized by visceral fat inflammation or an adipose tissue associated disorder). In some embodiments, the targeting agent accumulates in the venule endothelial cells in the subject's lymph nodes. In such embodiments, the composition can be used for treating or preventing a disease characterized by lymphadenitis. In certain embodiments, the targeting agent does not accumulate in non-target tissues or only accumulates in negligible amounts in non-target tissues.

Internalization of the targeting agent into the endothelial cells lining the microvessel also causes the agent to accumulate in the tissue in which the microvessel resides. In some embodiments, the agent accumulates in the subject's skin. In some embodiments, the agent accumulates in the subject's adipose tissue. In some embodiments, the agent accumulates in the subject's lymph nodes. In such embodiments, the agent induces a localized effect in the tissue. In some embodiments, the agent does not accumulate in non-target tissue.

Kits

An agent described herein can be provided in a kit. The kit includes (a) the agent, e.g., a composition that includes the agent, and (b) informational material. The informational material can be descriptive, instructional, marketing or other material that relates to the methods described herein and/or the use of the agent for the methods described herein. For example, the informational material describes methods for administering a targeting agent described herein (e.g., a microvessel endothelial cell targeting agent, a venule endothelial cell targeting agent, a non-venule endothelial cell targeting agent, a skin microvessel endothelial cell targeting agent, an adipose tissue endothelial cell targeting agent, a lymph node endothelial cell targeting agent), or a composition thereof, to a subject to treat or prevent a disorder described herein.

In one embodiment, the informational material can include instructions to administer the agent in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the modulator and/or its use in the methods described herein. Of course, the informational material can also be provided in any combination of formats.

In addition to the agent or the composition of the kit can include other ingredients, such as a solvent or buffer, a stabilizer or a preservative, and/or a second agent for treating a condition or disorder described herein, e.g. an inflammatory disease). Alternatively, the other ingredients can be included in the kit, but in different compositions or containers than the agent. In such embodiments, the kit can include instructions for admixing the agent and the other ingredients, or for using the targeting agent together with the other ingredients.

The agent can be provided in any form, e.g., liquid, dried or lyophilized form. It is preferred that the agent be substantially pure and/or sterile. When the agent is provided in a liquid solution, the liquid solution preferably is an aqueous solution, with a sterile aqueous solution being preferred. When the agent is provided as a dried form, reconstitution generally is by the addition of a suitable solvent. The solvent, e.g., sterile water or buffer, can optionally be provided in the kit.

The kit can include one or more containers for the composition containing the agent. In some embodiments, the kit contains separate containers, dividers or compartments for the agent (e.g., in a composition) and informational material. For example, the agent (e.g., in a composition) can be contained in a bottle, vial, or syringe, and the informational material can be contained in a plastic sleeve or packet. In other embodiments, the separate elements of the kit are contained within a single, undivided container. For example, the agent (e.g., in a composition) is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agent (e.g., in a composition). For example, the kit includes a plurality of syringes, ampules, foil packets, or blister packs, each containing a single unit dose of the agent. The containers of the kits can be air tight and/or waterproof.

The agent (e.g., in a composition) can be administered to a subject, e.g., an adult subject, e.g., a subject suffering from a disorder characterized by visceral fat inflammation (e.g., metabolic syndrome). The method can include evaluating a subject, e.g., to detect a polymorphism of HMGA1 in the subject, and thereby identifying a subject as having metabolic syndrome or being pre-disposed to such disorder.

Agents

The disclosure contemplates the use of various agents in connection with the methods and compositions described herein. Certain of the methods, compositions, and kits described herein relate to delivering agents to microvessel endothelial cells. In particular, the work described herein identified the surface markers described herein as being over- or under-represented in venules compared to non-venules globally, as well as in various tissues (e.g., skin, adipose tissue, and lymph node). As described herein, and as will be appreciated by those skilled in the art, the surface markers can be used in methods, compositions, and kits for targeting endothelial cells or microvessels, as well as for identifying agents that target endothelial cells or microvessels, and in methods, compositions, and kits for treating disorders associated with microvessels or microvessel endothelial cells.

Certain methods, compositions, kits and agents contemplated herein modulate a biological response (e.g., an inflammatory response). By way of representative example, in the contexts of decreasing an inflammatory response or inflammation, the methods, compositions, kits and agents contemplated herein can decrease the inflammatory response or inflammation by at least about 10%, 20%, 30%, 40%, 50%, 60%, 70%, 80, 90%, or as much as 100% as compared to a reference level (e.g., an amount of inflammation before employing the method, composition, kit and/or agent). In the contexts of increasing an inflammatory response or inflammation, the methods, compositions, kits and agents contemplated herein can increase the inflammatory response or inflammation by at least about 10%, 20%, 30%, 40%, 50%, 60%, 70%, 80, 90%, or as much as 100%, at least about a 2-fold, or at least about a 3-fold, or at least about a 4-fold, or at least about a 5-fold or at least about a 10-fold increase, or any increase between 2-fold and 10-fold or greater as compared to a reference level (e.g., an amount of inflammation before employing the method, composition, kit and/or agent).

As used broadly herein, the term "modulate" means to cause or facilitate a qualitative or quantitative change, alteration, or modification in a molecule, a process, pathway, or phenomenon of interest. Without limitation, such change may be an increase, decrease, a change in binding characteristics, or change in relative strength or activity of different components or branches of the process, pathway, or phenomenon. The term "modulator" broadly refers to any molecule or agent that causes or facilitates a qualitative or quantitative change, alteration, or modification in a process, pathway, or phenomenon of interest. As used herein, the term "modulator" comprises both inhibitors and activators of a biological pathway or target. As used herein, the phrase "modulation of a biological pathway" refers to modulation of activity of at least one component of the biological pathway. It is contemplated herein that modulator of the signaling pathway can be, for example, a receptor ligand (e.g., a small molecule, an antibody, an siRNA), a ligand sequestrant (e.g., an antibody, a binding protein), a modulator of phosphorylation of a pathway component or a combination of such modulators.

One of skill in the art can easily test an agent to determine if it modulates a signaling pathway by assessing, for example, phosphorylation status of the receptor or expression of downstream proteins controlled by the pathway in cultured cells and comparing the results to cells not treated with a modulator. A modulator is determined to be a signaling pathway modulator if the level of phosphorylation of the receptor or expression of downstream proteins in a culture of cells is reduced by at least 20% compared to the level of phosphorylation of the receptor or expression of downstream proteins in cells that are cultured in the absence of the modulator; preferably the level of phosphorylation is altered by at least 30%, at least 40%, at least 50%, at least 60%, at least 70%, at least 80%, at least 90%, at least 95%, or at least 99% in the presence of a pathway modulator.

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

Any suitable type of agent can be used as one of the agents, test agents, candidate agents, chemotherapeutic agents, cytotoxic agents, diagnostic agents, endothelial cell targeting agents (e.g., venule endothelial cell targeting agents, non-venule endothelial cell targeting agents, skin venule endothelial cell targeting agents, skin non-venule endothelial cell targeting agents, adipose tissue venule endothelial targeting agents, adipose tissue non-venule endothelial cell targeting agents, lymph node venule endothelial cell targeting agents, lymph node non-venule endothelial cell targeting agents), imaging agents, therapeutic agents, anti-inflammatory agents described herein. Exemplary types of agents that can be used for such agents in the methods, compositions, and kits described herein include small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof. Aptides are also exemplary agent that can be used in the methods, compositions, and kits described herein.

As used herein, the term "small molecule" can refer to agents that are "natural product-like," however, the term "small molecule" is not limited to "natural product-like" agents. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular weight equal to or less than 700 Daltons.

As used herein, an "RNA interference molecule" refers to an agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (e.g. The succession of letters used as abbreviations for bases) that biochemically characterizes a specific nucleic acid. A polynucleotide sequence presented herein is presented in a 5' to 3' direction unless otherwise indicated.

The nucleic acid molecules that modulate the biological pathways or targets described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. Proc. Natl. Acad. Sci. USA 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (e.g., the succession of letters or three letter codes used as abbreviations for amino acid names) that biochemically characterizes a polypeptide. A polypeptide sequence presented herein is presented in an N-terminal to C-terminal direction unless otherwise indicated.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI.

Certain methods, compositions, and kits contemplate agents that target microvessel endothelial cells (e.g., microvessel endothelial cell targeting agents) by recognizing, binding to, or otherwise interacting with microvessel endothelial cell surface markers. Exemplary microvessel endothelial cell targeting agents can recognize, bind to, or otherwise interact with a microvessel endothelial cell surface marker including, but not limited to, Sele, Selp, Il6st, Plxnb2, Lepr, Bst1, Icam1; Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3; Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg; Gpr182, Slco2b1; Cd63, Sirpa, Slc2a1, Vmn1r100, Vmn1r148, Vmn1r132, Vmn1r125; Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Nt5e, Il13ra1, Cysltr1, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9; Adora2a, H2-Ab1, Hspg2, Gpr81, Kcna5, Jam3, Gpc4); Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Notch1, Thbd, Npr2, Clstn1, Cd36, Scarb1, Flt1, Dysf, Mgll, Klrb1f, Plxnd1, Tm6sf1, Ceacam1, Lrp3, Cdh13, Nrp1, Dok4, Tns1, Cxcr4, Atp1b1, Car4, Cd7, Itga1, Gja5, Aqp7, Gja4, Mlec, P2ry2, Cd97, Unc5b, Lpar6, Sema6d, Ppap2b, Lpar4, Ly86, H2-Aa, and Cd74. In some embodiments, exemplary microvessel endothelial cell targeting agents can recognize, bind to, or otherwise interact with a microvessel endothelial cell surface marker including, but not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsf11a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, Il13ra1, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some contexts, a microvessel endothelial cell targeting agent specifically targets all venules and is referred to as a "venule endothelial cell targeting agent." Venule endothelial cell targeting agents recognize, bind to, or otherwise interact with proteins expressed on the surface of venule endothelial cells referred to herein as "venule endothelial cell surface markers." Exemplary venule endothelial cell targeting agents can recognize, bind to, or otherwise interact with a venule endothelial cell surface marker including, but not limited to, Sele, Selp, Il6st, Plxnb2, Lepr, Bst1, Icam1, Nrp2, Gpr1, C630004H02Rik, Fndc1, 2310046K01Rik, Insr, Slco2a1, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, Atp1b3, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg, Gpr182 Slco2b1, Cd63, Sirpa, Slc2a1, Vmn1r100, Vmn1r148, Vmn1r132, Vmn1r125, Il1r1, Tbc1d8, Cd55, Cadm3, Htr2a, Csf2rb2, Amigo2, Adrb2, Procr, Lbp, Ehd4, Kcnb1, Tspan5, Clca1, Gem, Ctnnal1, Tacr1, Ret, Anpep, Gpm6a, Insr, Nt5e, Mras, Il13ra1, and Cysltr1. In some embodiments, exemplary venule endothelial cell targeting agents can recognize, bind to, or otherwise interact with a venule endothelial cell surface marker including, but not limited to, Sele, Selp, Kcnh1, Tbc1d8, Cd55, Gpr126, C630004H02Rik, Plxnb2, Sirpa, Vcam1, Clca2, Lepr, Bst1, Pcdh7, Met, Nt5e, Cysltr1, Nrp2, Htr2b, Mr1, Lifr, Anxa1, Lphn2, Vamp5, Olr1, Eps8, Slco2b1, Slco2a1, Tnfrsfl 1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, L1cam, Ly96, Faim3, Sell, Slc2a12, Ggt5, Madcam1, Cd63, Rtn4rl1, Ccr7, Cd79b, Tshr, Ly86, Sema5a, Sntb1, Lynx1, Ly6i, Robo1, Robo2, H2-DMa, H2-Aa, H2-M2, Dsg2, Cd74, Cdh2, Slc26a2, Vldlr, Fads2, Ms4a1, Abca2, Flrt3, Cldn11, Mme, Frrs1, Cd53, Il11ra2///Il11ra1, Hvcn1, Daglb, P2rx2, Cldn13, Slc1a5, Cd79a, Grin2d, Lyve1, Fgfr2, Cdh3, Fcer2a, Csmd1, Marveld3, Ldlr, Pvrl1, Stra6, Ccbp2, Chrnb4, Tspan3, Tspan7, Chic1, Gpr182, H60b, Ppap2c, Celsr1, Glycam1, Slc37a1, Cd59a, Slc2a1, Tnfrsf9, Tes, Pglyrp1, Il27ra, Eda2r, Il1r1, Gpr1, Cadm3, Itgb4, Il6st, Htr2a, Stab1, Amigo2, Fndc1, Cd14, Adrb2, Atp8b1, Slc52a3, Procr, Lbp, Ehd4, Tspan5, Clca1, Gem, Tlr4, Ctnnal1, Tacr1, Anpep, Gpm6a, Insr, Icam1, Mras, and Il13ra1.

It should be appreciated that because Darc is expressed on red blood cells, Darc is not a suitable venule endothelial cell surface marker for which a venule endothelial cell targeting agent can be employed to selectively target venule endothelial cells.

In some contexts, a microvessel endothelial cell targeting agent specifically targets all non-venules and is referred to herein as a "non-venule endothelial cell targeting agent." Non-venule endothelial cell targeting agents recognize, bind to, or otherwise interact with proteins expressed on the surface of non-venule endothelial cells referred to herein as "non-venule endothelial cell surface markers." Exemplary non-venule endothelial cell targeting agents can recognize, bind to, or otherwise interact with a non-venule endothelial cell surface marker including, but not limited to, Flt4, Jup, Lgals3 bp, Ednrb, Ptp4a3, Gpihbp1, Notch4, Slc9a3r2, Prnd, Sdc3, Alpl, Cldn15, Kdr, Slc6a6, Podxl, Efnb2, Sema7a, Itm2a, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, Ccr9, Adora2a, H2-Ab1, Hspg2, Gpr81, Kcna5, Jam3, Gpc4, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, Slc7a5, Tns1, Cxcr4, Atp1b1, Car4, Cd7, Itga1, Gja5, Laptm5, Aqp7, Gja4, Mlec, P2ry2, Cd97, Unc5b, Lpar6, Sema6d, Ppap2b, Lpar4, Ly86, H2-Aa, and Cd74. In some embodiments, exemplary non-venule endothelial cell targeting agents can recognize, bind to, or otherwise interact with a non-venule endothelial cell surface marker including, but not limited to, Cxcr4, Unc5b, Flt4, Ednrb, Notch4, Prnd, Gja5, Gja4, Alpl, Kcna5, P2ry2, Efnb2, Itm2a, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Tyrobp, Nkg7, Siglech, Itga1, Ifitm1, Lair1, Cd37, Gprc5b, Igsf6, Cd209a, Cd209d, Tlr9, Ccr9, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, A630033H20Rik, Kcnj2, Abca8b, F2r, Robo2, Ms4a1, Arhgef26, Tttl7, Clca5, TVmn1r100, Vmn1r148, Vmn1r114, Vmn1r132, Vmn1r93, Vmn1r-ps79, Vmn1r125, Epor, Jam3, Atp1b1, Car4, Jup, Lgals3 bp, Ppap2a, Itga1, Gpihbp1, Slc9a3r2, Sdc3, Aqp7, Mlec, Slc6a6, Irak2, Klrb1f, Cd97, Gpc4, Ramp3, Olfr1396, Slc1a1, Cldn15, Cd109, Cd79b, Ly86, Chrm3, Ptger4, and Sema7a.

In some aspects, a microvessel endothelial cell targeting agent specifically targets skin and is referred to herein as a "skin microvessel endothelial cell targeting agent." In some contexts, a skin microvessel endothelial cell targeting agent specifically targets all skin venules and is referred to herein as a "skin venule endothelial cell targeting agent." Skin venule endothelial cell targeting agents recognize, bind to, or otherwise interact with proteins expressed on the surface of skin venule endothelial cells referred to herein as "skin venule endothelial cell surface markers." Exemplary skin venule endothelial cell targeting agents can recognize, bind to, or otherwise interact with a skin venule endothelial cell surface marker including, but not limited to, Nrp2, Gpr1, C630004H02Rik, Fndc1, 2310046K01Rik, Insr, and Slco2a1. In some embodiments, exemplary skin venule endothelial cell targeting agents can recognize, bind to, or otherwise interact with a skin venule endothelial cell surface marker including, but not limited to, Nrp2, Htr2b, Mr1, Lifr, Anxa1, Lphn2, Vamp5, Olr1, Eps8, Slco2b1, and Slco2a1. In some contexts, a skin microvessel endothelial cell targeting agent specifically targets all skin non-venules and is referred to herein as a "skin non-venule endothelial cell targeting agent." Skin non-venule endothelial cell targeting agents recognize, bind to, or otherwise interact with proteins expressed on the surface of skin non-venule endothelial cells referred to herein as "skin non-venule endothelial cell surface markers." Exemplary skin non-venule endothelial cell targeting agents can recognize, bind to, or otherwise interact with a skin non-venule endothelial cell surface marker including, but not limited to, Sell, Ptprc, Rgs1, Fcer1g, Cd68, Cd79b, Cd180, Ly6d, Cldn5, Cd200, H2-DMa, H2-Eb1, Fads2, Cd44, Cd53, Alox5ap, Selplg, Irak2, Cd69, Tyrobp, Nkg7, Siglech, Cd37, Gprc5b, Cd209a, Cd209d, and Ccr9. In some embodiments, exemplary skin non-venule endothelial cell targeting agents can recognize, bind to, or otherwise interact with a skin non-venule endothelial cell surface marker including, but not limited to, Gm7609, Tns1, Ptprc, Rgs1, Fcer1g, Itgb2, Slc41a2, Cd68, Cd300c, Cd7, Cd180, Gpr183, Ptp4a3, Nckap1l, Il7r, Sla, Ly6d, Il2rb, Slc38a1, Cldn5, Tigit, Cd200, H2-DMa, H2-Ab1, H2-Eb1, H2-Aa, Rftn1, 9430020K01Rik, Cd74, Fads2, Itga4, Slc28a2, Cd44, Stmn2, Cd53, Laptm5, Kit, Hvcn1, Gpr30, Alox5ap, Prom1, Selplg, Cd8b1, Cd4, Cd69, Cd79a, Tyrobp, Nkg7, Siglech, Itga1, Ifitm1, Lair1, Cd37, Gprc5b, Igsf6, Cd209a, Cd209d, Tlr9, and Ccr9.

In some aspects, a microvessel endothelial cell targeting agent specifically targets adipose tissue and is referred to herein as an "adipose tissue microvessel endothelial cell targeting agent." In some contexts, an adipose tissue microvessel endothelial cell targeting agent specifically targets all adipose tissue venules and is referred to as an "adipose tissue venule endothelial cell targeting agent." Adipose tissue venule endothelial cell targeting agents recognize, bind to, or otherwise interact with proteins expressed on the surface of adipose tissue venule endothelial cells referred to herein as "adipose tissue venule endothelial cell surface markers." Exemplary adipose tissue venule endothelial cell targeting agents can recognize, bind to, or otherwise interact with an adipose tissue venule endothelial cell surface marker including, but not limited to, Il1rl1, Gm7609, Rgs1, Gpr126, P2rx1, Slc6a4, Itgb4, A530099J19Rik, Fcer1g, Fcer1a, Slc7a8, Nckap1l, Sla, Emp2, Entpd1, Slc18a2, Ms4a2, Cd59a, Adora3, Ddah1, Cpa3, I830077J02Rik, Vcam1, Laptm5, Kit, P2rx4, Cmklr1, Lat2, Pilra, Aqp1, Gp9, Slc6a12, Emp1, Cd33, Mrgprb1, Mrgprb2, Slc7a5, Mras, and Atp1b3. In some embodiments, exemplary adipose tissue venule endothelial cell targeting agents can recognize, bind to, or otherwise interact with an adipose tissue venule endothelial cell surface marker including, but not limited to, Il1rl1, Tnfrsf1a, Mpz, Dnm3os, Icos1, Osbp18, Itga3, Flrt2, Sla, Csf2rb2, Slc2a13, Emp2, Dll1, Entpd1, Ptprj, Lrrn4, Sulf2, Kcnb1, Adora3, Laptm5, Ptafr, Agtrap, Kit, P2rx4, Upk3b, Cmklr1, Trpv4, Aqp1, Hrh1, Cd9, Kcne3, Slco3a1, Tm6sf2, Cdon, Olfr920, Itga9, Gria3, and L1cam. In some contexts, an adipose tissue microvessel endothelial cell targeting agent specifically targets all adipose tissue non-venules and is referred to herein as an "adipose tissue non-venule endothelial cell targeting agent." Adipose tissue non-venule endothelial cell targeting agents recognize, bind to, or otherwise interact with proteins expressed on the surface of adipose tissue non-venule endothelial cells referred to herein as "adipose tissue non-venule endothelial cell surface markers." Exemplary adipose tissue non-venule endothelial cell targeting agents can recognize, bind to, or otherwise interact with an adipose tissue non-venule endothelial cell surface marker including, but not limited to, Adora2a, H2-Ab1, Hspg2, Gpr81, Kcna5, Jam3, and Gpc4. In some embodiments, exemplary adipose tissue non-venule endothelial cell targeting agents can recognize, bind to, or otherwise interact with an adipose tissue non-venule endothelial cell surface marker including, but not limited to, Kcnj2, Abca8b, F2r, Robo2, Ms4a1, Arhgef26, Ttll7, Clca5, TVmn1r100, Vmn1r148, Vmn1r114, Vmn1r132, Vmn1r93, Vmn1r-ps79, Vmn1r125, Epor, and Jam3.

In some aspects, a microvessel endothelial cell targeting agent specifically targets lymph nodes and is referred to herein as a "lymph node microvessel endothelial cell targeting agent." In some contexts, a lymph node microvessel endothelial cell targeting agent specifically targets all lymph node venules and is referred to as "lymph node venule endothelial cell targeting agent." Lymph node venule endothelial cell targeting agents recognize, bind to, or otherwise interact with proteins expressed on the surface of lymph node venule endothelial cells referred to herein as "lymph node venule endothelial cell surface markers." Exemplary lymph node venule endothelial cell targeting agents can recognize, bind to, or otherwise interact with a lymph node venule endothelial cell surface marker including, but not limited to, Ly96, Ddr2, Madcam1, Ctla2a, Sema5a, Enpp2, Ly6i, Celsr1, Glycam1, Robo1, Dsg2, Cdh2, Abca2, Snap23, Pcdh7, Met, Vmn2r43, Slc1a5, Pglyrp1, Olfr538, Lyve1, Il27ra, Pvrl1, Stra6, Tspan3, Tspan7, Il2rg. In some contexts, a lymph node microvessel endothelial cell targeting agent specifically targets all lymph node non-venules and is referred to herein as a "lymph node non-venule endothelial cell targeting agent." Lymph node non-venule endothelial cell targeting agents recognize, bind to, or otherwise interact with proteins expressed on the surface of lymph node non-venule endothelial cells referred to herein as "lymph node non-venule endothelial cell surface markers." Exemplary lymph node non-venule endothelial cell targeting agents can recognize, bind to, or otherwise interact with a lymph node non-venule endothelial cell surface marker including, but not limited to, Sdpr, Tns1, Mpzl1, Palm, Ptprb, Enpp3, Marcks, Ramp3, Pmp22, Kcnj2, Olfr1396, Arrdc3, Ppap2a, Ptprg, Spata13, Fzd6, Tenc1, Ly6c1, Ly6c2, Tmem204, Ptprm, Spry4, Sorbs1, Aplnr, Mertk, Lbp, Notch1, Thbd, Npr2, Clstn1, Cd36, Scarb1, Flt1, Dysf, Mgll, Klrb1f, Emp1, Plxnd1, Tm6sf1, Ceacam1, Lrp3, Cdh13, Nrp1, Dok4, and Slc7a5. In some embodiments, exemplary lymph node non-venule endothelial cell targeting agents can recognize, bind to, or otherwise interact with a lymph node non-venule endothelial cell surface marker including, but not limited to, Mtap2, Cxcr7, Palm, Tbxa2r, Enpp3, Pmp22, Mmd, Ptprg, Spata13, Lpar6, Fzd6, Npr3, Itgb5, Scube3, Spry4, Ms4a4d, Fas, Aplnr, Sema6d, Mertk, Thbd, Enpep, Npr2, Ppap2b, Clstn1, Agrn, Cd36, Mlec, Gpr81, Cald1, Dysf, Mgll, Tspan12, Podxl, Plxnd1, Kcne3, Lrp3, Aqp11, F2rl3, Cdh13, Nrp1, Dok4, Fxyd6, Ephb1, Rtp3, Ccrl2, Tgfbr2, Lpar4, and A630033H20Rik.

The disclosure contemplates employing any agent described herein in combination with any other agent which would be desirable for the skilled artisan to combine. By way of illustration, and not of limitation, any of the microvessel endothelial cell targeting agents described herein can be used to target any agent described herein (e.g., anti-inflammatory agents, diagnostic agents, imaging agents, therapeutic agents, cytotoxic agents, chemotherapeutic agents, etc.) specifically to microvessel endothelial cells. In such contexts, the microvessel endothelial cell targeting agent can be coupled to the agent to be targeted to the microvessel endothelial cell. The microvessel endothelial cell targeting agent can be coupled directly to the agent. Alternatively, the microvessel endothelial cell targeting agent can be coupled to the agent via a linker. Any suitable linker can be used.

It may also be desirable to couple the microvessel endothelial cell targeting agent to a detectable reporter (e.g., a fluorescent reagent, e.g., GFP). Alternatively, the agent can be coupled to a detectable reporter. In some instances, a detectable reporter can be coupled to the microvessel endothelial cell targeting agent and the agent. Any technique available to the skilled artisan can be used to couple the microvessel endothelial cell targeting agent to the agent to be targeted. It should be appreciated, however, that in some contexts, the microvessel endothelial cell targeting agent itself may exhibit a desired biological effect (e.g., by recognizing, binding to, or otherwise interacting with the endothelial cell surface marker in a way that interferes with leukocyte trafficking in the endothelial cell expressing the endothelial cell surface marker).

Generally, an agent described herein can be used in combination with a therapeutic agent (e.g., a pharmaceutically active agent, e.g., a drug approved by a regulatory agency). The therapeutic agent may act synergistically with the agent described herein, or they may independently exert their intended effects. The disclosure contemplates any therapeutic agent which a skilled artisan would use in connection with a method, composition, or kit described herein (e.g., conventional treatments for microvessel endothelial cell-associated disorders, venular disorders, nonvenular disorders, skin disorders, adipose tissue disorders (e.g., a disease characterized by visceral fat inflammation), lymph node disorders (e.g., a disease characterized by lymphadenitis)). Those skilled in the art will also appreciate that that the microvessel endothelial cell targeting agents described herein can be used to target a therapeutic agent to a microvessel endothelial cell, a microvessel or a tissue or organ adjacent to a microvessel endothelial cell.

In some contexts, it may be desirable to employ a cytotoxic agent in combination with an agent described herein (e.g., to treat, prevent, or ameliorate a symptom of, a disorder or disease characterized by lymphadenitis (e.g., cancer or infection). Exemplary cytotoxic agents include but are not limited to taxol; a nitrogen mustard selected from the group consisting of mechlorethamine, cyclophosphamide, melphalan, uracil mustard and chlorambucil; thiotepa; busulfan; a nitrosourea selected from the group consisting of carmustine, lomustine, semustine and streptozocin; dacarbazine; methotrexate; fluorouracil, cytarabine, azaribine; a purine analogs selected from the group consisting of mercaptopurine and thioguanine; a vinca alkaloids selected from the group consisting of vinblastine and vincristine; an antibiotic selected from the group consisting of dactinomycin, daunorubicin, doxorubicin, bleomycin, mithramycin and mitomycin; L-asparaginase; cisplatin; hydroxyurea; procarbazine; anti-virals; vaccines; and photodynamic dyes. In some contexts, it may be desirable to employ a chemotherapeutic agent in combination with an agent described herein (e.g., to treat, prevent, or ameliorate a symptom of, a disorder or disease characterized by lymphadenitis (e.g., cancer). Exemplary chemotherapeutic agents include, but are not limited to, vinblastine, doxorubicin, bleomycin, methotrexate, 5-fluorouracil, 6-thioguanine, cytarabine, cyclophosphamide and cisplatinum.

In some contexts, it may be desirable to employ an anti-inflammatory agent in combination with an agent described herein (e.g., to treat, prevent, or ameliorate a symptom of, a disorder involving leukocyte trafficking, e.g., inflammatory disease). Exemplary anti-inflammatory agents include, but are not limited to effective amounts of non-steroidal anti-inflammatory drugs (NSAIDs), including but not limited to: diclofenac potassium, diclofenac sodium, etodolac, indomethicin, ketorolac tromethamine, sulindac, tometin sodium, celecoxib, meloxicam, valdecoxib, floctafenine, mefenamic acid, nabumetone, meloxicam, piroxicam, tenoxicam, fenoprofen calcium, flubiprofen, ibuprofen, ketoprofen, naproxen, naproxen sodium, oxaprozin, tiaprofenic acid, acetylsalicylic acid, diflunisal, choline magnesium trisalicylate, choline salicylate, triethanolamine salicylate, COX1 inhibitors, COX2 inhibitors (e.g., Vioxx™, and Celebrex™). A variety of herbs and natural health products may also be used to provide anti-flammatory treatment, including but not limited to: green tea, fish oil, vitamin D, antioxidant vitamins and minerals (e.g., B carotene, vitamin A, vitamin C, vitamin D, vitamin E, co-enzyme Q10, selenium, etc.), resveratrol, turmeric, bromelain, boswellia, feverfew, quercetin, ginger, rosemary, oregano, cayenne, clove, nutmeg, willowbark.

In some contexts, an agent described herein can be administered with an antigen (e.g., to induce an immune response). In some embodiments, an adjuvant can be used in combination with the antigen.

An agent described herein can also be used in combination with an imaging agent. An agent (e.g., an endothelial cell targeting agent described herein) can be attached to imaging agents for imaging and diagnosis of various diseased organs, tissues or cell types. The agent can be labeled or conjugated a fluorophore or radiotracer for use as an imaging agent. Many appropriate imaging agents are known in the art, as are methods for their attachment to agents (e.g., attaching an imaging agent to a proteins or peptides using metal chelate complexes, radioisotopes, fluorescent markers, or enzymes whose presence can be detected using a colorimetric markers (such as, but not limited to, urease, alkaline phosphatase, (horseradish) hydrogen peroxidase and glucose oxidase)). An agent may also be dual labeled with a radioisotope in order to combine imaging through nuclear approaches and be made into a unique cyclic structure and optimized for binding affinity and pharmacokinetics. Such agents can be administered by any number of methods known to those of ordinary skill in the art including, but not limited to, oral administration, inhalation, subcutaneous (sub-q), intravenous (I.V.), intraperitoneal (I.P.), intramuscular (I.M.), or intrathecal injection. The methods, compositions, and kits described herein can be used alone or in combination with other techniques, to diagnose access and monitor and direct therapy of leukocyte trafficking associated disorders. In some contexts, the imaging agent can be used for detecting and/or monitoring tumors or sites of metastasis in a subject. For example, an agent (e.g., microvessel endothelial cell targeting agent) can be administered in vivo and monitored using an appropriate label. Exemplary methods for detecting and/or monitoring an agent labeled with an imaging agent in vivo include Gamma Scintigraphy, Positron Emission Tomography (PET), Single Photon Emission Computer Tomography (SPECT), Magnetic Resonance Imaging (MRI), X-ray, Computer Assisted X-ray Tomography (CT), Near Infrared Spectroscopy, and Ultrasound. These techniques provide information regarding detection of neoplastic involvement, particularly of inaccessible nodes in subjects with malignant diseases. Knowledge on the size of the node and the filling of nodes can also be instructive. For example, agents or compositions targeted to the lymph nodes in detection applications will contain suitable contrast or imaging agents such as ferromagnetic materials such as iron oxide, perfluorochemicals such as perfluorooctylbromide, or gamma emitting radiolabels such as Technetium-99m, Indium-111, Gallium-67, Thallium-201, Iodine-131, 125, or 123, positron emitting radiolabels such as Fluorine-18, or those produced by neutron activation such as Samarium-153.

Imaging agents of use in the disclosure include radioisotopes and dyes. Any conventional method according to radiolabeling which is suitable for labeling isotopes for in vivo use will be generally suitable for labeling detection agents according to the disclosure. Internal detection procedures include intraoperative, intravascular or endoscopic, including laproscopic, techniques, both surgically invasive and noninvasive.

For example, when detecting a lymph node, a high signal-to-background ratio should to be achieved. Therapy also requires a high absolute accretion of the therapeutic agent in the lymph node, as well as a reasonably long duration of uptake and binding.

Suitable radioisotopes for the methods of the disclosure include: Actinium-225, Astatine-211, Iodine-123, Iodine-125, Iodine-126, Iodine-131, Iodine-133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium-121m, Tellurium-122m, Tellurium-125m, Thulium-165, Thulium-167, Thulium-168, Technetium-99m, Fluorine-18, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, Gold-199, Cobalt-57, Cobalt-58, Chromium-51, Iron-59, Selenium-75, Thallium-201, and Ytterbium-169. The most preferred radioisotope for use in the current invention is Technetium-99m. Preferably the radioisotope will emit a particle or ray in the 10-7,000 keV range, more preferably in the 50-1,500 keV range, and most preferably in the 80-250 keV range.

Isotopes preferred for external imaging include: Iodine-123, Iodine-131, Indium-111, Gallium-67, Ruthenium-97, Technetium-99m, Cobalt-57, Cobalt-58, Chromium-51, Iron-59, Selenium-75, Thallium-201, and Ytterbium-169. Technetium-99m is the most preferred radioisotope for external imaging in the disclosure.

Isotopes most preferred for internal detection include: Iodine-125, Iodine-123, Iodine-131, Indium-111, Technetium-99m and Gallium-67. Technetium-99m is the most preferred isotope for internal detection.

In some contexts, an agent described herein can be employed in combination with a diagnostic agent.

Formulations and Administration

For administration to a subject, the inhibitors, modulators, or other agents described herein can be administered orally, parenterally, for example, subcutaneously, intravenously, intramuscularly, intraperitoneally, by intranasal instillation, or by application to mucous membranes, such as, that of the nose, throat, and bronchial tubes. For a comprehensive review on drug delivery strategies, see Ho et al., Curr. Opin. Mol. Ther. (1999), 1:336-3443; Groothuis et al., J. Neuro Virol. (1997), 3:387-400; and January, Drug Delivery Systems: Technologies and Commercial Opportunities, Decision Resources, 1998, content of all which is incorporate herein by reference.

They can be administered alone or with suitable pharmaceutical carriers, and can be in solid or liquid form such as, tablets, capsules, powders, solutions, suspensions, or emulsions.

As used herein, the term "administered" refers to the placement of an agent described herein, into a subject by a method or route which results in at least partial localization of the agent at a desired site. An agent described herein can be administered by any appropriate route which results in effective treatment in the subject, i.e. administration results in delivery to a desired location in the subject where at least a portion of the composition delivered. Exemplary modes of administration include, but are not limited to, injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

The agents can be formulated in pharmaceutically acceptable compositions which comprise a therapeutically-effective amount of the agent, formulated together with one or more pharmaceutically acceptable carriers (additives) and/or diluents. The agents can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, agents can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the pharmaceutically acceptable carrier, diluent, or excipient does not comprise any of the above mentioned carriers, diluents, or excipients in their naturally occurring form. In some embodiments, the pharmaceutically acceptable carrier, diluent, or excipient comprise synthetic derivatives of any of the above mentioned carriers, diluents, or excipients which comprise at least one modification (e.g., addition of a methyl group) as compared to their naturally occurring counterpart.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

"PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

The agents can be formulated in a gelatin capsule, in tablet form, dragee, syrup, suspension, topical cream, suppository, injectable solution, or kits for the preparation of syrups, suspension, topical cream, suppository or injectable solution just prior to use. Also, agents can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., *Remington's Pharmaceutical Sciences*, Mack Publishing Co., Easton, Pa. 1985, 17th edition, Nema et al., *PDA J. Pharm. Sci. Tech.* 1997 51:166-171. Methods to make invention formulations include the step of bringing into association or contacting an agent with one or more excipients or carriers. In general, the formulations are prepared by uniformly and intimately bringing into association one or more agents with liquid excipients or finely divided solid excipients or both, and then, if appropriate, shaping the product.

The preparative procedure may include the sterilization of the pharmaceutical preparations. The agents may be mixed with auxiliary agents such as lubricants, preservatives, stabilizers, salts for influencing osmotic pressure, etc., which do not react deleteriously with the agents.

Examples of injectable form include solutions, suspensions and emulsions. Injectable forms also include sterile powders for extemporaneous preparation of injectible solutions, suspensions or emulsions. The agents of the disclosure can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatinA suitable carrier is 5% dextrose in saline. Frequently, it is desirable to include additives in the carrier such as buffers and preservatives or other substances to enhance isotonicity and chemical stability.

In some embodiments, agents described herein can be administrated encapsulated within a nanoparticle or microparticle (e.g., a lipid nanoparticle or microparticle). The present disclosure contemplates the use of any suitable nanoparticle or microparticle, as will be appreciated by the skilled artisan. For example, in the context of vascular delivery, a nanoparticle or microparticle of between about 1 µm and about 10 µm can be used. In some embodiments, the microparticle comprises a microparticle that is approved by a regulatory agency (e.g., Food and Drug Administration). In some embodiments, agents described herein can be administered encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., endothelial cells) can also be used as pharmaceutically acceptable carriers. In some embodiments, the agent is administered using polymeric nanoparticles, e.g., nanoparticles constructed from low molecular weight polyamines and lipids (see Dahlman and Barnes et al., "In vivo endothelial siRNA delivery using polymeric nanoparticles with low molecular weight," *Nature Nanotechnology* DOI: 10.1038/NNANO.2014.84 (2014), which is incorporated by reference herein).

In one embodiment, the agents are prepared with carriers that will protect the agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and PRIMOGEL™, and the like.

The agents can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, agents may be incorporated with excipients and used in the form of tablets, capsules, elixirs, suspensions, syrups, and the like. Such compositions and preparations should contain at least 0.1% of agent. The percentage of the agent in these compositions may, of course, be varied and may conveniently be between about 2% to about 60% of the weight of the unit. The amount of agent in such therapeutically useful compositions is such that a suitable dosage will be obtained. Preferred compositions according to the disclosure are prepared so that an oral dosage unit contains between about 100 and 2000 mg of agent.

Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The compositions can be given as a bolus dose, to maximize the circulating levels for the greatest length of time after the dose. Continuous infusion may also be used after the bolus dose.

The agents can also be administered directly to the airways in the form of an aerosol. For administration by inhalation, the agents in solution or suspension can be delivered in the form of an aerosol spray from pressured container or dispenser which contains a suitable propellant, e.g., a gas such as carbon dioxide, or hydrocarbon propellant like propane, butane or isobutene. The agents can also be administered in a no-pressurized form such as in an atomizer or nebulizer.

The agents can also be administered parenterally. Solutions or suspensions of these agents can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage. As used herein, "dosage unit" refers to physically discrete units suited as unitary dosages for the subject to be treated; each unit containing a predetermined quantity of agent calculated to produce the desired therapeutic effect in association with the required pharmaceutical carrier.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the agents are formulated into ointments, salves, gels, or creams as generally known in the art.

The agents can be administrated to a subject in combination with other pharmaceutically active agents. Exemplary pharmaceutically active agents include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990, the complete contents of all of which are incorporated herein by reference. In some embodiments, the pharmaceutically active agent is selected from the group consisting of butyrates, valproic acid, hydroxyuirae and Riluzole.

The agents and the other pharmaceutically active agent can be administrated to the subject in the same pharmaceutical composition or in different pharmaceutical compositions (at the same time or at different times). As an example, an endothelial cell targeting agent coupled to an anti-inflammatory agent and an additional agent described herein can be administrated to the subject in the same pharmaceutical composition or in different pharmaceutical compositions (at the same or at different times).

The amount of agent which can be combined with a carrier material to produce a single dosage form will generally be that amount of the agent which produces a therapeutic effect. Generally out of one hundred percent, this amount will range from about 0.1% to 99% of agent, preferably from about 5% to about 70%, most preferably from 10% to about 30%.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to the active ingredient, sucrose as a sweetening agent, methyl and propylparabens as preservatives, a dye, and flavoring such as cherry or orange flavor.

The pharmaceutical compositions can be included in a container, pack, or dispenser together with instructions for administration.

As used herein, the term "therapeutically effective amount" means an amount of the agent which is effective to deliver an agent to microvessel endothelial cells or to deliver the agent to microvessel endothelial cells in such a way that the microvessel endothelial cell targeting agent and/or agent are internalized into or transported across the microvessel endothelial cells and/or accumulate in a target cell, vessel, tissue, or organ. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in leukocyte trafficking based disorder (e.g., inflammatory diseases, e.g., autoimmune diseases, etc.).

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

The data obtained from the cell culture assays and animal studies can be used in formulating a range of dosage for use in humans. The dosage of such agents lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription based assays, GDF-8 binding assays, and immunological assays.

The dosage may be determined by a physician and adjusted, as necessary, to suit observed effects of the treatment. Generally, the compositions are administered so that the agent is given at a dose from 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. For antibody agents, one preferred dosage is 0.1 mg/kg of body weight (generally 10 mg/kg to 20 mg/kg). If the antibody is to act in the brain, a dosage of 50 mg/kg to 100 mg/kg is usually appropriate.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. Examples of dosing schedules are administration once a week, twice a week, three times a week, daily, twice daily, three times daily or four or more times daily.

Some Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein the term "comprising" or "comprises" is used in reference to compositions, methods, kits and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, kits and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this In some embodiments, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Examples

The work described herein capitalizes on methods to develop and exploit a proprietary discovery platform that will lead to a new generation of anti-inflammatory drugs that specifically target venular endothelium, either globally or exclusively in a selected tissue. This strategy is in stark contrast to other currently prevalent strategies that are largely based on systemic administration of anti-inflammatory drugs. One of the key anticipated benefits of the strategy is the reduction of adverse side effects in uninvolved tissue during anti-inflammatory treatment. In the following, we provide some examples of molecules and strategies that may be employed based on putative candidate genes disclosed herein.

Numerous surface molecules are disclosed herein and more are likely to be found as we apply our strategy to additional tissues. These molecules can be used to design novel strategies to deliver drugs to a specific vascular bed such as skin, adipose tissue or lymph node. For example, FceR1a is a surface receptor for IgE, which we unexpectedly discovered to be specifically expressed by venules in visceral adipose tissue, but not in skin or lymph nodes). Inflammation in visceral fat precipitated by high fat diet and obesity is thought to be a critical event in the pathogenesis of metabolic syndrome, hypertension, CVHD and type 2 diabetes. Selective targeting of adipose tissue venules with anti-inflammatory drugs offers the opportunity to dampen local inflammation and its detrimental sequalae with minimal off-target activity in other tissues.

In conclusion, inflammatory diseases are a major public health problem with few treatment options that are often poorly efficacious or fraught with significant side effects or both, leaving a substantial unmet need to develop better drugs to treat and prevent inflammatory diseases. None of the existing anti-inflammatory drugs specifically targets endothelial cells, let alone venules. Use of the methods described herein to isolate segmental endothelial cells from a variety of relevant tissues allows for the identification, for the first time, of candidate genes that represent an entirely novel class of targets for anti-inflammatory therapeutics. Such therapeutics may be small molecules, biologics, nucleotide-based agents or targeted carriers that selectively deliver one or more of these pharmacologically active agents to a relevant population of postcapillary venules. These agents would be employed for anti-inflammatory treatment of a variety of inflammatory disorders.

REFERENCES

1. Halin C, Rodrigo Mora J, Sumen C, von Andrian U H. In vivo imaging of lymphocyte trafficking. Annu Rev Cell Dev Biol. 2005; 21:581-603
2. Ley K, Gaehtgens P. Endothelial, not hemodynamic, differences are responsible for preferential leukocyte rolling in rat mesenteric venules. Circulation Research. 1991; 69:1034-1041
3. von Andrian U H, Mackay C R. T-cell function and migration. Two sides of the same coin. New Engl Jour Med. 2000; 343(14):1020-1034
4. Luster A. D., Alon R., von Andrian U. H. Immune cell migration in inflammation: present and future therapeutic targets. Nature Immunology. 2005; 6(12):1182-1190
5. Peiper S C, Wang Z-x, Neote K, et al. The Duffy antigen/receptor for chemokines (DARC) is expressed in endothelial cells of Duffy negative individuals who lack the erythrocyte receptor. J Exp Med. 1995; 181:1311-1317
6. Hadley T J, Lu Z H, Wasniowska K, et al. Postcapillary Venule Endothelial Cells in Kidney Express a Multispecific Chemokine Receptor That Is Structurally and Functionally identical to the erythroid isoform, which is the Duffy Blood Group Antigen. J Clin Invest. 1994; 94:985-991

All patents and other publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of delivering a targeting agent to a microvessel endothelial cell in adipose tissue or skin in a subject, comprising administering to the subject a microvessel endothelial cell targeting agent which binds to a protein encoded by Il6st expressed on the surface of a microvessel endothelial cell in adipose tissue or skin, wherein the microvessel endothelial cell targeting agent is delivered specifically to a microvessel endothelial cell in adipose tissue or skin expressing the protein encoded by Il6st, and causes an effect in the microvessel endothelial cell, or a microvessel, tissue or organ adjacent to the microvessel endothelial cell.

2. A method according to claim 1, wherein the microvessel endothelial cell targeting agent is internalized into or transported across the endothelial cells lining the microvessel.

3. A method according to claim 1, wherein the microvessel endothelial cell targeting agent is selected from the group consisting of antibodies; small organic or inorganic molecules; saccharides; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, dendrimers and aptamers; an extract made from biological materials selected from the group consisting of bacteria, plants, fungi, animal cells, and animal tissues; naturally occurring or synthetic compositions; and any combination thereof.

4. A method according to claim 1, wherein the microvessel endothelial cell targeting agent is selected from a therapeutic agent, an anti-inflammatory agent, a diagnostic agent, an imaging agent, a multi-purpose agent, and combinations thereof.

5. A method according to claim 1, wherein delivering a targeting agent to microvessel endothelial cells in adipose tissue or skin of the subject treats, prevents, or ameliorates a symptom of, a disease of adipose tissue or skin in the subject.

6. A method according to claim 5, wherein the disease is an inflammatory disease of adipose tissue or skin.

7. A method according to claim 6, wherein the inflammatory disease is selected from the group consisting of cancer, obesity-related insulin resistance, diabetes, polycystic ovary syndrome, metabolic syndrome, hypertension, cerebrovascular accident, myocardial infarction, congestive heart failure, cholecystitis, gout, osteoarthritis, Pickwickian syndrome, ischaemic heart disease, peptic, gastric, and duodenal ulcers, CVHD, fibrosis, lipodystrophy, herpes infection, candidiasis, burns, dermatitis, dermatomyositis, sunburn, urticaria, warts, wheals, acne, eczema, oily skin, rosacea, cutaneous lymphoma, and Behcets's syndrome.

8. A method according to claim 5, wherein the disease is a disease of the microvasculature of adipose tissue or skin selected from the group consisting of a venular disorder and a non-venular disorder.

9. A method of treating a microvessel endothelial cell-associated disorder of adipose tissue or skin in a subject in need thereof, comprising administering to the subject an effective amount of a microvessel endothelial cell targeting agent which binds to a protein encoded by Il6st expressed on the surface of a microvessel endothelial cell in adipose tissue and skin, wherein the microvessel endothelial cell targeting agent is delivered specifically to a microvessel endothelial cell in adipose tissue and skin expressing the protein encoded by Il6st; and the microvessel endothelial cell targeting agent is a therapeutic agent for treating the microvessel endothelial cell-associated disorder.

10. A method according to claim 9, wherein the microvessel endothelial cell targeting agent is internalized into or transported across the endothelial cells lining the microvessel.

11. A method according to claim 9, wherein the microvessel endothelial cell-associated disorder of adipose tissue or skin is selected from the group consisting of a venular disorder and a non-venular disorder.

12. A method of delivering a targeting agent to a microvessel endothelial cell in adipose tissue or skin, comprising administering a microvessel endothelial cell targeting agent which binds to a protein encoded by Il6st expressed on the surface of a microvessel endothelial cell in adipose tissue or skin, wherein the microvessel endothelial cell targeting agent is delivered specifically to a microvessel endothelial cell in adipose tissue or skin expressing the protein encoded by Il6st and causes an effect in the microvessel endothelial cell, or a microvessel, tissue or organ adjacent to the microvessel endothelial cell.

* * * * *